(12) United States Patent
Moon

(10) Patent No.: US 10,905,336 B1
(45) Date of Patent: Feb. 2, 2021

(54) SYSTEMS AND METHODS FOR MEASURING, QUANTIFYING, DISPLAYING AND OTHERWISE HANDLING/REPORTING HEALTH STATUS DATA AND RISKS VIA SELF-DIRECTED HEALTH SCREENING, INFORMATION, AND PROCESSING INFORMATION REGARDING ASSOCIATED PROFESSIONAL ADVICE

(71) Applicant: Jorlin E. Moon, Sunnyvale, CA (US)

(72) Inventor: Jorlin E. Moon, Sunnyvale, CA (US)

( * ) Notice: Subject to any disclaimer, the term of this patent is extended or adjusted under 35 U.S.C. 154(b) by 37 days.

(21) Appl. No.: 16/159,558

(22) Filed: Oct. 12, 2018

Related U.S. Application Data

(60) Provisional application No. 62/571,749, filed on Oct. 12, 2017.

(51) Int. Cl.
*A61B 5/00* (2006.01)
*A61B 5/0205* (2006.01)
(Continued)

(52) U.S. Cl.
CPC .............. *A61B 5/0205* (2013.01); *A61B 3/12* (2013.01); *A61B 5/0077* (2013.01);
(Continued)

(58) Field of Classification Search
CPC ..... A61B 5/0205; A61B 5/445; A61B 5/0077; A61B 5/0533; A61B 5/4244; A61B 5/01; A61B 5/0079; A61B 5/7495; A61B 5/4504; A61B 5/449; A61B 5/444; A61B 5/7445; A61B 5/083; A61B 5/024; A61B 3/12

See application file for complete search history.

(56) References Cited

U.S. PATENT DOCUMENTS 6,628,810 B1 * 9/2003 Harkin ................ G07C 9/37
 382/116
8,733,641 B1 * 5/2014 Drew ................ G06Q 50/22
 235/381

(Continued)

*Primary Examiner* — Mallika D Fairchild
(74) *Attorney, Agent, or Firm* — Greenberg Traurig, LLP

(57) ABSTRACT

Self-directed health screening systems and methods utilizing user navigation and device integration, health analyzing algorithms, and/or self-learning techniques for the detection, quantifying, prevention, and management of health risks and discoverable health conditions. Implementations herein may include components or involve aspects associated with information collection, information processing, display/provision/rendering of professional advice, and/or processing of various associated data and information via network(s). Implementations herein provide for innovatively configured, easily upgradable, efficient, portable, scalable, easy-to-use, usage-encouraging, and/or effective implementations for screening, predicting points of inflection of pending health issues, preventing and/or managing users' health, provided via various and multiple embodiments having numerous advantages over other known techniques. Screenings, health information, and user-selectable choices may be optimized for each unit by offering different combinations over a period of time and iterating to produce the greatest usage and user traffic thereby best serving the specific health needs of the user base and sponsoring advertisers.

21 Claims, 57 Drawing Sheets

(51) Int. Cl.
*A61B 5/01* (2006.01)
*A61B 5/0533* (2021.01)
*A61B 5/083* (2006.01)
*A61B 3/12* (2006.01)
*A61B 5/024* (2006.01)

(52) U.S. Cl.
CPC .............. *A61B 5/0079* (2013.01); *A61B 5/01* (2013.01); *A61B 5/0533* (2013.01); *A61B 5/083* (2013.01); *A61B 5/4244* (2013.01); *A61B 5/444* (2013.01); *A61B 5/445* (2013.01); *A61B 5/449* (2013.01); *A61B 5/4504* (2013.01); *A61B 5/7445* (2013.01); *A61B 5/7495* (2013.01); *A61B 5/024* (2013.01)

(56) References Cited

U.S. PATENT DOCUMENTS

| | | | |
|---|---|---|---|
| 2008/0021840 A1* | 1/2008 | Beenau | H04L 63/0861 |
| | | | 705/64 |
| 2008/0189173 A1* | 8/2008 | Bakar | A61B 3/18 |
| | | | 705/14.14 |
| 2012/0127433 A1* | 5/2012 | Moon | A61B 3/00 |
| | | | 351/223 |
| 2017/0014058 A1* | 1/2017 | White | A61B 5/14532 |

* cited by examiner

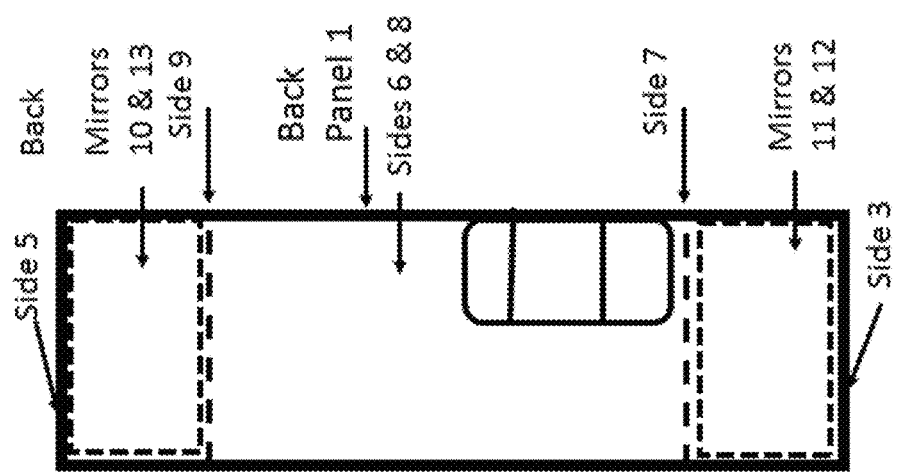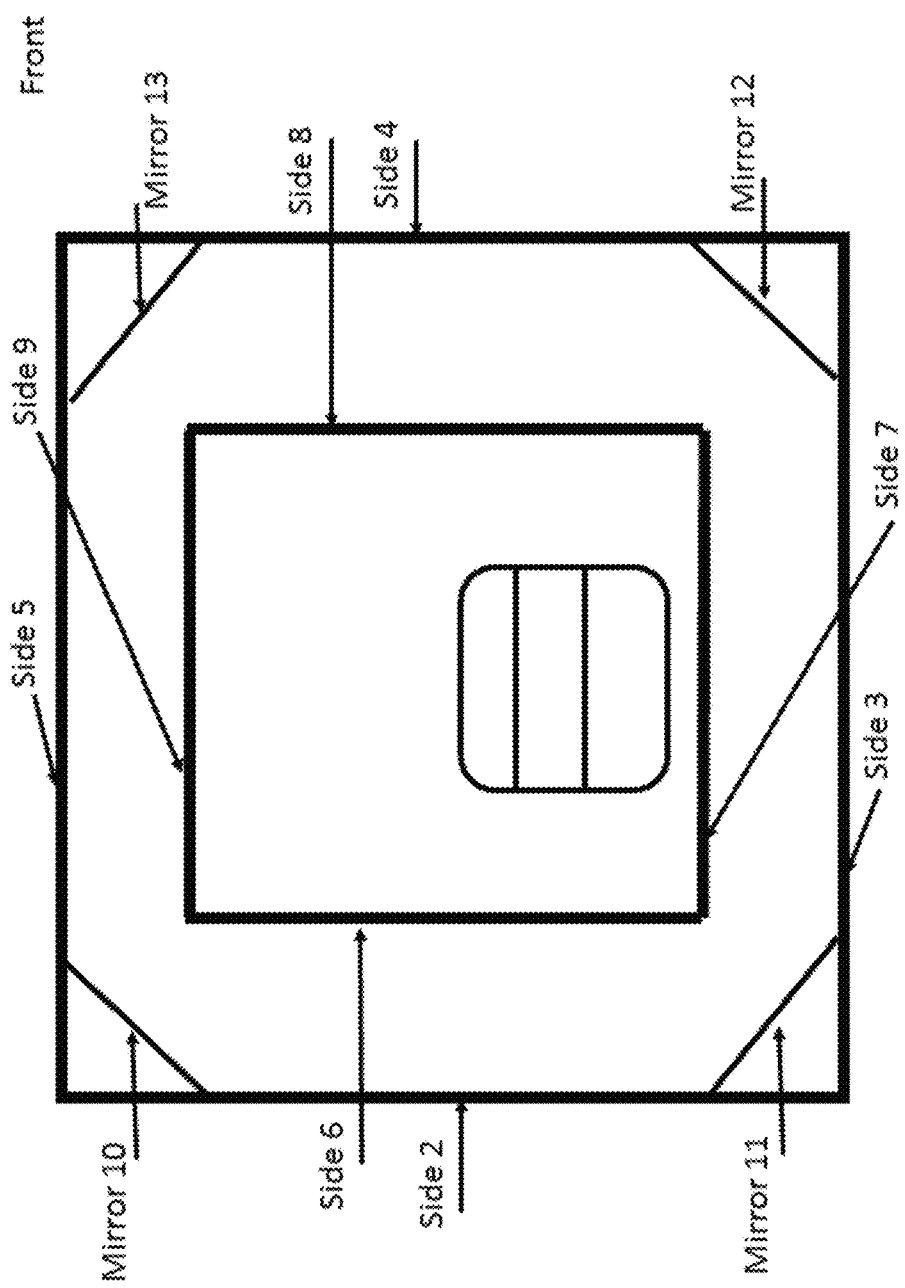

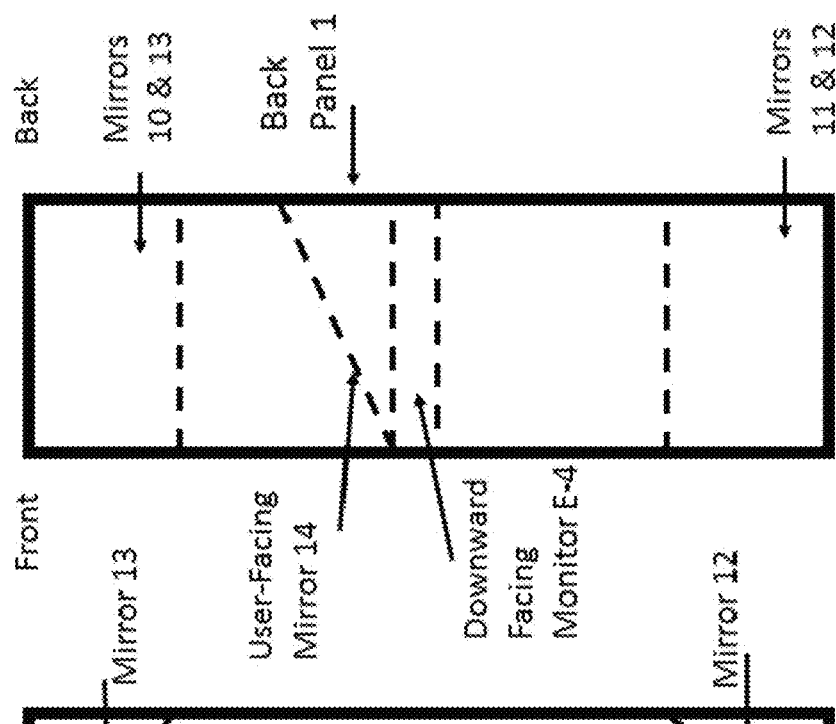
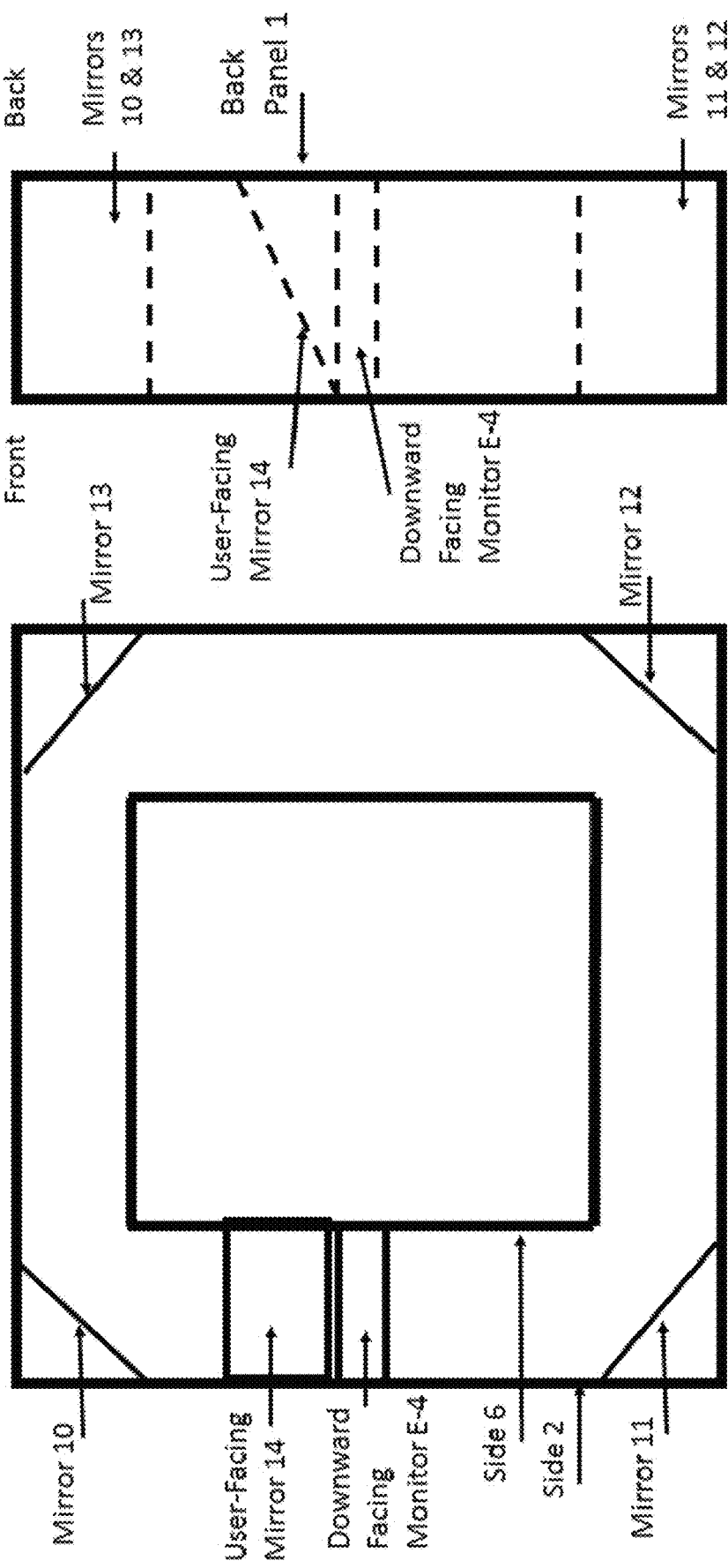

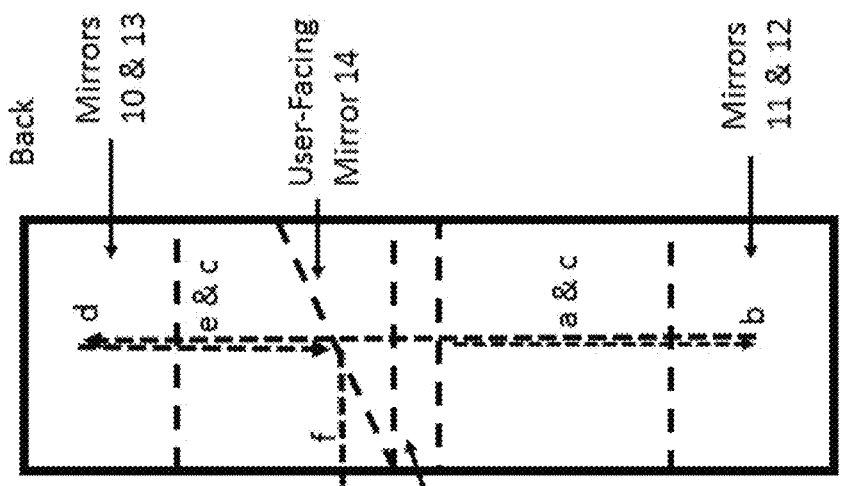
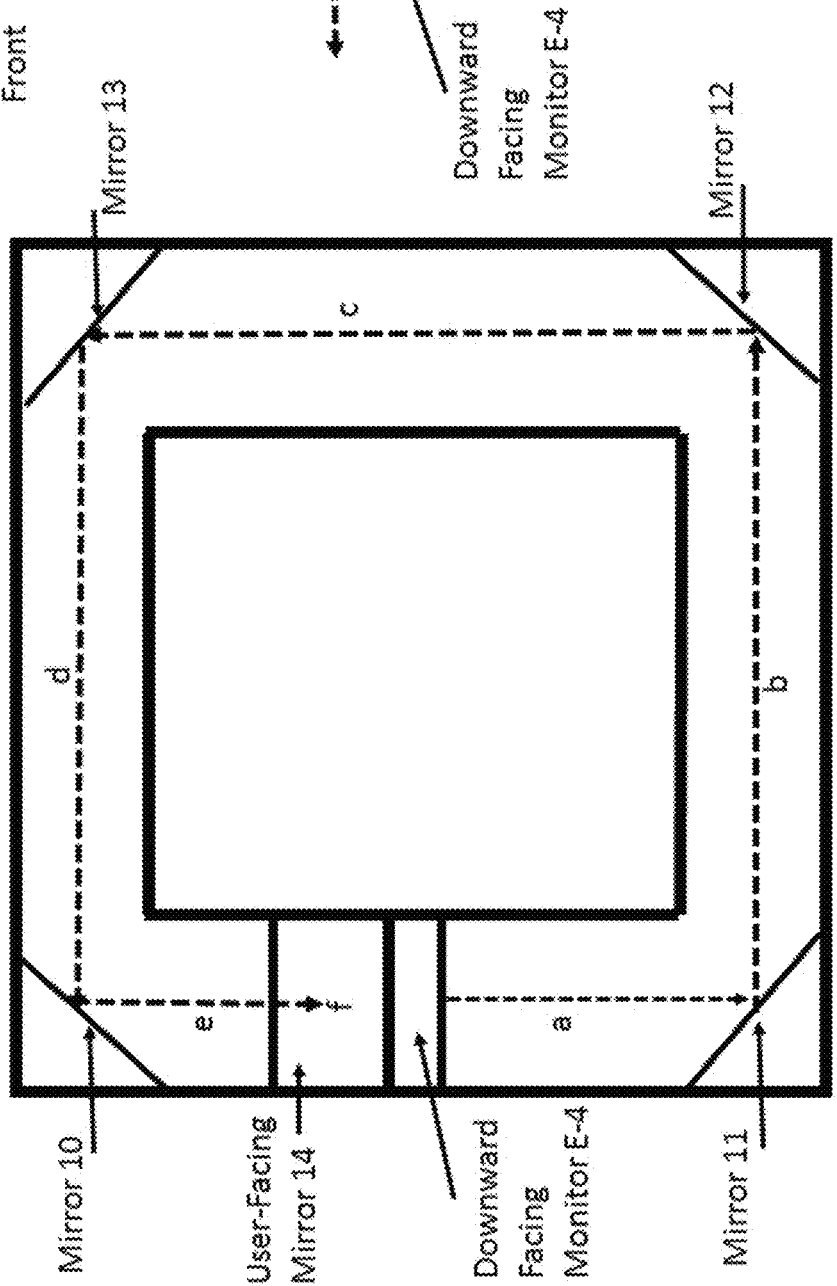

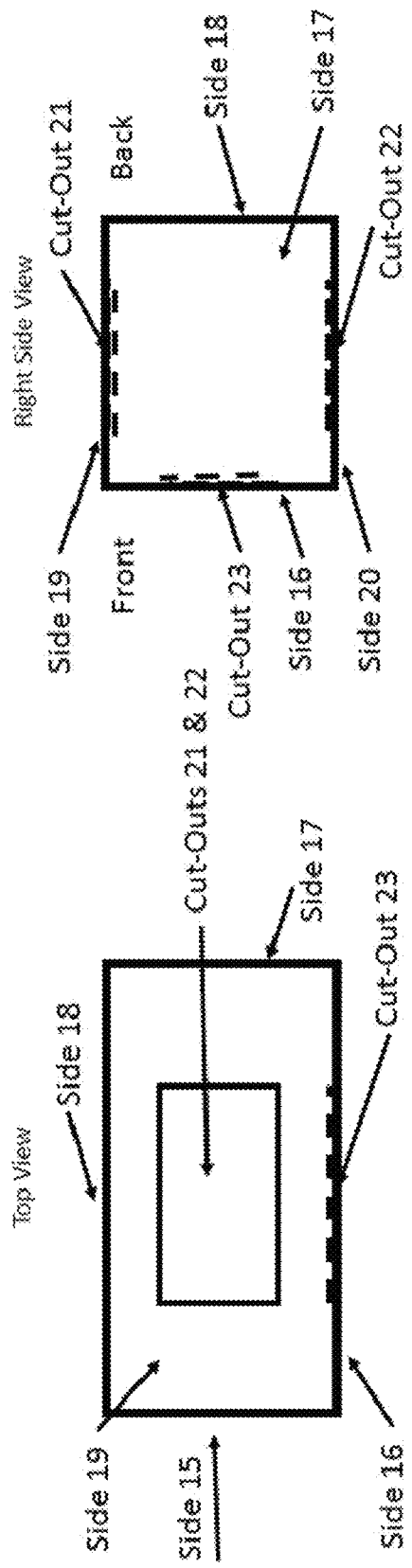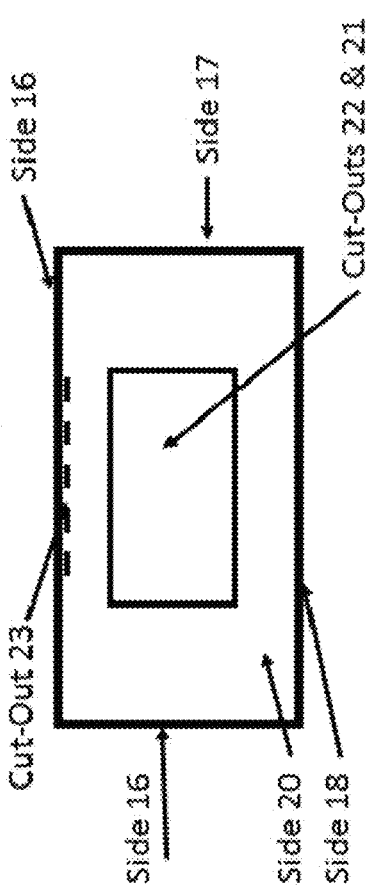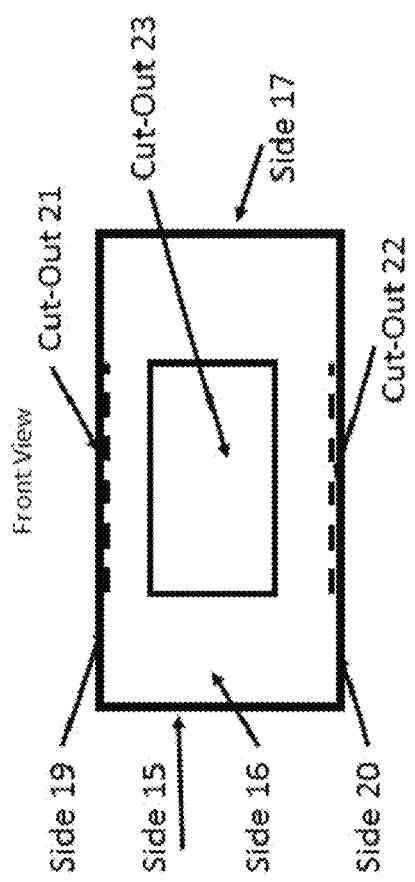

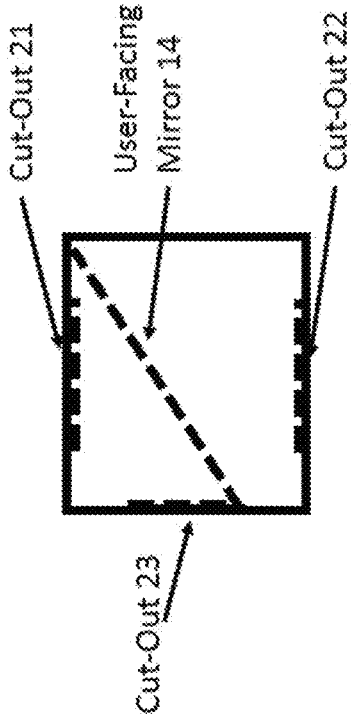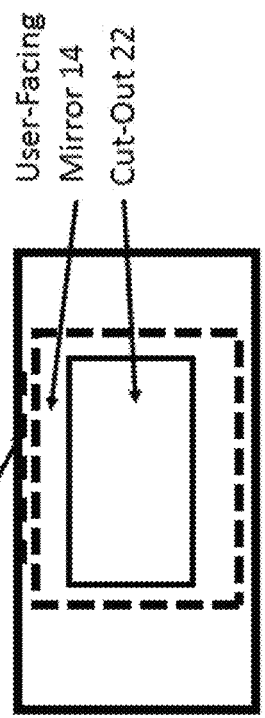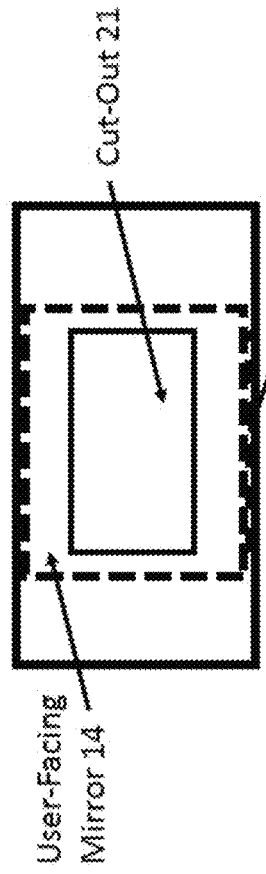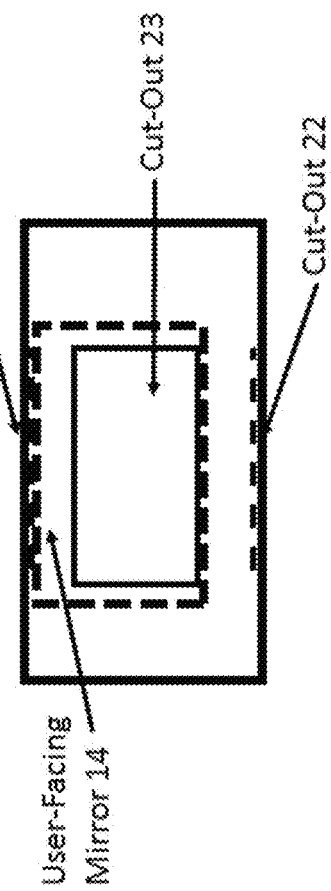

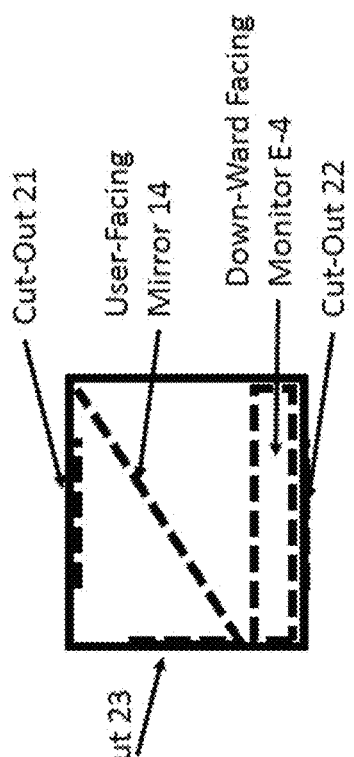
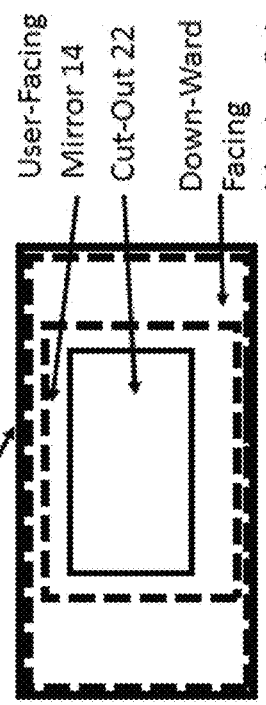
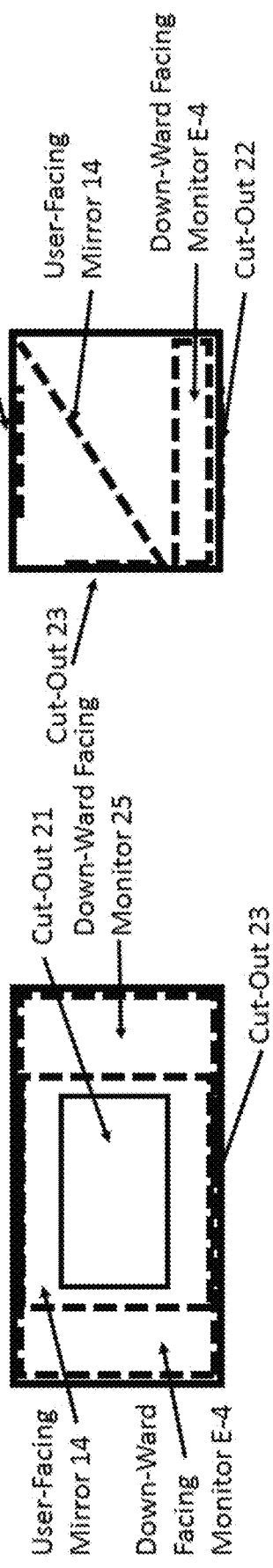
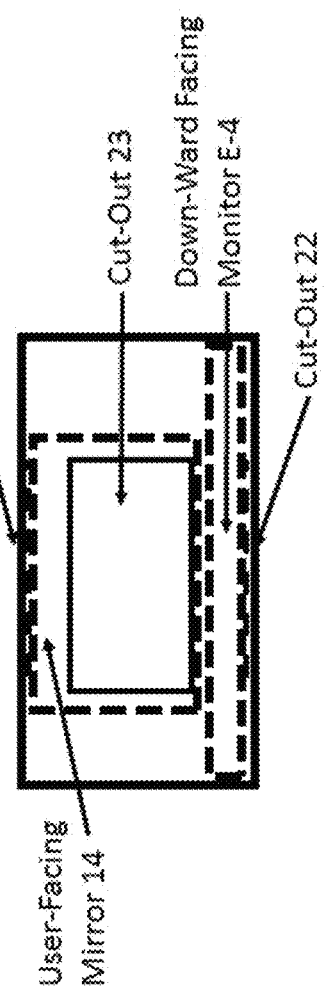

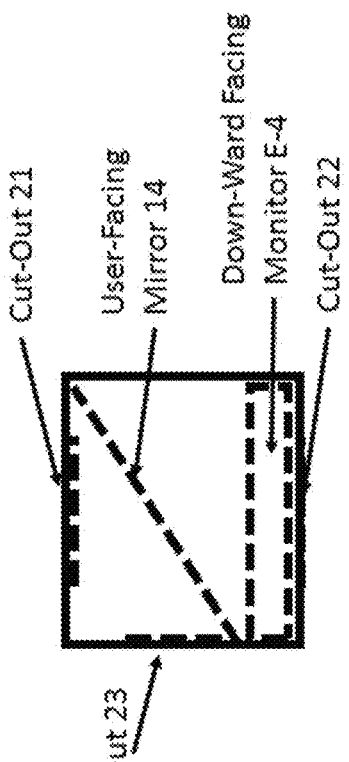
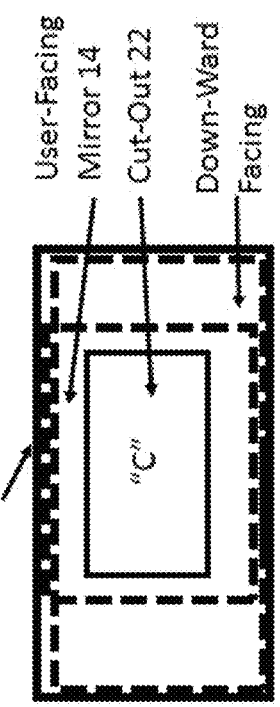
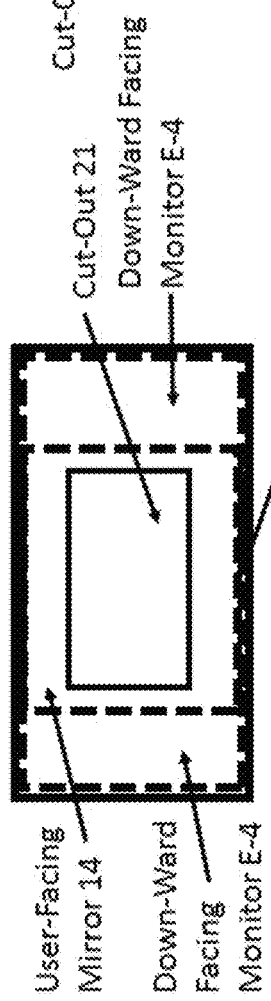
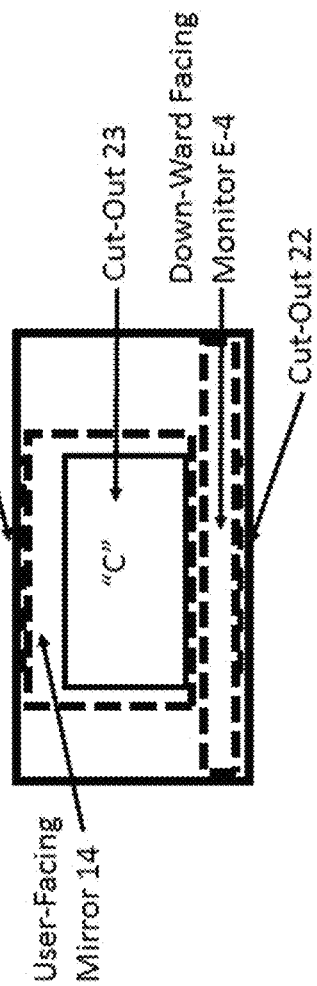

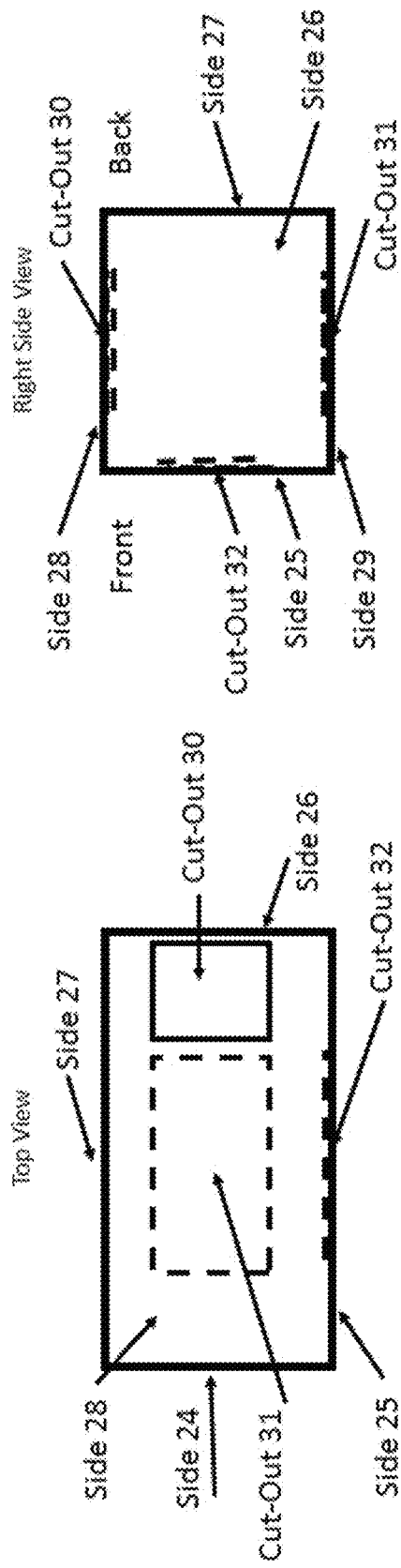
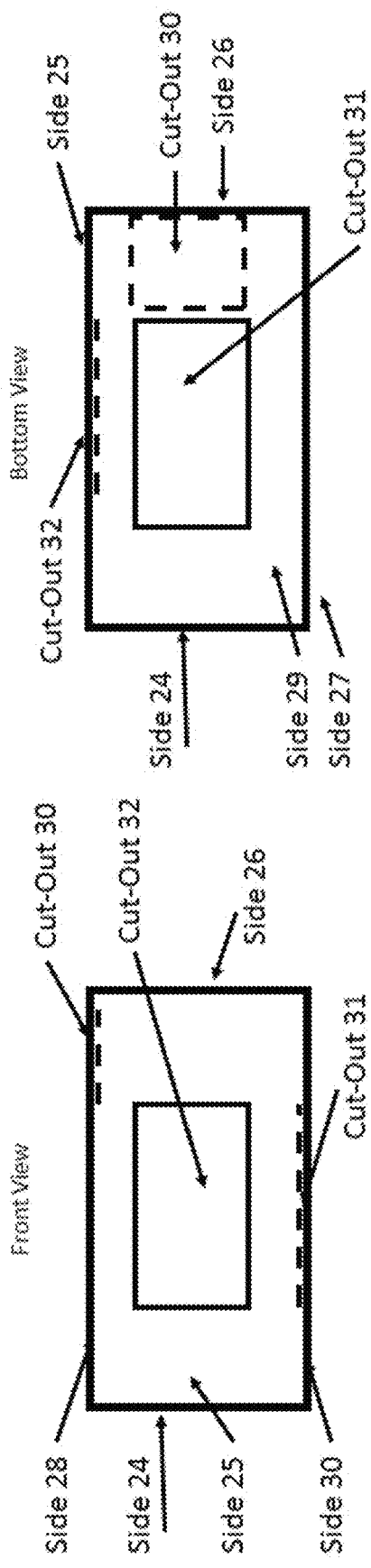

Right Side View

Bottom View

Top View

Front View

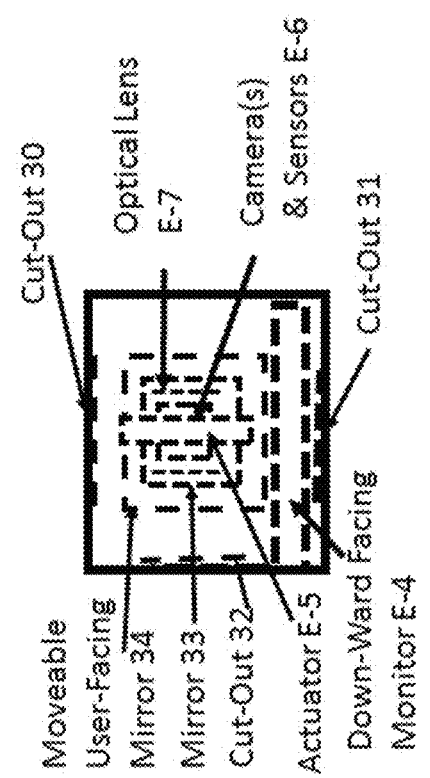
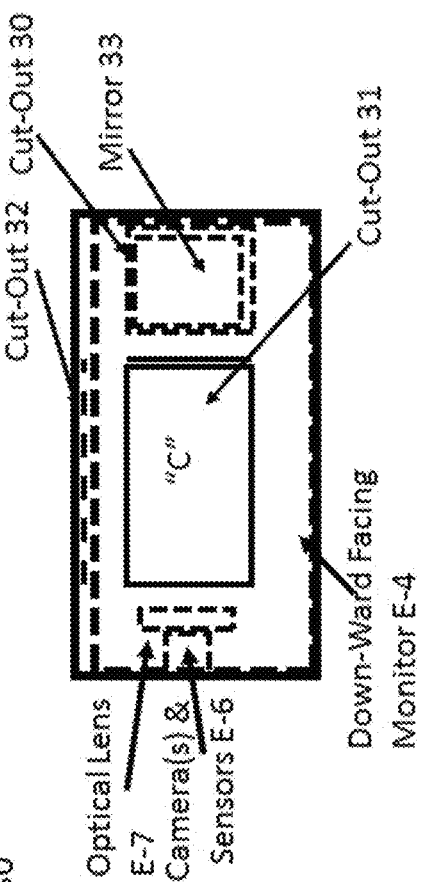
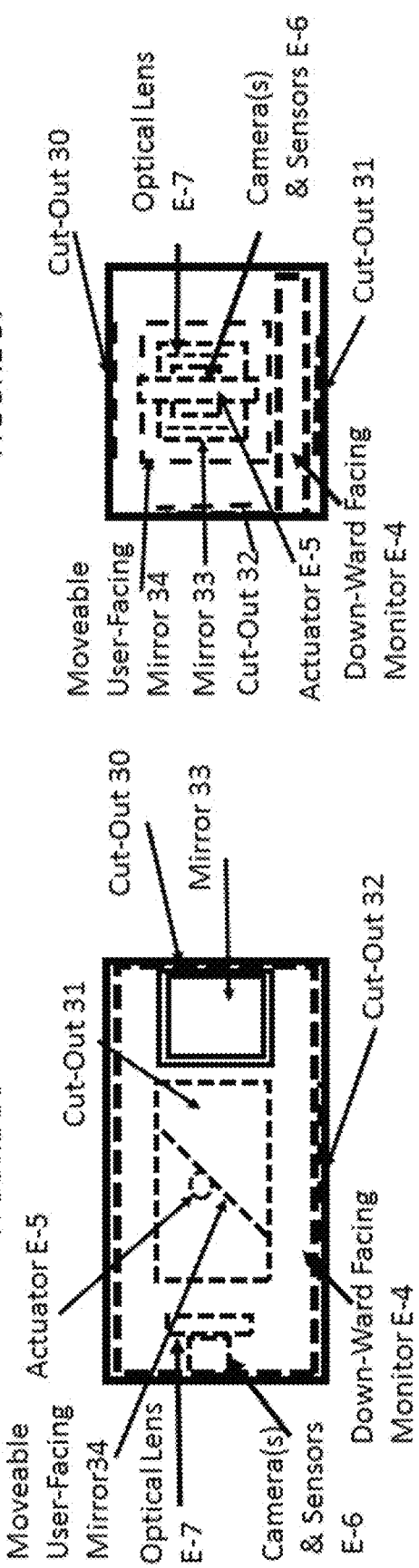
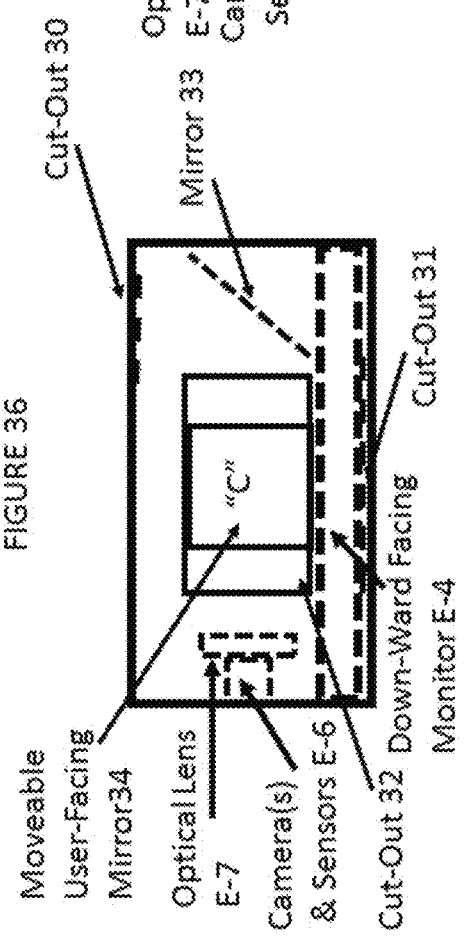

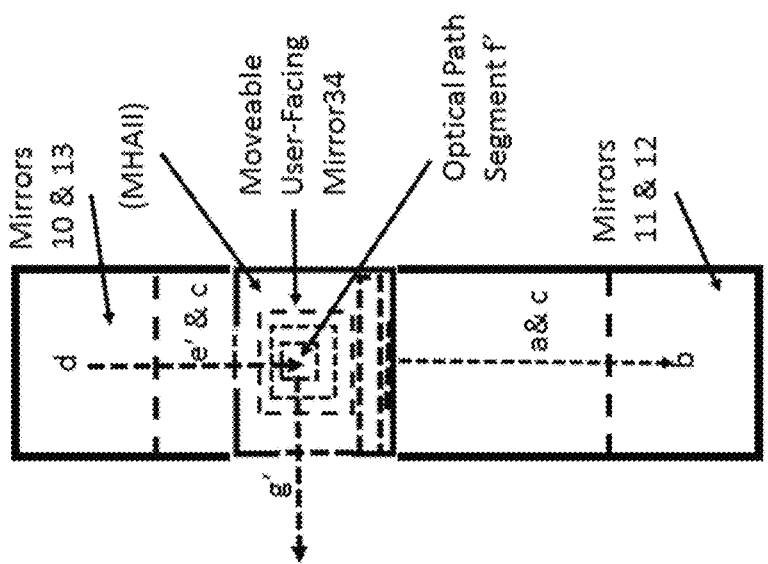
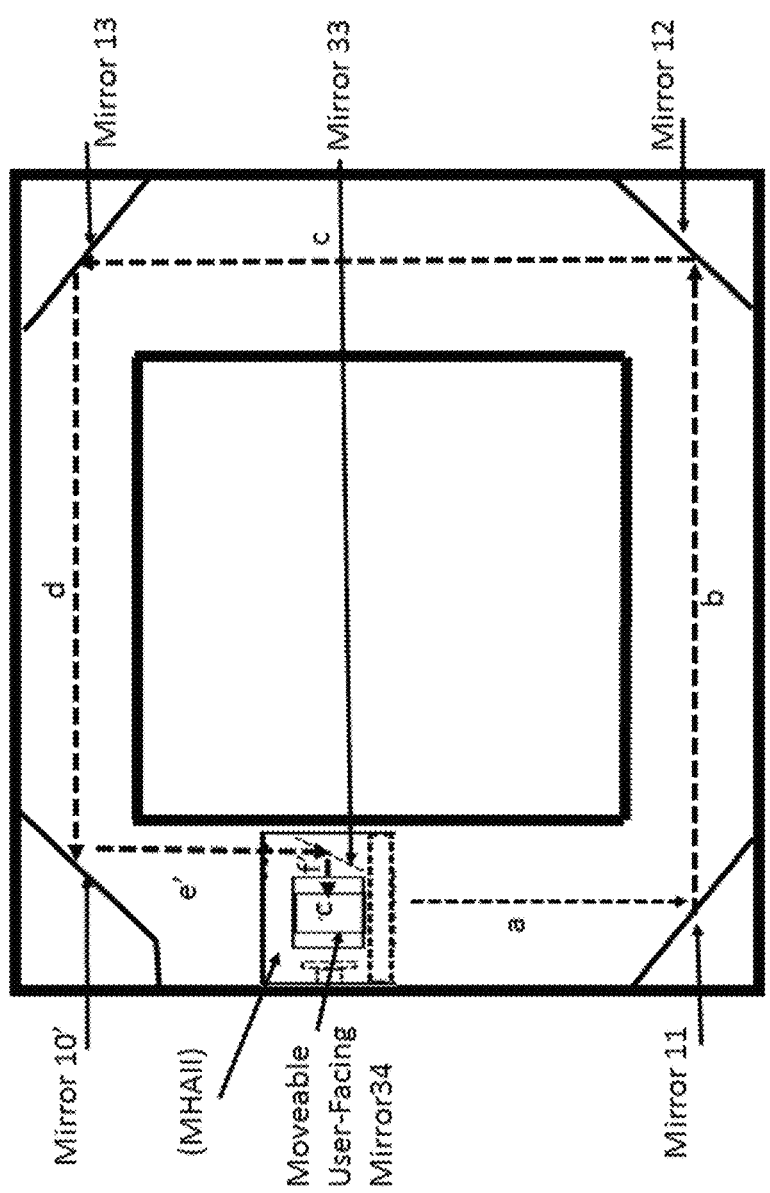

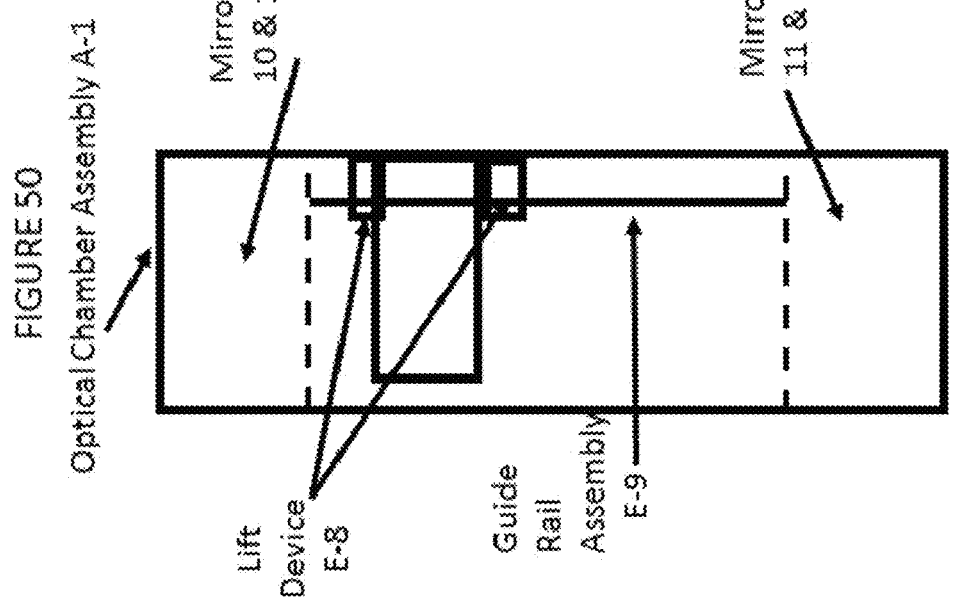
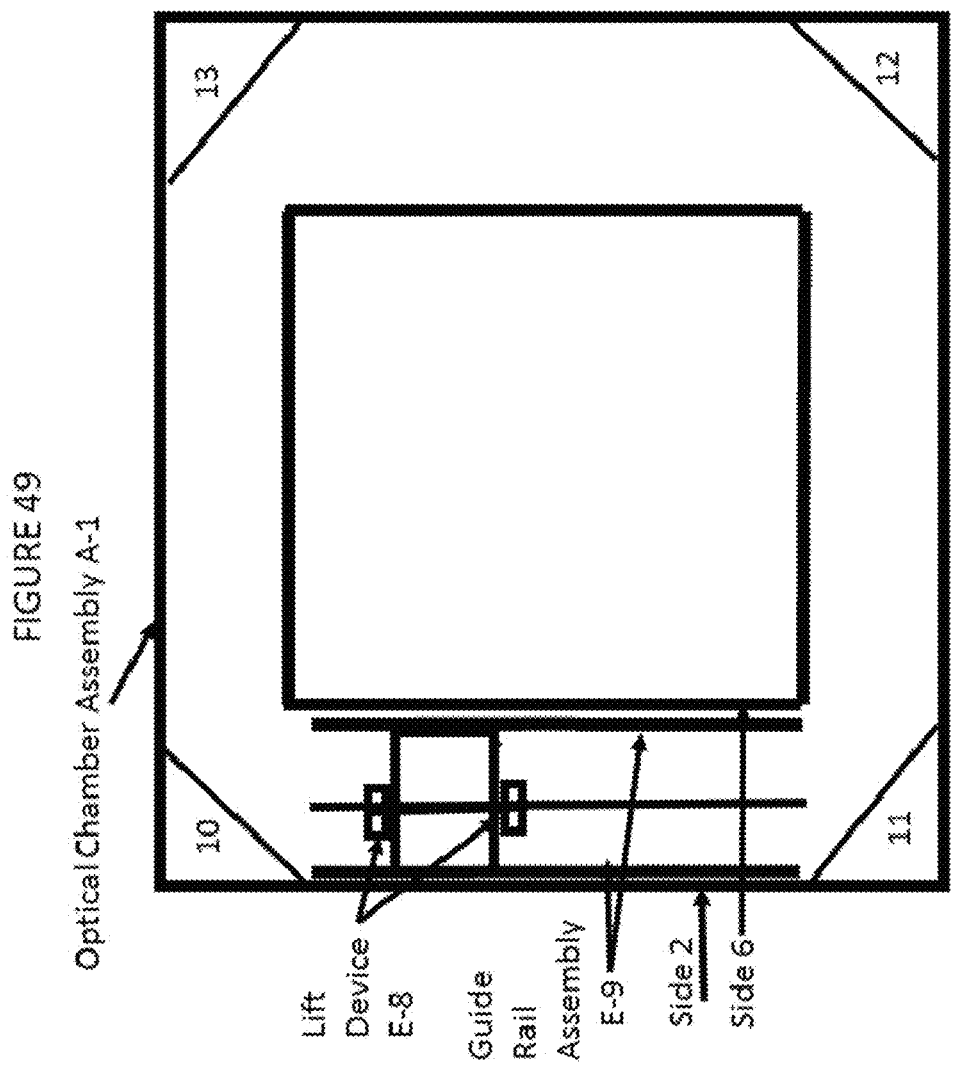

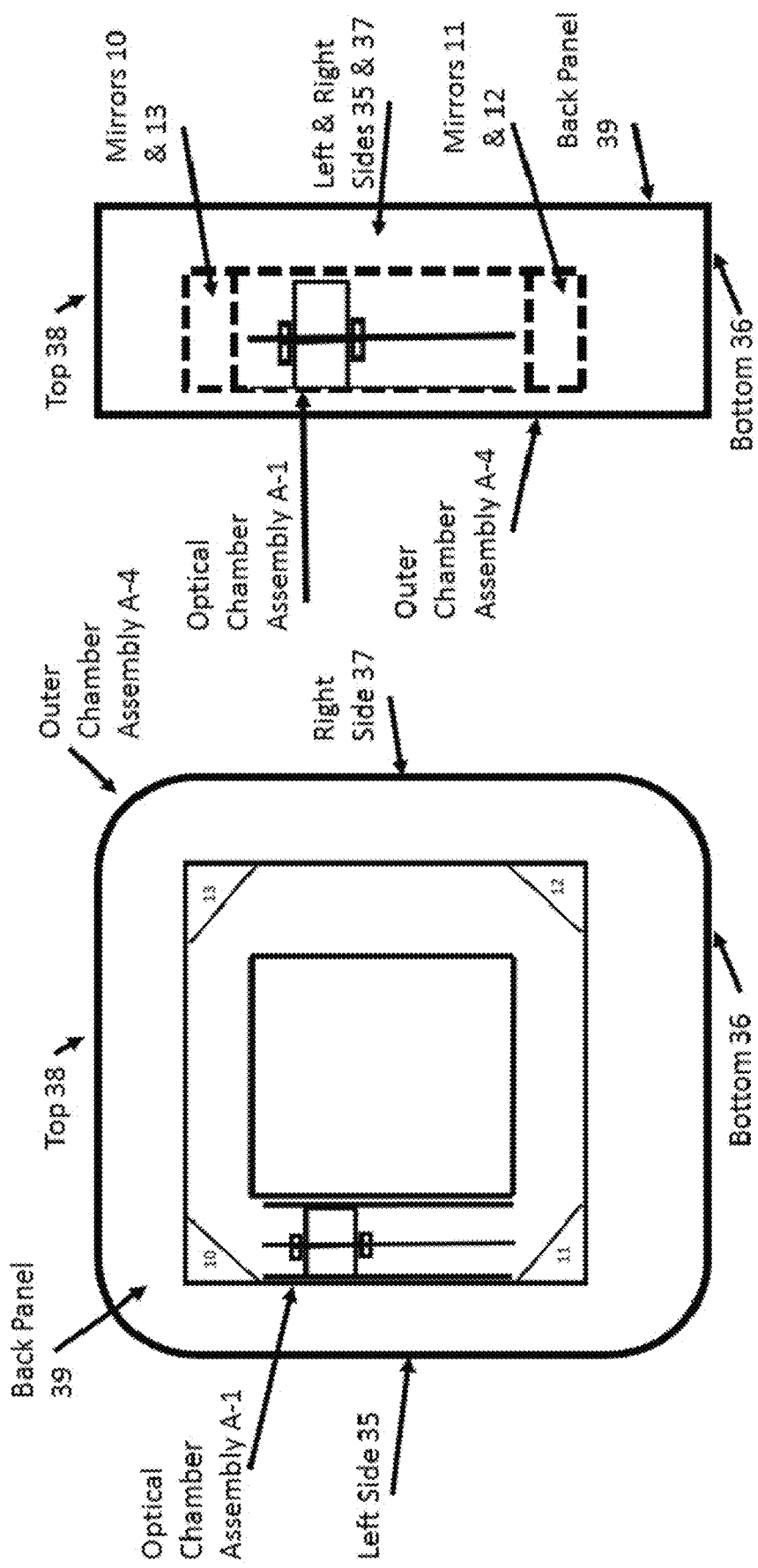

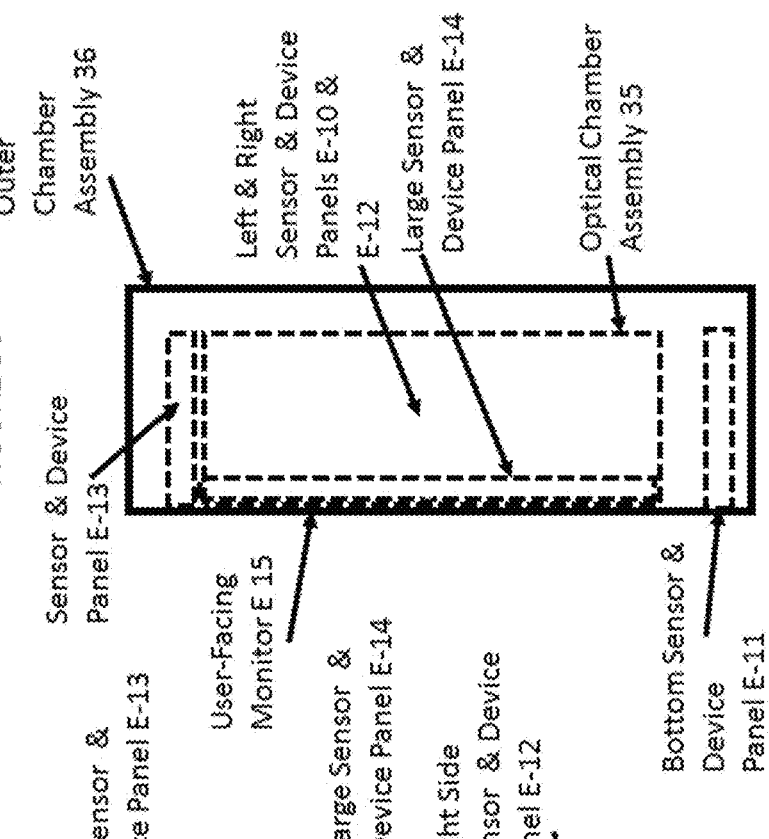
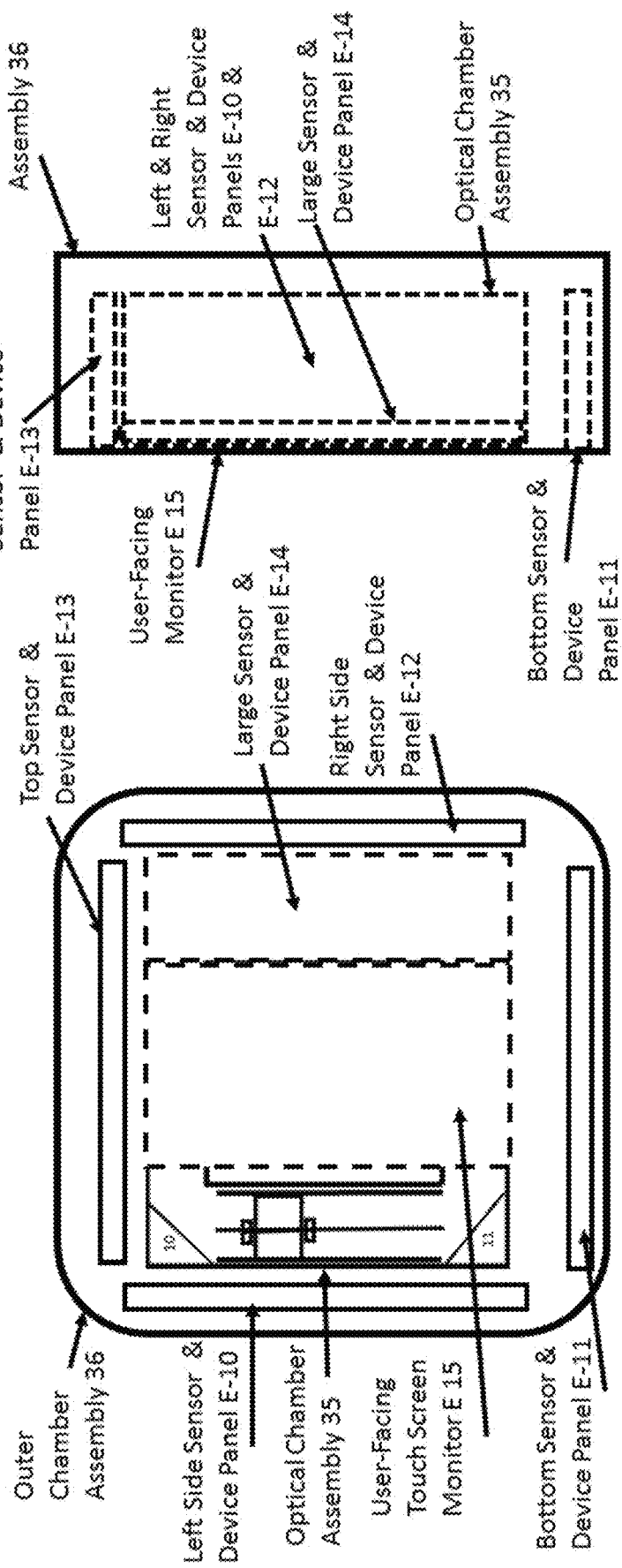

MECHANICAL ASSEMBLY MA

SYSTEMS AND METHODS FOR MEASURING, QUANTIFYING, DISPLAYING AND OTHERWISE HANDLING/REPORTING HEALTH STATUS DATA AND RISKS VIA SELF-DIRECTED HEALTH SCREENING, INFORMATION, AND PROCESSING INFORMATION REGARDING ASSOCIATED PROFESSIONAL ADVICE

CROSS-REFERENCE TO RELATED APPLICATION INFORMATION

This application claims benefit/priority of provisional patent application No. 62/571,749, filed Oct. 12, 2017, which is incorporated herein by reference in entirety.

APPENDIX INFORMATION

This application also includes one or more Appendix documents, which is/are incorporated herein by reference and are also incorporated herein explicitly via submission herewith. These Appendices comprise and/or involve features related to the innovations herein including but not limited to user interfaces, navigation and related GUI navigation, advertising features, design and layout (e.g., vision screening, hand screening, etc.), additional details regarding adjustment of the moveable housing assembly (e.g., adjustment to eye level, etc.), improved provision of information (e.g., in multiple languages, etc.), presentation of screening assessment and/or results, among other things.

OVERVIEW

Self-directed health screening systems and methods utilizing unique user navigation and device integration, health analyzing algorithms, and self-learning techniques for the detection, quantifying, prevention, and management of health risks. One or more implementations herein may include, though are not limited to, use of optical, mechanical, electrical, computational and software components and/or may involve aspects associated with information collection, information processing, display/provision/rendering of professional advice, and/or processing of various associated data and information via one or more networks. Systems and methods herein provide for innovatively configured, efficient, portable, scalable, easy-to-use, usage-encouraging, and/or effective (including cost-effective) implementations for screening, predicting, preventing and/or managing users' health, provided via various and multiple embodiments having numerous advantages over any and all other techniques available.

BACKGROUND

Health care systems around the world are being strained by the number of patients in need of care, a growing shortage of health care professionals and facilities, and the escalating cost of providing treatment. Adding to the strain upon health care systems is a general lack of health knowledge on the part of individuals as to their current health status, and prevention and treatment measures for discoverable health conditions. Individuals often do not know when to take action on a particular health condition or disease, and the impact upon their health if no action is taken.

Among the many health conditions a user may experience, a few stand out as life-altering, diminishing both quality of life and longevity.

Vision Loss & Impairment

Technology advances in computers, smart phones, tablets, digital readers, and a myriad of digital entertainment systems are placing an increasing visual load on our eyes in and out of the workplace. We need to see well to perform our work accurately, including children in school, and attention to eye health is one of the best preventive measures to maintain sight throughout all stages of life. Approximately 60 million Americans are currently living with impaired vision due to out dated vision correction (All About Vision). Treatment cost in the U.S. for eye disorders and vision loss approximate $139 Billion (Prevent Blindness). On a global basis, there are approximately 4.2 billion people world-wide with impaired vision (World Health Organization).

Diabetes

The world population is experiencing a rapid increase in the number of cases of diabetes. There are approximately 29.1 million people in the U.S. with diabetes with an alarming number of new cases in both adults and children. Approximately 8.9 million Americans have undiagnosed diabetes and there are approximately 86 million Americans with a pre-diabetic condition, many of whom are unaware that they have this condition nor realize the impact on their health if their condition advances. Treatment costs for diagnosed diabetes is $245 Billion in the U.S. (American Diabetic Association). Diabetic retinopathy is the leading cause of blindness among adults, yet this condition is treatable if diabetics are aware of their condition and seek timely medical help. However, 40% of diabetes have never had a full, dilated eye exam by an eye care professional. Sixty percent of surveyed diabetics in danger of losing their sight could not recall a doctor describing to them the link between diabetes and vision loss. (Johns Hopkins Research, JAMA Ophthalmology)

Body Mass Index, BMI

BMI is a leading indicator of many severe health conditions including diabetes, stroke, heart disease, and even cancer. Approximately 78.6 million Americans are obese (JAMA) and the annual medical cost of treating obesity is $147 Billion (CDC). A large portion of those with a high BMI are unaware of the health conditions that can accompany their disease.

Hearing Loss

Hearing loss is increasing at alarming rates among both adults and children due to aging, noise pollution, and the growing use of wearable headphones that often exceed healthy noise levels. The impact upon quality of life of hearing loss equals or exceeds that of loss of vision due to the isolation from society and accompanying depression an individual may experience with deafness. According to the CDC, approximately 12.5 percent of children and adolescents ages 6 to 19 have suffered permanent damage to their hearing due to excessive noise exposures. Over 40 million adults are living with some form of hearing loss (Johns Hopkins) and over 80 percent of those have not sought medical help or treatment (NIH).

In response to these trends, people are beginning to pay more attention to their health and are seeking more preventive measures. Many solutions, some effective more than others, are being created to address a number of health conditions and diseases including wearable digital health devices, health related kiosks, retail in-store health clinics, and a growing number of corporate sponsored health programs to name a few.

More specifically, newly released self-directed health screening kiosks such as Higi and Solo-health (now Pursuant) are attempting to address a few of the major health concerns people have. In practice, however, these machines are not much more than updated blood pressure devices that provide a few additional health measurements. These units are typically found in retail pharmacy locations and some corporations. There are several drawbacks of these devices including (1) requiring a user to sit down and thus enabling screening of only one user at a time, (2) limiting use to those over the age of 18 due to FDA requirements, (3) excluding those with limited movement and dexterity and are not readily wheelchair accessible, (4) limiting their placement opportunities due to their size, weight, and cost, (5) offering a static number of screenings due to their inability to easily add new technology and user screenings, and (6) requiring significant testing, field calibration, and maintenance that may result in inaccurate screening responses. They also have a major drawback in that medical institutions such as the Mayo Medical Clinic and others do not recommend making health decisions based on information received from retail blood pressure machines due to inaccurate readings arising out of inappropriate cuff size, user operating error, and calibration issues. These drawbacks, and other drawbacks, of existing self-screening machines create a need for a fast, easy to use, light weight, and accurate self-directed screening device that provides meaningful user health screenings and data, professional health resources, preventive measures, predictive outcomes base upon user actions or non-actions, and easily upgradable to take advantage of advances in health knowledge and new technology.

Summary of Certain Aspects The purpose of the current inventions is to provide these improvements in an integrative, digital health screening experience that combines a user's screening data and data from other sources, into a current health baseline status. The current inventions then suggests actions to prevent or manage a particular health condition or disease, and recommend nearby health care professionals and resources to visit when further assessment or treatment is indicated.

Unlike other self-screening devices, the present inventions has a small form factor allowing back-to-back units for screenings by multiple users, and light weight to allow it to be shipped and placed in many locations, even around the world. The current inventions has few moving and mechanical parts, requires no field calibration, and provides a platform for easily installing additional health screenings to keep up with advances in medical knowledge and new sensor and data acquiring technology. Current health screenings include: unique and highly accurate vision acuity screening, and an anterior and posterior eye health assessment; BMI screening and interactive predictive tool showing how this important health parameter changes with various levels of weight loss; diabetes risk assessment and disease management including impact on vision, hearing, oral health, skin, and podiatry issues; assessment of blood pressure, pulse, heart rate, EKG, galvanic skin response; and hearing assessment. The present inventions also provides an interactive tool that recommends a type of hearing solution, including devices offered by specific vendors of hearing loss products that address the parameters of a user's unique hearing loss. The present inventions provides a hand and skin screening and analysis for the possible detection of skin disorders, including skin cancer, joint issues, liver problems, osteoarthritis, thyroid and hypothyroidism, anemia, lung disease and impaired oxygen levels.

Data handling and analysis from information derived by the present inventions allow long term and diverse longitudinal health studies that will be both status quo and predictive in nature. The present inventions also includes means for accepting credit and membership cards allowing users to purchase products and services.

A unique feature of the present inventions is encouraging users take proactive steps to improve their health. To this end, a library of video bites of possible user results is stored in memory and threaded together upon playback to provide a user with their specific and unique health screening results, thus imitating a natural sounding conversation such as with a health care provider.

Another unique feature of the present inventions is to encourage users to swipe their membership or credit cards and thus enter some identifying information that can be used when user makes their purchases at the check center. The present inventions is then enabled to provide user health and demographic parameters for each product in a user's shopping cart at check-out, while protecting the specific identity of the user.

The present inventions also provides software allowing the company or advertisers to create and publish specific content to specific geographically located devices. Publishing different content to different locations allows the current inventions to conduct AB testing and analyze the results. The user and marketing information gained from these locations aid advertisers to improve their messaging content to optimize user experience and advertiser sales.

With the collection and aggregation of multiple user data, the present inventions is able to determine and provide a user with the probability of either health improvement or degradation due to specific actions taken or not taken by the user.

BRIEF DESCRIPTION OF THE DRAWINGS

FIGS. 1-8, 25-26, 39-40 and 49-60 are illustrative plane and side views of one or more implementations consistent with aspects related to the innovations herein.

FIGS. 9-12, 13-16, 17-20, 21-24, 27-34 are sets of illustrative top, front, side, and bottom views of one or more implementations consistent with aspects related to the innovations herein.

FIGS. 35-38 and 41-48 are illustrative, inter-related views of one or more implementations consistent with aspects related to the innovations herein.

FIGS. 87A-90 are illustrations of detailed, expanded and/or alternative embodiments and/or views associated with one or more implementations consistent with aspects related to the innovations herein.

Figure 1:
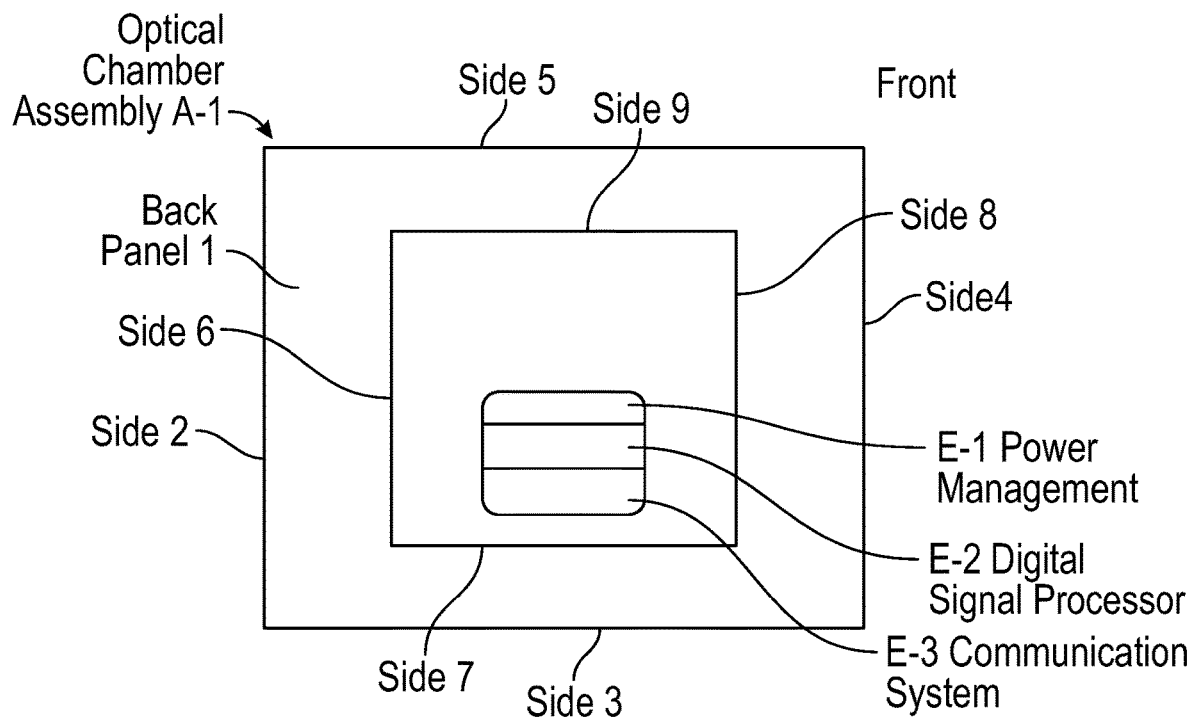

The following is a detailed descriptions consistent with various aspect of the present innovations.

OVERVIEW OF SOME ASPECTS OF THE INNOVATIONS HEREIN

Self-Administered Health Screening

One of the objects of the present inventions is to provide a self-administered health screening for determining a baseline status for many important health parameters, and using Artificial Intelligence (AI) to recommend professional intervention when indicated, predict future health patterns from base-line data and future user action steps, and supply preventive measures when appropriate to mitigate or avoid a particular health condition or conditions.

Enable Future Hardware and Software

Another object of the inventions is to anticipate the growth of health knowledge and technology by enabling the present inventions to easily add future screening hardware and software components. Multiple cage-ready compartments in the present inventions provide electrical power, processing and communication abilities to present and future sensors and device arrays and accompanying software.

Screening for a Wide Variety of Conditions

The present inventions comprised of electrical, mechanical, computational, optical and software components including artificial intelligence gather and process information for screening of, but not limited to, a user's: visual acuity, including distance vision, near vision, central vision, contrast sensitivity and color blindness; eye health including analysis of anterior and posterior portions of the eye related to the presence of diabetic retinopathy, macular degeneration, glaucoma, cataracts, retinal and other vision diseases; dry eyes and ocular allergies; ocular symptoms related to computer use, smart phones, and other visually dependent electronic entertainment, computational, or communication devices; blood pressure; Body Mass Index (BMI), risk of various health conditions including but not limited to diabetes, heart conditions, murmurs, and cardiovascular system, skin disorders; joint issues; liver problems, osteoarthritis; thyroid and hypothyroidism; anemia; lung disease and impaired oxygen levels.

Providing Information to the User

Another object of the inventions is providing information to the user on the health conditions described above and recommend action steps based on whether a user's risk of these conditions appears to be mild, moderate, severe, or indeterminable, including but not limited to making an appointment with a health care professional.

Network Connectivity

The present inventions will be deployed as a network with internet connectivity in many locations such as pharmacies, retail outlets, companies, hospitals, clinics, schools, government facilities, malls, and other high traffic venues. This network and the data collection of user health and lifestyle parameters provides the basis of numerous longitudinal studies for the quantifying and analyzing of interdependencies of user health conditions and their progression, and predictive outcomes of treatment and non-treatment options.

Issues can Affect an Individual's Health

The present inventions will address a number of issues that can affect a person's health including, but not limited to, diet, exercise, and lifestyle habits such as smoking, alcohol and substance use, and relationships.

Increase Efficiency of Country's Health System

Another object of the inventions is to increase the efficiency of a country's health system and reduce costs by providing screening results to a health professional prior to a consultation and/or treatment. The inventions will also include a telemedicine platform that will allow a health care professional to discuss a user's screening results prior to a scheduled office visit or allow a health care professional to monitor a user's health condition and recommend a treatment regimen prior to an in-office visit.

Library of Audio and/or Video Descriptions

It is also one of the objects of the inventions that a library of audio and/or video descriptions of possible screening results, health information, and suggested actions is created, and through algorithms, components of this library are threaded together to form a unique conversational response to a user's particular health status and needs.

Methods to Encourage Users to Take an Active Role in their Health

Another object of the inventions is to encourage users to take an active role in their health by providing resources such as products and services, including the services of health care professionals and clinics, including clinics within a retail store or company site. Coupons, discounts, special offers, or other incentives will be available to motivate users to respond to presented suggestions and courses of action.

Quick and Automatic Screening Across a Wide Range of Users

Another object of the inventions is to enable screenings to be accomplished quickly and automatically as possible by a large 'age' and 'height' range of users. To this end, the inventions will ask a user to indicate their eye level on a user facing touch monitor. Upon this input the system will move a sensor equipped and terminal end of an optical path that is enclosed in a moveable housing assembly to a user's eye level for vision and eye health screenings. User navigation, information input, and responses to screening questions will also be adjusted to a user's height on a user-facing monitor. Voice recognition will also be available for user input as well as touch input on user-facing monitor. Moveable housing assembly may be adjusted to other heights to record data of other user facial or upper torso features. The system may also automatically record user height through cameras and sensors, such as distance sensors, and adjust moveable housing assembly accordingly to eye level or level of other user features to be screened without user input.

Audio and Video for Input and Output

It is a further object of the inventions to include microphones and speakers in one or more locations, including but not limited to those designated for sensor and device arrays. Speakers will provide audio or video-related audio for system to request user input, instructions for using present invention, present and explain screening results, and other uses including but not limited to, advertisements for products and services. Microphones will provide user voice input for user identification, answers to system questions, and responses associated with various health screenings selected by the user.

Screening of the Hand

Another object of the inventions is to screen and assess a user's hands and wrists including, but not limited to nails, skin, veins, finger joints, tips and finger length, finger and hand swelling, reflex responses, moles, rashes, blotches, color, pulse, blood flow, tremors, and blood pressure. Prior to each user hand screening, the touchable area may be sanitized by various means, including but not limited to ultra-violet (UV) light. Sensor and Device arrays for hand screening may include, but not limited to pressure sensors, microphones, cameras, infrared cameras, color cameras, video cameras, lasers, O2 sensors, and temperature sensors. A real-time video or photo of user's hands placed in the hand screening area may be displayed on User-Facing Monitor to help guide positioning of user hands over sensors and devices.

EXEMPLARY IMPLEMENTATIONS

The following includes exemplary implementations of the present inventions, which should not be considered limiting, as the inventions is limited by the appended claims:

One Embodiment

In one embodiment, the present inventions provides a vision self-assessing system allowing a user to be in a standing or seated position comprising: (a) one or more output devices such as a computer monitor for displaying symbols and graphics used in a variety of visual acuity and ocular health screenings, (b) an optical path comprised of an array of mirrors, where at least one terminal mirror is moveable to adjust to the eye level of the user, (c) a housing assembly containing computer monitor above (a) and terminal mirror(s) of optical path that moves in a vertical direction such that the length of the optical path from displayed vision letters or graphics to user's eyes remain constant regardless of user height, (d) a microprocessor for (1) changing the orientation of displayed symbols and graphics such as oriented in an up, down, left, or right direction on a computer monitor and via the optical path viewed by the user, and (2) changing the size of the displayed symbols or graphics to provide screenings of varying acuities such as 20/10, 20/20, 20/30, 20/40, etc. (e) one or more monitor display screens, such as User-Facing Monitor, preferably a high definition, 4k, 5k or higher definition monitor for providing vision screening for near, central, contrast sensitivity, color blindness, peripheral, and other vision screening, for conveying information and accepting user input, (f) other input devices and sensors, including cameras and lenses to assess a user's back-of-the eye health and a variety of other user biometric parameters, (g) microphones for accepting user commands with voice recognition and for "voice" analysis. (h) one or more sensors to determine a user's height and eye level, (i) a microprocessor for analyzing and processing input and generating output information, (j) memory for data storage and devices that allow access to the internet for data transmission purposes, (k) algorithms for processing data, and providing results to user including current health status, current action items, predictive future health status, and suggested prevention strategies.

Embodiment Including Memory

A further embodiment of the inventions includes a system as above, where the system comprises memory storage within the system of the present inventions or other memory storage accessed through LAN or internet connected devices.

Embodiment Wherein Moveable Housing Assembly Adjusts to Eye Level

In another embodiment of the invention, the Moveable Housing Assembly, containing the terminal end of a stationary optical path, is adjusted to the eye level (line of sight) of the user by means of a vertically operated fluid, pneumatic, or electro-mechanical lift device(s). The Moveable Housing Assembly may be moved to varying vertical positions under system control to acquire additional biometric information of user for user identification and health screening purposes.

Embodiment Including Moveable Covers

A further embodiment includes moveable covers attached to the top and bottom sides of the Moveable Housing Assembly like, but not limited to, a tambour roll-up cover allowing the Moveable Housing Assembly to move in a vertical direction while provided a light eliminating cover to optical path below.

Embodiment Including Means for Accepting a Variety of Inputs

Another embodiment includes a means for accepting input from a variety of sources, analyzing, displaying and/or outputting this information on mobile devices, computers, and printers for the user or other parties that may be located in, but not limited to, pharmacy health clinics, and off-site locations, such as doctor offices, corporate medical officers, and medical, and insurance companies.

Various Alternative Embodiments

Further embodiments include a wall unit, a seated unit, and a wall unit placed within a larger enclosure for venues such as malls, airports and other high traffic installations.

Wheel Chair Accessibility

A further embodiment allows wheel chair accessibility and a combination of user input devices including, but not limited to, voice recognition to assist these users and others with disabilities or limited movement or dexterity.

Account Creation

In one embodiment, user may create an account that stores data from previous screenings, organizes data in useful and easy to read displays, illustrates data and health trends, and predicts points of inflection of pending health issues. Returning account members may also go directly to screenings if health status has not changed since last health status input.

Further Questions Using AI, Based on Screening Results

Another embodiment utilizes algorithms and AI to ask additional questions based upon screening results and user input; recommend additional screenings based upon this information; and recommend when screenings should be repeated. This information may be displayed while user is receiving their screening results, communicated to users via smart phones, email, or recorded phone messages.

Two Fixed Distance Optical Paths

One embodiment of the current inventions includes two fixed distance optical paths. One optical path provides distance visual acuity screening and the other optical path allows back-of-the eye health assessment. Both optical paths are presented to the user at their individual eye level through a Moveable Housing Assembly. The preferable distance vision optical path ranges from 3 to 4 meters while the near, central and other vision screenings are presented on the User-Facing Monitor at a preferable viewing distance of 14 to 18 inches.

Vision Screening

In another embodiment the current inventions possess an algorithm that randomly generates alpha-numeric symbols or graphics in specific directions such as up, down, left and right and of a specific size correlated to various acuity screenings such as 20/10, 20/20, 20/30, etc. The user inputs into the system either by touch screen, voice recognition, or bodily gestor such as hand, eye, or head movement their responses to the orientation of the displayed symbols or their perception of the displayed graphics. Another algorithm based upon the number of correct user responses determines whether or not a user is able to see at a specified level of acuity, or as in the case of central vision, contrast sensitivity, color blindness and other vision screenings, the user is experiencing a visual problem related to their ocular health and eye function.

Blood Pressure Measurement

A further embodiment of the inventions includes a device, such as a blood pressure cuff, or an array of sensors and devices to measure blood pressure of the user to indicate the possibility of a condition known as hypertension. The obtained blood pressure reading is processed through an algorithmic function to determine the possible effects and correlation of hypertension on a user's vision, ocular health, heart disease, diabetes condition or risk, and other health conditions based upon a variety of measured biometric parameters. The user may also manually enter their blood pressure in order to achieve these same results. The presence of hypertension may also be obtained, through the system's back of the eye assessment, (posterior eye assessment).

Body Mass Index Assessment

Another embodiment of the present inventions assesses a user's Body Mass Index (BMI) by utilizing input of their weight and height manually, or by inputting weight manually and (1) utilizing an algorithm that determines a user's height based upon the input of their eye level, taking into consideration their age, gender, and ethnicity or (2) utilizing sensors and devices, such as acoustic and infra-red sensors to determine user top of head and therefore their height. Through yet another algorithm, the system provides the user with possible correlation of their BMI to current heart health, vision and ocular system, diabetes or risk of diabetes, and the likelihood of having an impact on any one or more of these health conditions in the future.

Addendum

System in which selection of screenings, health information, and user-selectable choices appearing on unit navigation Screen is optimized for each unit location by offering different combinations of these over a period of time and iterating on these that produce the greatest usage and user traffic for a specific unit thereby best serving the specific health needs of the user base and sponsoring advertisers.

The highest rated array of screenings, health information, and user-selectable choices appearing on a unit navigation screen may then be used as an initial home navigation screen when new units are placed in locations with similar demographic and other relevant parameters.

Another aspect of the inventions is to provide users with the percent of previous users who found system generated recommendations helpful, for example "see an eye-care professional, arrange a lab test. To acquire this information, unit will email survey to users or allow returning users to enter their comments on the present inventions or some similar means of obtaining user feedback.

Another aspect of the inventions is to offer a variety of health apps that may be purchased by the user at the unit through one or more payment options such as credit card, PayPal, smartphone payment apps, etc. User can receive health apps at a reduced cost or free for being a member of the network of present invention. Loading health apps onto user phone can be accomplished using means such as "Bump" technology or similar means of direct transfer from present inventions to user's smart device, such as a smart phone, or by user downloading from company's website or website of another entity.

Other implementations of the present inventions may include and/or involve features to allow user's insurance company, employer, or other entity to request a specific health screening, informational survey, or added question(s) to be completed by the user at the unit site. The added question(s) also can be prompted by user's previous responses to questions provided on the unit. Various aspects of the present innovations will provide a means for these requests to be billed to and paid by requesting entity.

In still other implementations of the present inventions, advertiser(s), sponsor(s), or entity(ies) may be configured to insert additional question(s) in the series of questions to be answered by the user based on previous user responses. In such implementations, the present innovations provide means for these requests to be realized as well as monetized or otherwise value add, such as billed to and paid by a requesting advertiser or sponsor.

DETAILED DESCRIPTION OF ILLUSTRATIVE IMPLEMENTATIONS

Although certain illustrative implementations and examples are disclosed below, inventive subject matter extends beyond the specifically disclosed embodiments to other alternative embodiments and/or uses and to modifications and equivalents thereof. Thus, the scope of the inventive disclosure is not limited by any of the particular embodiments described below. For example, in any system, method or process disclosed herein, the parts, acts or operations of the system, method or process may be performed in any suitable arrangement and/or sequence and are not necessarily limited to any particular disclosed implementations. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 2:
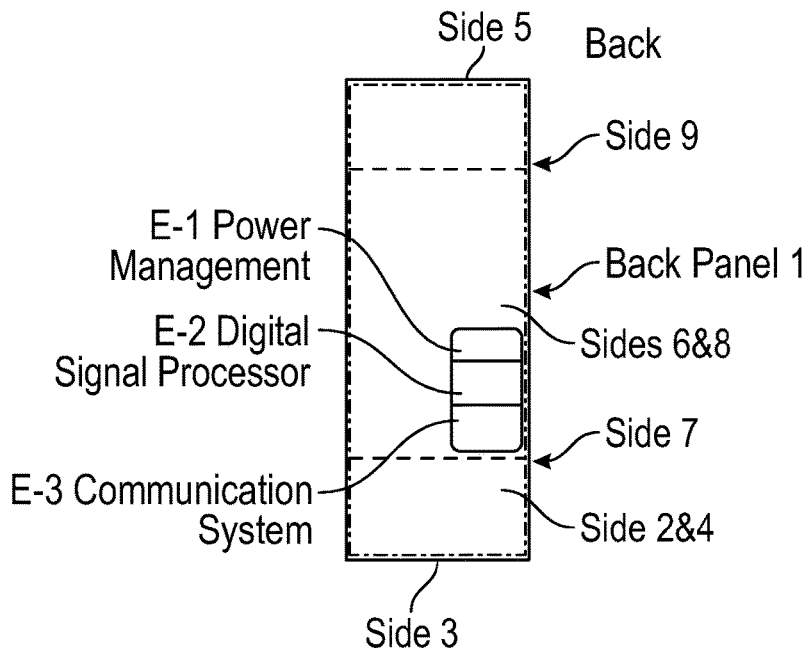

FIG. 1 represents the front view of Optical Chamber Assembly A-1 comprised of back panel 1 and outer sides 2, 3, 4, and 5 and inner sides 6, 7, 8, and 9. 2 is the outer left side attached vertically to back panel 1. 3 is the outer bottom side attached vertically to back panel 1. 4 is the outer right side attached vertically to back panel 1. 5 is the outer top side attached vertically to back panel 1. 6 is the inner left side attached vertically to back panel 1. 7 is the inner bottom side attached vertically to back panel 1. 8 is inner right side attached vertically to back panel 1. 9 is inner top side attached vertically to back panel 1. Within the boundary of inner sides 6, 7, 8, and 9 is created space for electronic components such as, but not limited to, power management devices E-1, digital signal Processor E-2, and a state-of-the-art communication system providing access to the internet E-3. FIG. 2 illustrates right side view of the Optical Chamber Assembly A-1 with components described above.

FIG. 3 illustrates the placement of mirrors 10, 11, 12, and 13 in the upper left, lower left, lower right, and upper right corners, respectively, of Optical Chamber Assembly A-1. 10 is upper left mirror. 11 is lower left mirror. 12 is lower right mirror. 13 is upper right mirror. In the preferred embodiment these mirrors will be placed at a 45 degree angle relative to the sides of their respective corners. FIG. 4 depicts the right side view of FIG. 3 and shows the back panel 1 upon which the above components are mounted.

FIG. 5 shows the addition of a User-Facing Mirror 14 and a Downward Facing Monitor E-4 placed between Outer Side 2 and Inner Side 6 of the Optical Chamber Assembly A-1. In some such implementations, User-Facing Mirror 14 may be positioned facing towards the front at a 45 degree angle relative to the horizontal as seen in FIG. 6. Downward Facing Monitor E-4 is placed parallel to the horizontal as seen in FIG. 5 and FIG. 6.

FIG. 7 and FIG. 8 illustrate an optical path, a, comprised of a between the Downward Facing Monitor E-4 and Mirror 11, b between Mirror 11 and Mirror 12, c between Mirror 12 and Mirror 13, d between Mirror 13 and Mirror 10, e between Mirror 10 and User-Facing Mirror 14, and f between User-Facing Mirror 14 and a person's eyes looking at User-Facing Mirror 14. The length of optical path a through f in a preferred embodiment approximates 9 to 11 feet to prevent accommodation. Accommodation of a user's eyes occurs when the optics of the eye adjust to keep an object in focus on the retina as its distance from the eye varies. An optical path in this preferred embodiment will keep the eyes of the user automatically focused for distance viewing and thus for distance acuity assessment. Optical path a through f is arranged such that an image displayed on Downward Facing Monitor E-4 will reflect in each Mirror 11, 12, 13, 10, and User-Facing Mirror 14, and be visible to a person looking towards User-Facing Mirror 14. Among the many possible images displayed on Downward Facing Monitor E-4 is the letter "C"—often referred to as a "Landolt C" used in vision acuity research and assessment. The "Landolt C" is randomly rotated with the opening of the "C" facing to the right, left, up or down. A person's distance vision acuity can be determined using an algorithm based upon how many times he/she identifies the correct orientation of the displayed "Landolt C" on Downward Facing Monitor E-4 and reflected on Mirrors 11, 12, 13, 10, and User-Facing Mirror 14.

A feature of present inventions is to conveniently provide health and vision screenings to persons of varied heights, representing a wide range of ages. In order to perform a distance acuity assessment, User-Facing Mirror 14 should be positioned at a user's eye level while maintaining a constant Optical Path a, b, c, d, e, and f in order that the image displayed on Downward Facing Monitor E-4 remains a constant and consistent size when viewed by the user on User-Facing Mirror 14. This is accomplished by positioning User-Facing Mirror 14 directly above Downward Facing Monitor E-4 and enclosing both in a Moveable Housing Assembly A-2. As Moveable Housing Assembly A-2 moves in a vertical direction, optical paths a and e will either shorten or lengthen the same amount and thus maintaining a constant Optical Path a, b, c, d, e, and f.

An alternative embodiment to the mirror arrangement shown, for example, in FIGS. 3-8 (i.e., having mirrors arrange in the X-axis—given a conventional X-Y-Z axis orientation), namely an alternative embodiment that involves a different and innovative placement of mirrors in the Z-axis is set forth further below in connection with FIGS. 87A-90.

FIG. 9, FIG. 10, FIG. 11, and FIG. 12 illustrate the housing component of the Moveable Housing Assembly A-2. Cut-Out 21 is performed on Side 19 (top) of the of the housing, Cut-Out 22 is performed on Side 20 (bottom) of housing, and Cut-Out 23 is performed on Side 16 (front) of housing. A rectangle, among many other possible shapes, is shown as the preferred shape of Cut-Outs 21, 22, and 23.

FIG. 13, FIG. 14, FIG. 15, and FIG. 16 show the placement of User-Facing Mirror 14 in the housing component of the Moveable Housing Assembly A-2. Cut-Out 21 allows an image reflected from Mirror 10 along optical path e to reflect on User-Facing Mirror 14, and through Cut-Out 23 along optical path f and thus seen by user.

FIG. 17, FIG. 18, FIG. 19, and FIG. 20 show the placement of Downward Facing Monitor E-4 in the housing component of the Moveable Housing Assembly A-2 and along with User-Facing Mirror 14, complete the Moveable Housing Assembly A-2. Cut-Out 22 allows an image displayed on Downward Facing Monitor E-4 to reflect on Mirror 11 along optical path a and same image reflected to Mirror 12, 13, 10 and User-Facing Mirror 14, thus completing Optical Path a, b, c, d, e and f.

Figure 26:
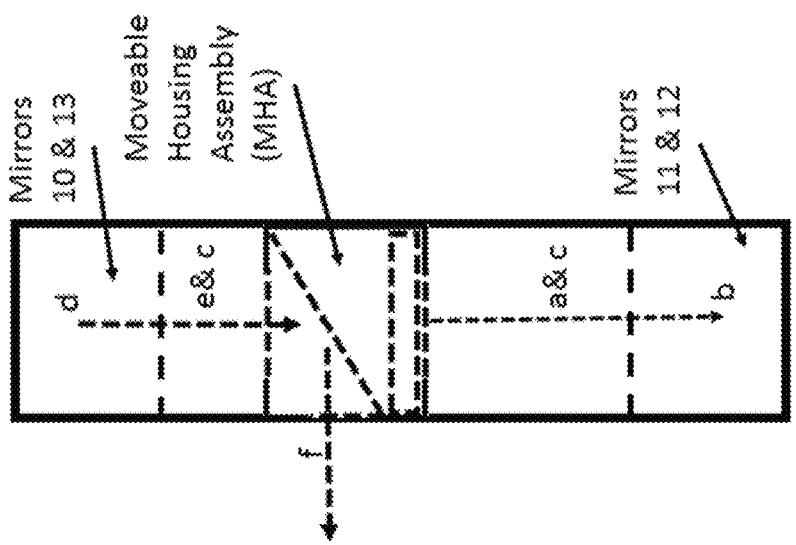
Figure 25:
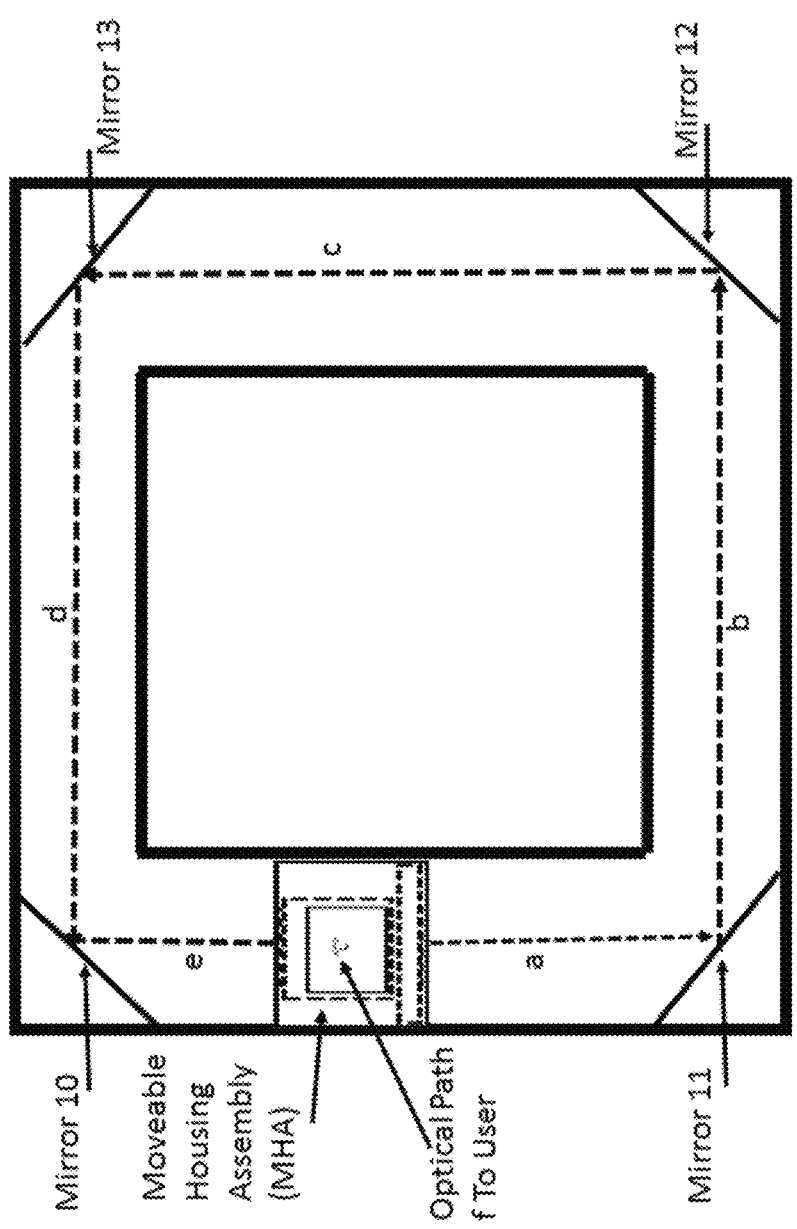
Figure 33:
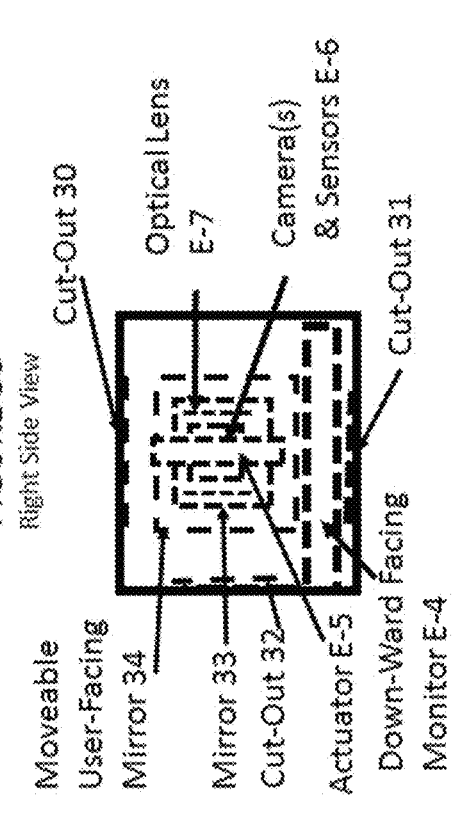
Figure 34:
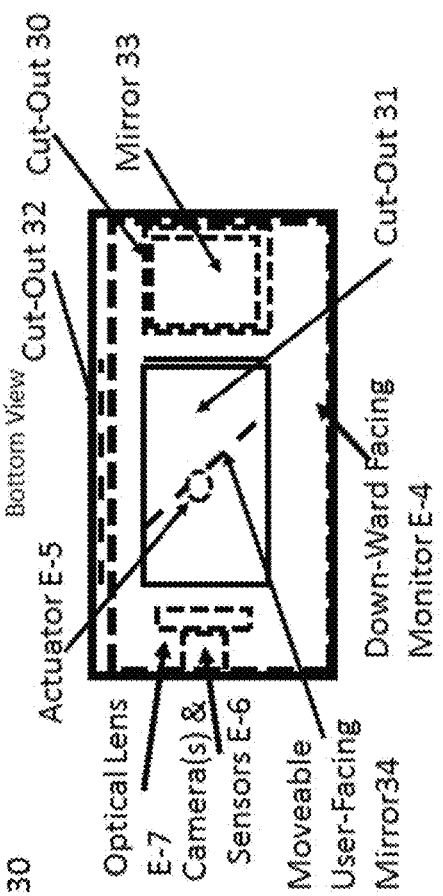
Figure 31:
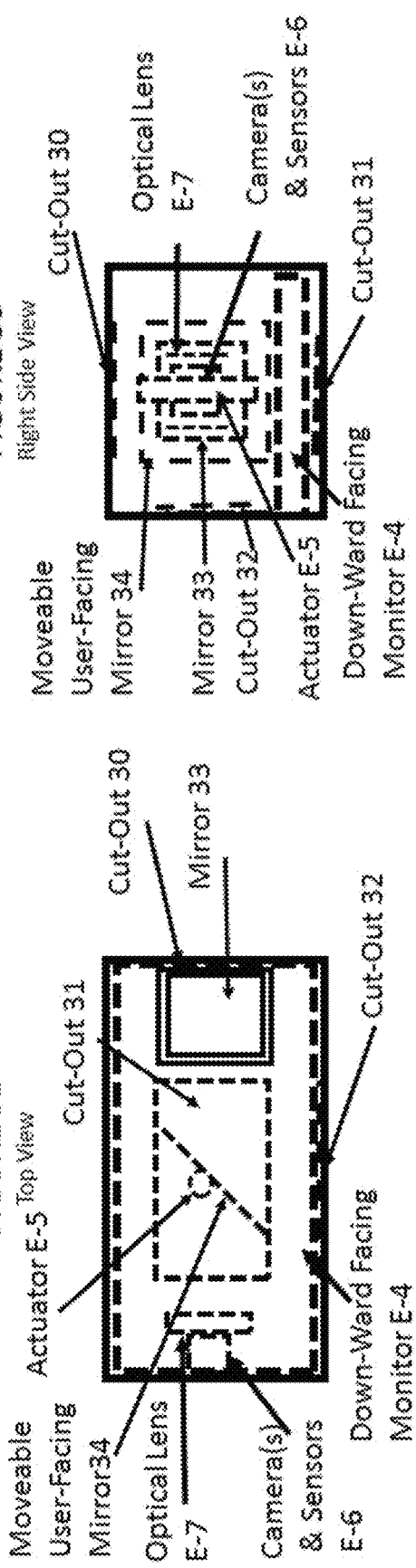
Figure 32:
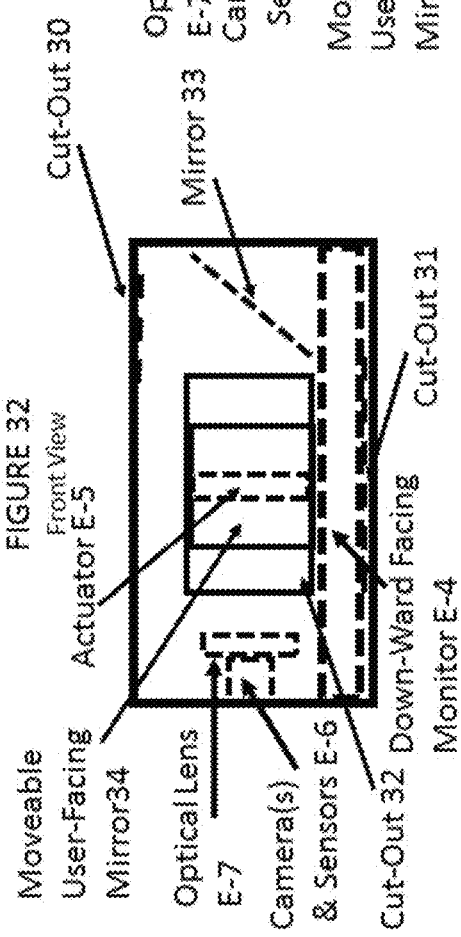
Figure 43:
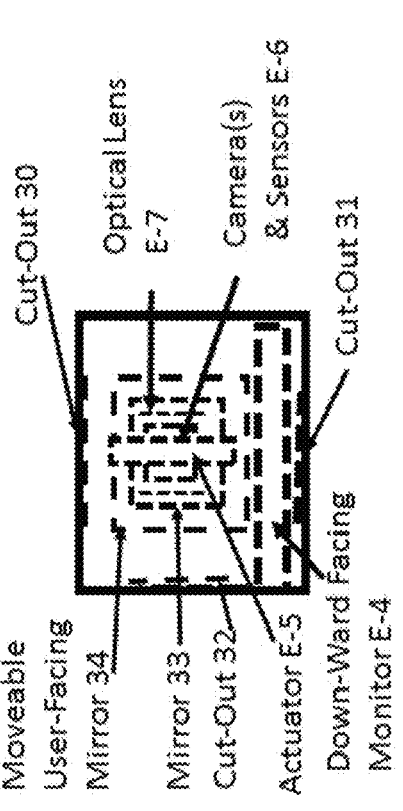
Figure 44:
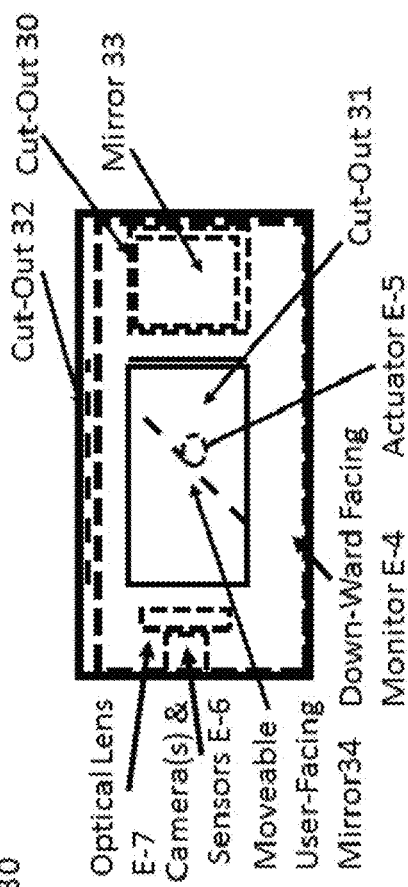
Figure 41:
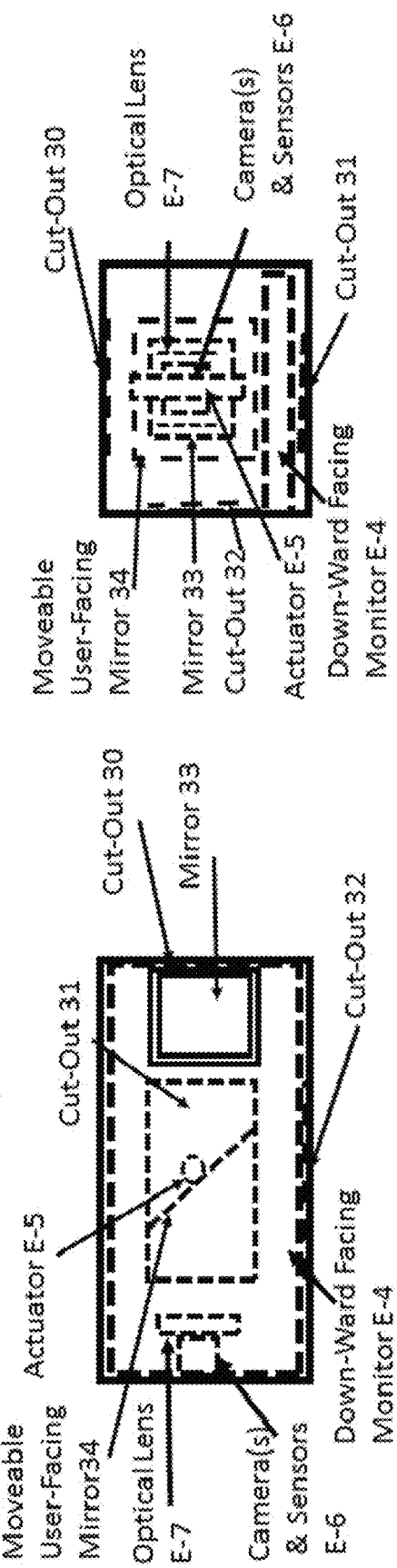
Figure 42:
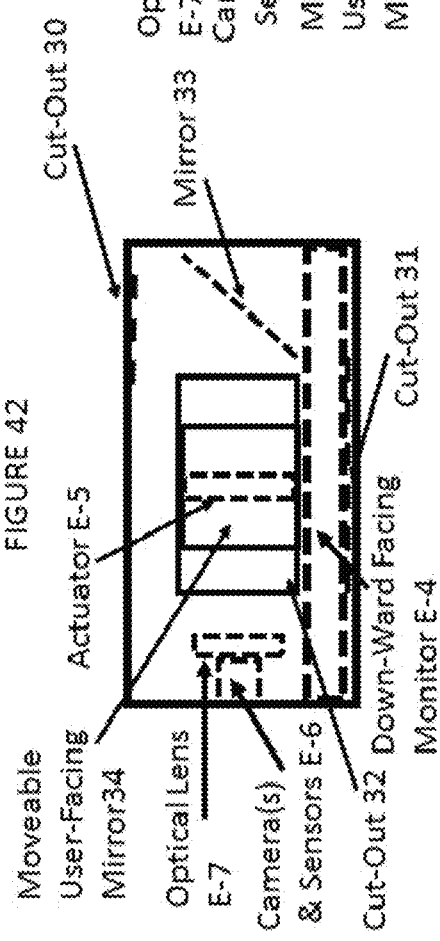
Figure 47:
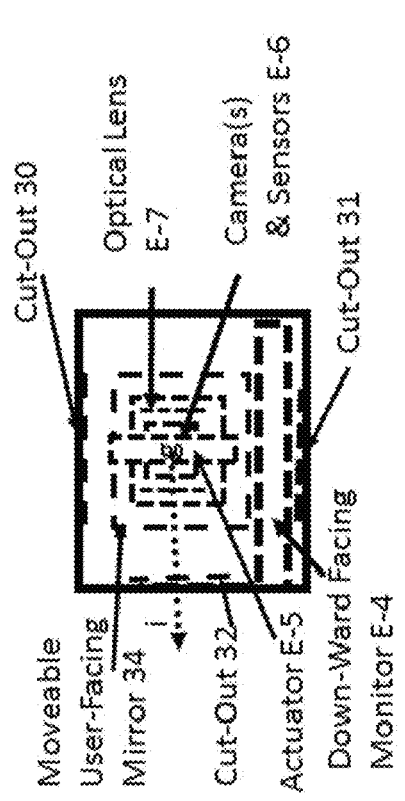
Figure 48:
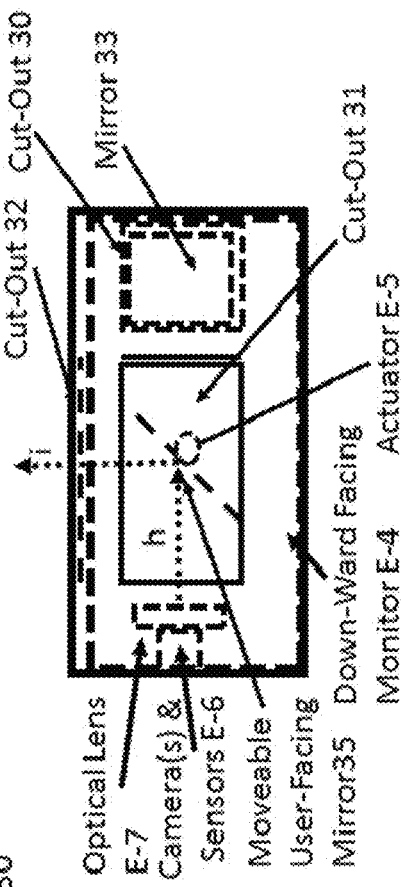
Figure 45:
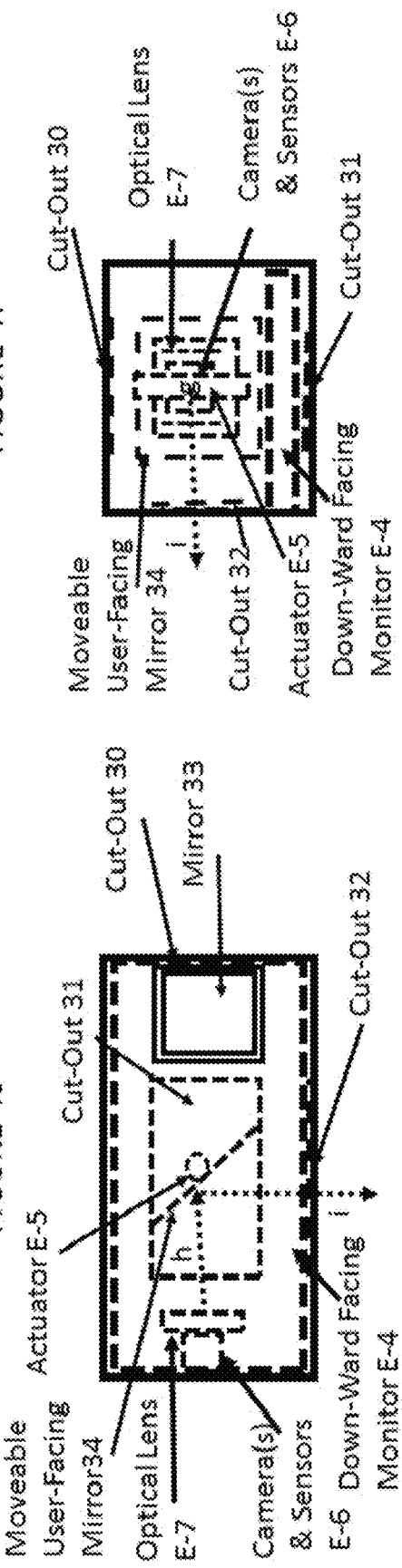
Figure 46:
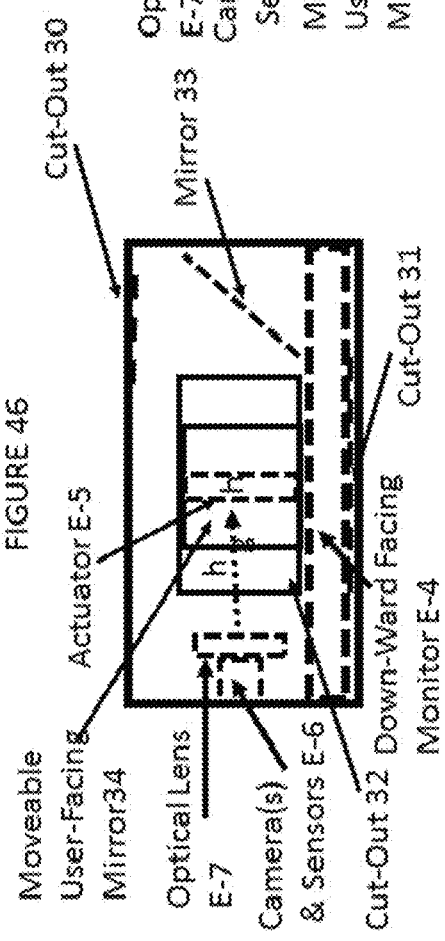

The displayed "C" follows optical path a, b, c, d, and e and is displayed on User-Facing Mirror 14 through Cut-Out 23 in the Moveable Housing Assembly A-2 in FIG. 22. FIG. 21 illustrates the top view, FIG. 23 illustrates the right side view and FIG. 24 illustrates the bottom side of the Moveable Housing Assembly A-2. Cut-Out 21 is located on the top surface of A-2. User-facing mirror is positioned directly below cut-out 21 at a 45°. As shown in FIG. 23, an image is allowed to be displayed on Downward Facing Monitor E-4 to be seen by user through Cut-Out 22. A displayed "C" on Downward Facing Monitor E-4 is displayed through Cut-Out 22. FIG. 26 illustrates optical path segment f reflecting off User-Facing Mirror 14 to the user. FIG. 25 and FIG. 26 provides a view of the image "C" reflecting off User-Facing Mirror 14 and the optical path which it follows emanating from Downward Facing Monitor E-4 and completing at user's eyes along optical path f.

Certain models of present invention, particularly initial models designated for the corporate segment of the market, will also have technology to scan the back of the eye of a user and artificial intelligence, AI, to interpret the scans. Acquisition of back-of-the-eye images will be accomplished through devices such as cameras, video cameras, lenses and other electro-optical devices that may use both visible and invisible light spectrums. To provide room for these devices and optics, a Moveable Housing Assembly II is depicted in, FIG. 27, FIG. 28, FIG. 29 and FIG. 30. Images displayed on Downward Facing Monitor E-4 now enter Moveable Housing Assembly II (MHAII) through Cut-Out 30 on top Side 28 of MHAII in FIG. 27, FIG. 28, FIG. 29 and FIG. 30. Cut-Out 30 may be placed in various positions on top Side 28. Cut-Outs 31 and 32 provide visible access to Downward Facing Monitor E-4 and Moveable User-Facing Mirror 34 (see FIG. 31, FIG. 32, FIG. 33 and FIG. 34), respectively.

FIG. 31, FIG. 32, FIG. 33 and FIG. 34 illustrate User-Facing Mirror 34 in distance vision assessment mode.

FIG. 38 illustrates the bottom side of the Moveable Housing Assembly II, A-3. FIG. 35, FIG. 36, and FIG. 37 illustrate the other three sides of the Moveable Housing Assembly II, A-3. FIG. 35 and FIG. 37 show the top and right side view of Moveable Housing Assembly II, A-3, illustrating actuator E-5 capable of changing the position of moveable User-Facing Mirror 34 from "distant" vision screening to 'back-of-the-eye' assessment mode. Symbols on graphics displayed on the surface of Downward Facing Monitor E-4 propagate through optical path a, b, c, d, and e' and enter Moveable Housing Assembly II, A-3, through Cut-Out 30, reflecting on mirror 33 and Moveable User-Facing Mirror 34, at which time it can be seen by user. A displayed "C" on Downward Facing Monitor E-4 is displayed through Cut-Out 31. The displayed "C" follows optical path a, b, c, d, e' and f' (FIG. 39 and FIG. 40) and is displayed on User-Facing Mirror 34 (in distance vision assessment mode) through Cut-Out 32 in the Moveable Housing Assembly II, A-3 in FIG. 36.

FIG. 39 reveals Mirror 10 moved to the right (Mirror 10') to allow optical path segment e' to enter Moveable Hosing Assembly II through Cut-Out 30 and reflecting off Mirror 33. FIG. 40 provides a side view of the image "C" reflecting off User-Facing Mirror 34 and the optical path which it follows completing at user's eyes along optical path g'.

FIG. 41, FIG. 42, FIG. 43 and FIG. 44 illustrate Moveable User-Facing Mirror 34 within Moveable Housing Assembly II, A-3 positioned in eye assessment mode and facing camera and sensors E-6 and Optical Lenses E-7. Moveable User-Facing Mirror 34 is moved from distance vision screening to eye assessment mode by Actuator E-5.

FIG. 45, FIG. 46, FIG. 47 and FIG. 48 illustrate Moveable User-Facing Mirror 34 within Moveable Housing Assembly II, A-3, positioned in eye assessment mode and facing camera and sensors E-6 and Optical Lenses E-7. User-Facing Mirror 34 is moved from distance vision screening to eye assessment mode by Actuator E-5 creating optical paths h and i. Camera and sensors E-6 and Optical Lenses E-7 may be stationary or moveable to acquire back-of-the-eye images of user through optical paths h and i. Actuator E-5 may move Moveable User-Facing Mirror 24 from distance vision assessment mode to eye assessment mode and back to distance vision assessment mode between changes in orientation of image "C" used in distance vision assessment.

FIG. 49 and FIG. 50 depict a Lift Device E-8 and Guide Rail Assembly E-9 between the inner 6 and outer 2 sides of Optical Housing Assembly A-1. Lift Device E-8 is attached to Moveable Housing Assemblies A-2 or A-3 and provides vertical motion to Moveable Housing Assemblies A-2 and A-3 allowing positioning at a user's eye level. Lift Device E-8 may also provide a translational movement in a horizontal direction within the confines of sides 2 and 6 to assist aligning Moveable Housing Assemblies A-2 and A-3 with user's eyes for either distance vision screening or back-of-the-eye assessment.

Additional details regarding innovation of the alternative embodiment of FIGS. 87A-90, involving arrangement of Mirrors 10, 11, 12, and 13, Lift Device E-4, and Optical Chamber Assembly A-1 are set further below in connection with the description of FIGS. 87A-90.

FIG. 51 and FIG. 52 illustrate the placement of Optical Chamber Assembly A-1 within Outer Chamber Assembly A-4, with surrounding side panels 35, 36, 37 and 38 mounted on back panel 39.

Figure 54:
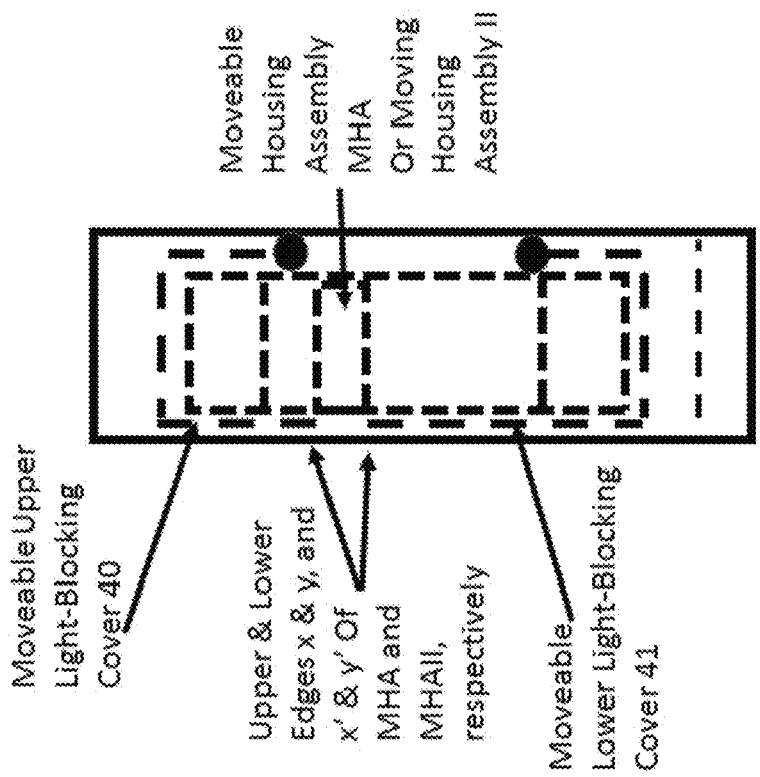
Figure 53:
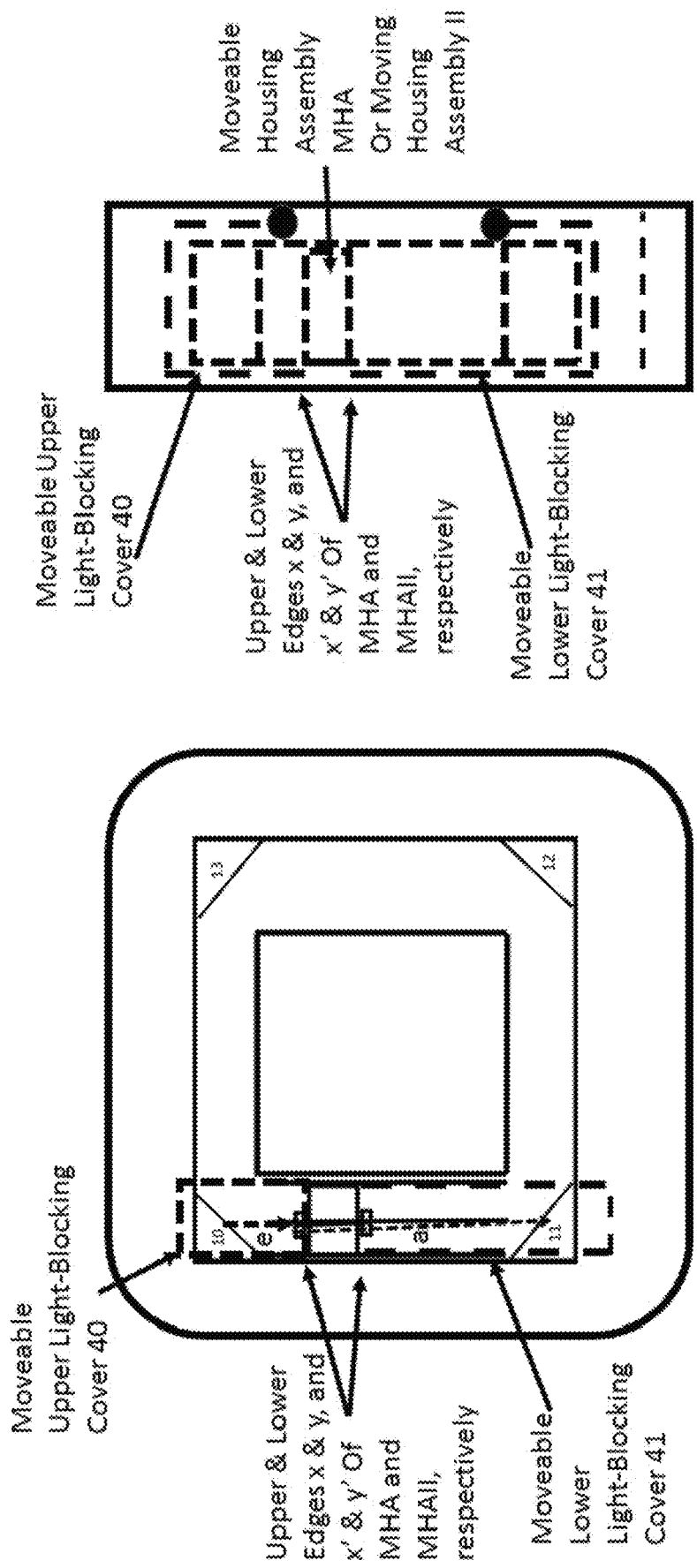

FIG. 53 and FIG. 54 illustrate the placement of Upper Moveable Light-Blocking Cover 40 and Lower Moveable Light Blocking Cover 41 between Optical Chamber Assembly A-1 and Outer Chamber Assembly A-4. Cover 40 is attached to the top of MHA or MHAII at edge x and Cover 41 attached to bottom of MHA or MHAII at edge y. As Moveable Housing Assembly descends in a vertical direction, Cover 40 covers a larger area above optical path e while Cover 41 covers a smaller area above optical path a. As Moveable Housing Assembly ascends in a vertical direction the converse is true. The preferred embodiment of Covers 40 and 41 is a tambour or tambour-like roll-up door arrangement, however, other methods may include shades and blinds, glass products that change transparency when electric current is applied, and bellows.

FIG. 55 and FIG. 56 show the placement of Sensor And Device Panels E-10, E-11, E-12, and E-13 between the Outer Chamber Assembly 36 and Optical Chamber Assembly 35. Also shown is the positioning of Large Sensors And Device Panel E-14 and User-Facing Touch-Screen Monitor E-15. These sensor panels may contain additional cameras, speakers, microphones, optical & acoustic sensors, spectrum analysis sensors (e.g. breath analysis), and other mechanical systems connected to sensors to allow enhanced and additional recording of user health and environmental data.

Figure 58:
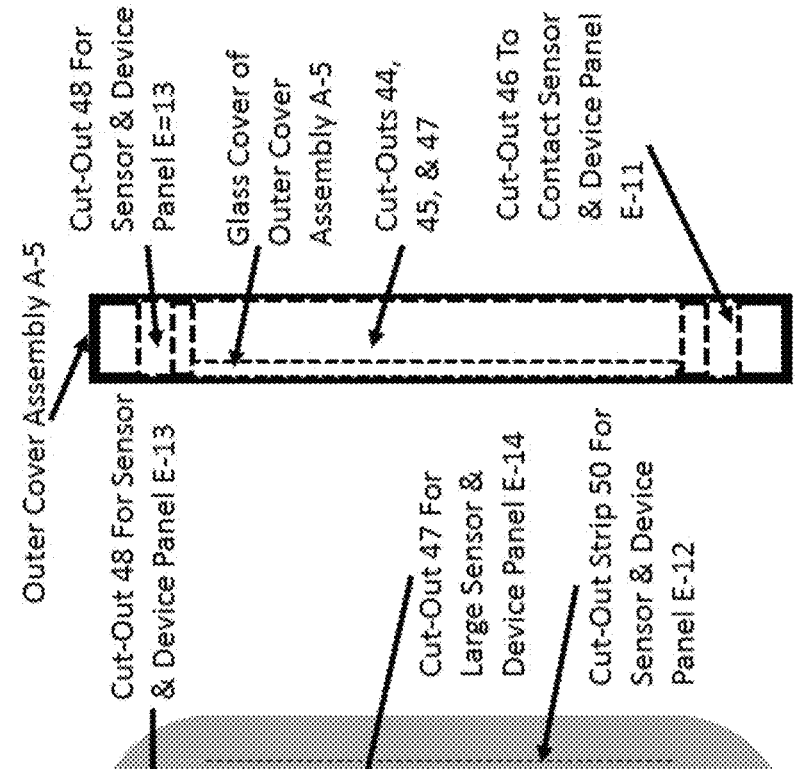
Figure 57:
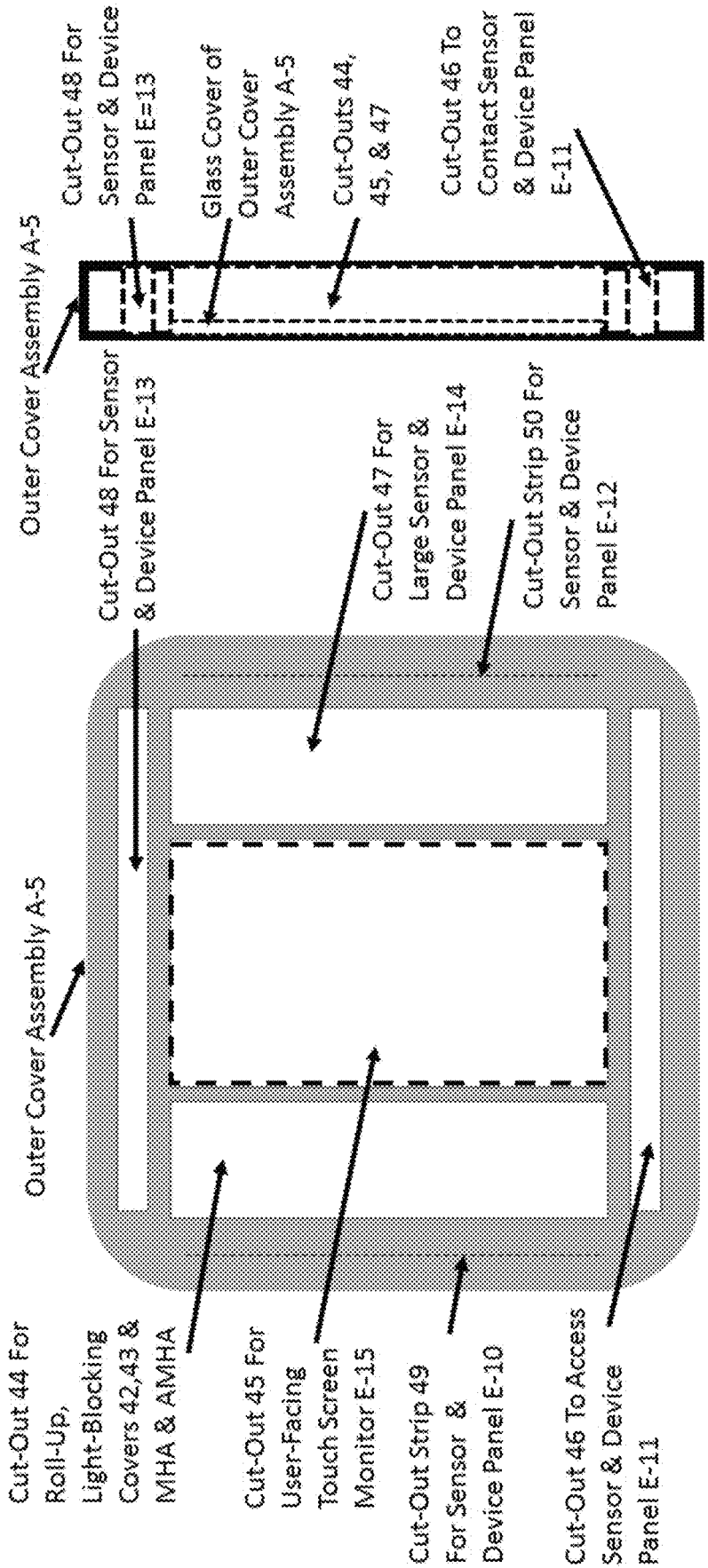
Figure 59:

FIG. 57 and FIG. 58 illustrate one of many designs for Outer Cover Assembly A-5 placed above Optical Chamber Assembly 35 and Outer Chamber Assembly 36. Cut-Out 44 provides visual access to Roll-Up, Light Blocking Covers 42 and 43 and Moveable Housing Assemblies A-2 and A-3. Cut-Out 45 provides placement for User-Facing Touch-Screen Monitor E-15. Cut-Out 46 provides user hand access to Sensor and Device Panel E-11. Cut-Outs 47, 48, 49, and 50 provide openings for Large Sensor and Device Panel E-14, and Sensor and Devices Panels E-13, E-10, and E-12, respectively. A cover similar in design to Moveable Light-Blocking Covers 40 and 41 may be placed over Large Sensor and Device Panel E-14 for symmetrical appearance, as shown in FIG. 59. In the preferred embodiment Outer Cover Assembly A-5, Optical Chamber Assembly 35, and Outer Chamber Assembly 36 are made of light weight, rigid material such as aluminum, resins, or plastics. The protective transparent covering of the Outer Cover Assembly may be made of glass, plastic, or other synthetic resin.

Figure 60:
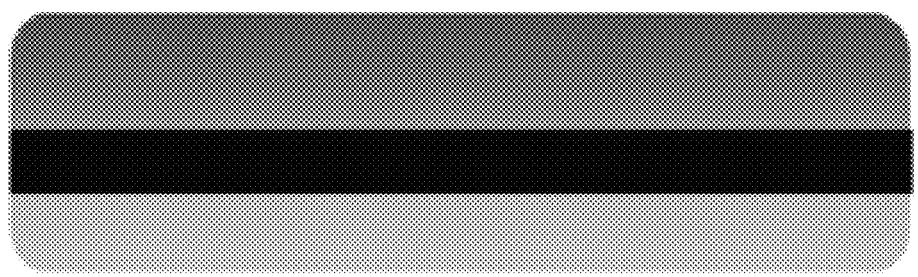

FIG. 59 and FIG. 60 illustrate an example of an illustrative unit consistent with one implementation of a complete device.

Figure 61A:
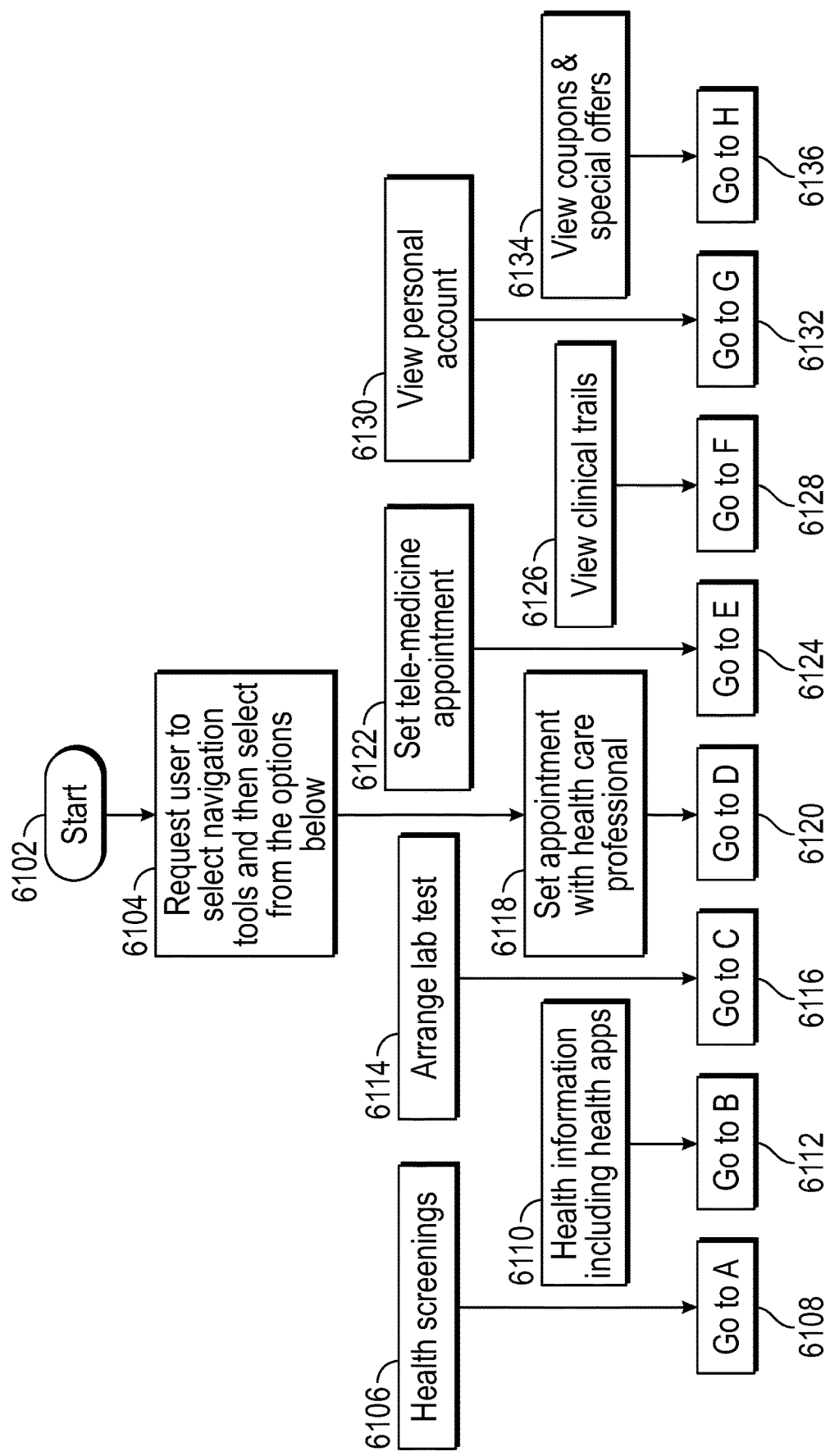
FIGS. 61A, 62-82 are illustrative flowcharts of one or more implementations consistent with aspects related to the innovations herein.
Figure 61B:
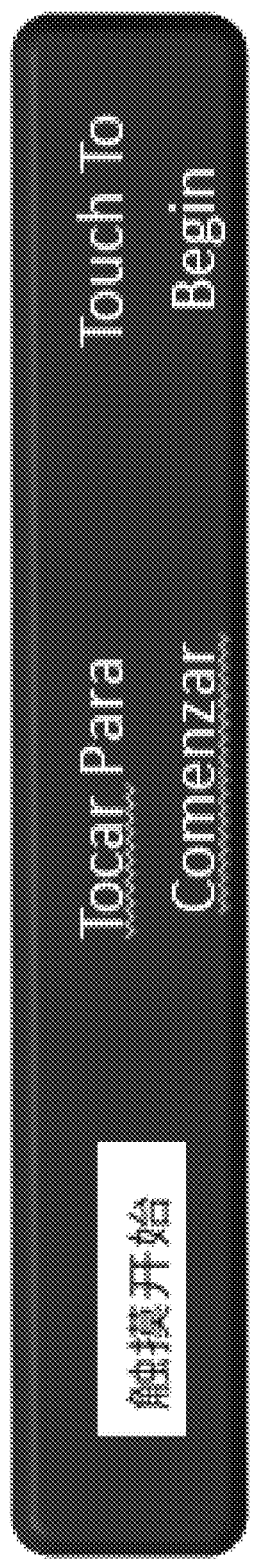
FIG. 61B is an illustrative touch screen showing a selection displayed in multiple languages consistent with aspects related to the innovations herein.

In FIG. 61A, items 6110 through 6134 are developed as if the user engages with these items on present Inventions in a specific location. For convenience, these items may be accessed through the FirstPoint Health, Inc. website and performed in a similar manner.

In FIG. 61A, 6102 is the first touch point for a user to activate and engage with the system. The user may select their preferred language from a multiple of languages such as shown in FIG. 61A. Language options will be appropriate to the country or area of the country in which inventions is placed. 6104 allows the users to select their preference for navigating and engaging with the system. A multiple of navigation choices may be offered and the ones shown here include touchscreen, voice recognition, and AI voice response. The default navigational tool may be touch screen which would always be active even though another navigation mode is selected. The user is then presented with a variety of system offerings that may include Health Screenings 6106, Health Information 6110, Arrange A Lab Test 6114, Set An Appointment With A Healthcare Professional 6118, set a Tele-Medicine Appointment 6122, View Clinical Trials 6126, View Personal Account 6130, and View Coupons And Special Offers 6134. A feature of the present inventions allows additions or subtractions to selections presented. With use of AI, the system selects those selections that meet the company's, host's, and advertiser's goals such as, but not limited to, how often a selection is used, the number of repeat users per selection, the usefulness of the data acquired from each selection, the revenue generated from a selection, increase in store traffic, etc. When user makes a selection, the system automatically goes to that selection as shown in 6101, 6112, 6116, 6120, 6124, 6128, 6132, and 6136.

Figure 62:
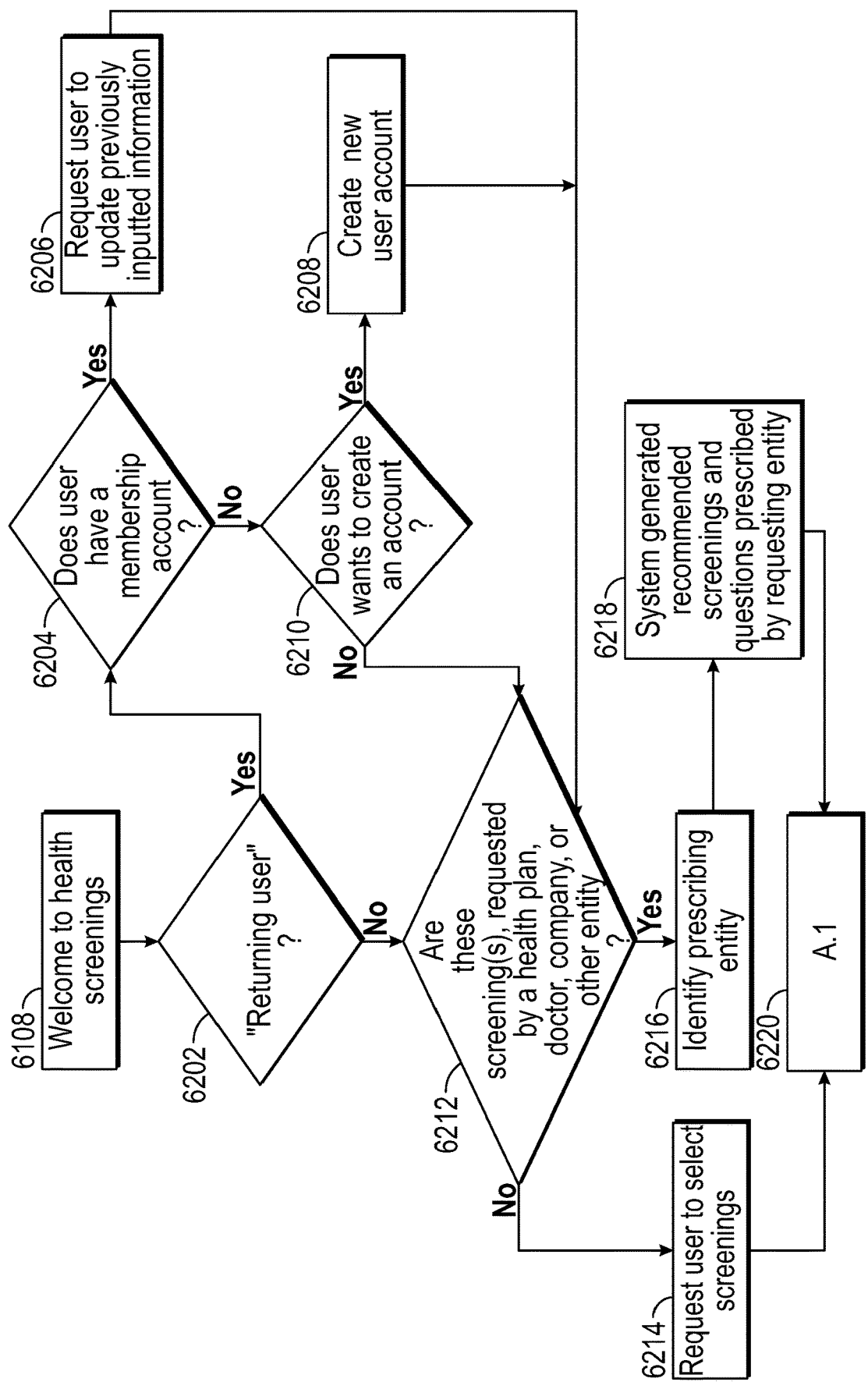

FIG. 62 illustrates the system flow when a user selects 'Health Screenings' 6106 above. 6108 welcomes a user to 'Health Screenings' followed by 6202 requesting user to identify if they are a returning user. If they are a returning user, 6204 asks user to indicate if they have a membership account. If yes, 6206 allows them to update or change information stored in their account. The information in a user account allows the system to analyze user data, present trends, and through AI predict future health outcomes based on intervention or no intervention, and potential prevention measures, if any. A user account may be updated by user input or data generated by the present invention, or through external means and devices such as wearables, health apps, etc. If the answer to 6204 is No, user is given opportunity to create an account in 6210 and 6208. A unique feature of the present inventions is to allow a health plan, doctor, company, or other entity, 6212, to prescribe one or more screenings or health information update. If screenings or requested information was from a prescribing entity, that entity is named 6216 along with entity's requested screenings or information 6218. User then is requested to select screenings, 6214. In the event the user is a first time user, the system requests their Health Screening selection(s), 6214, and proceeds, A.1, to that screening, 6220.

Figure 63:
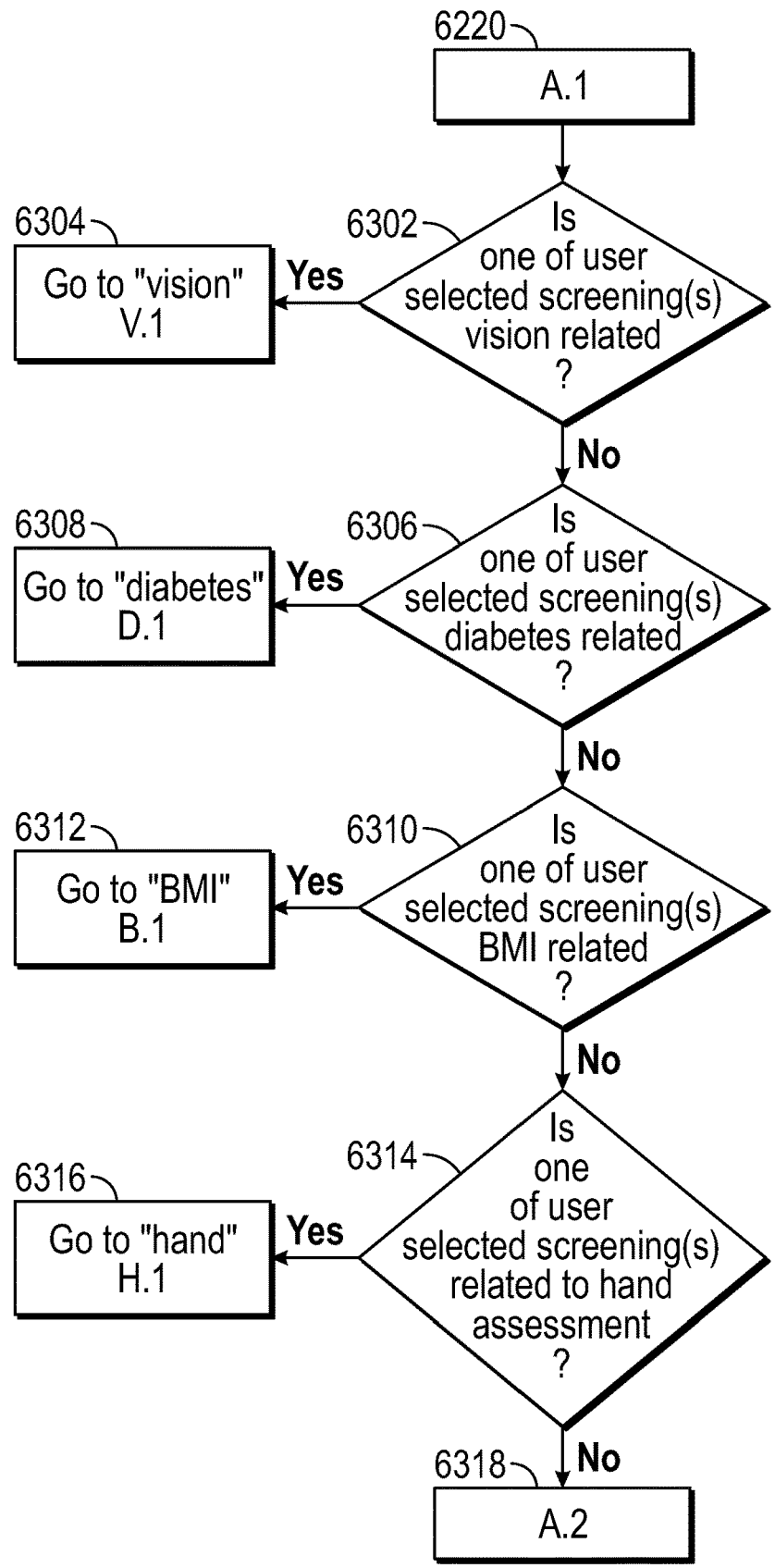
Figure 64:
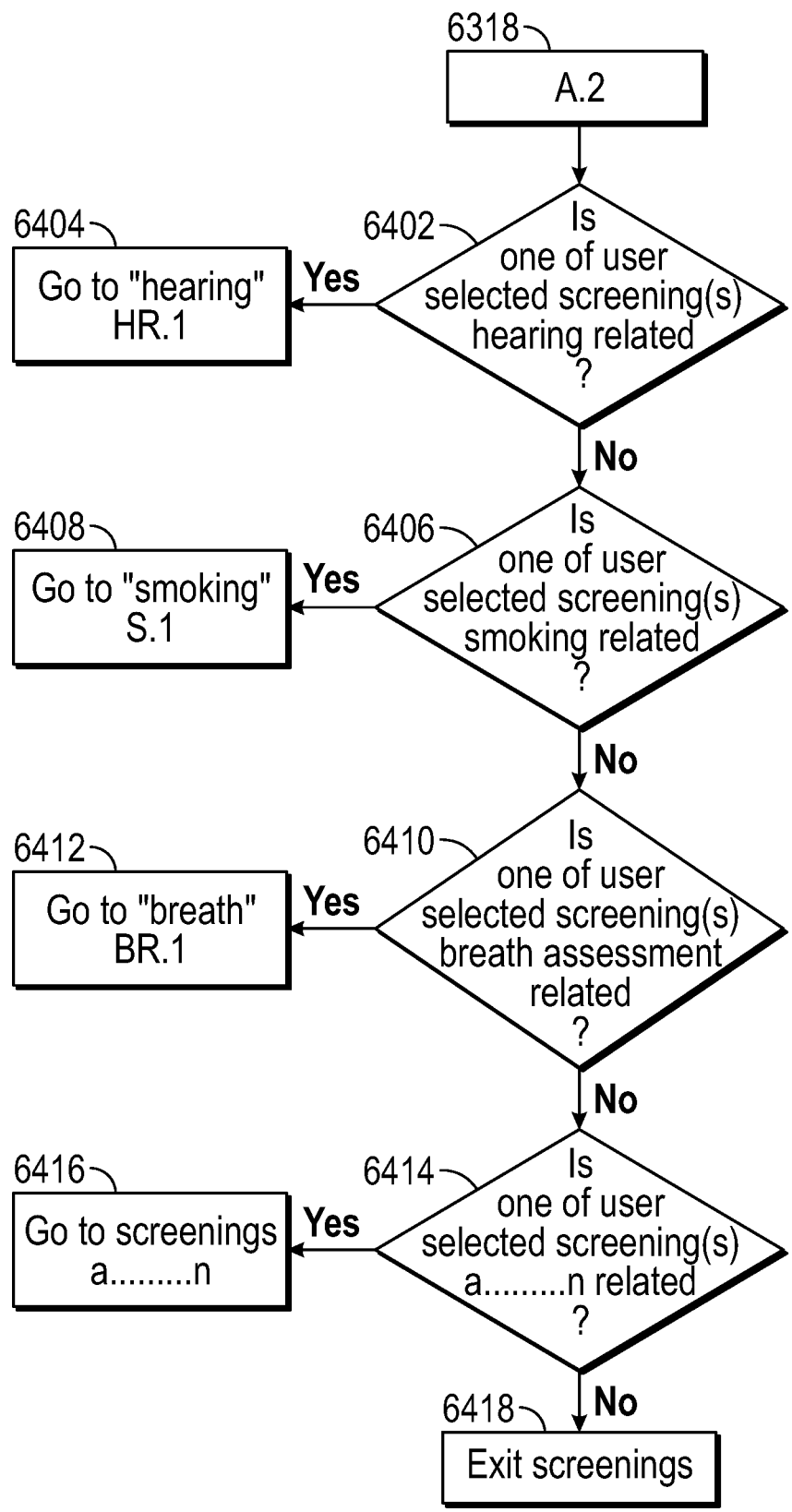

FIG. 63 and FIG. 64 illustrate the decision tree and software flow as a user selects the health screening(s) to be performed. 6302 awaits user's selection and if selected, goes to Vision Screening, 6304. In a similar fashion, 6306, 6310, 6314, 6402, 6406, 6410, and 6414, which are screenings for Diabetes, BMI, Hand Analysis, Hearing, Smoking, Breath Analysis, and Other screenings a . . . n, respectively, await selection and if selected proceed to their individual screening. 6416 allows the system to incorporate additional screenings that may include, but not limited to, assessment of anterior and posterior portions of the eye, blood pressure, pulse, heart rate, EKG, and galvanic skin response. The system's hand and skin screening and analysis is for the possible detection of skin disorders, including skin cancer, joint issues, liver problems, osteoarthritis, thyroid and hypothyroidism, anemia, lung disease and impaired oxygen levels.

Figure 65:
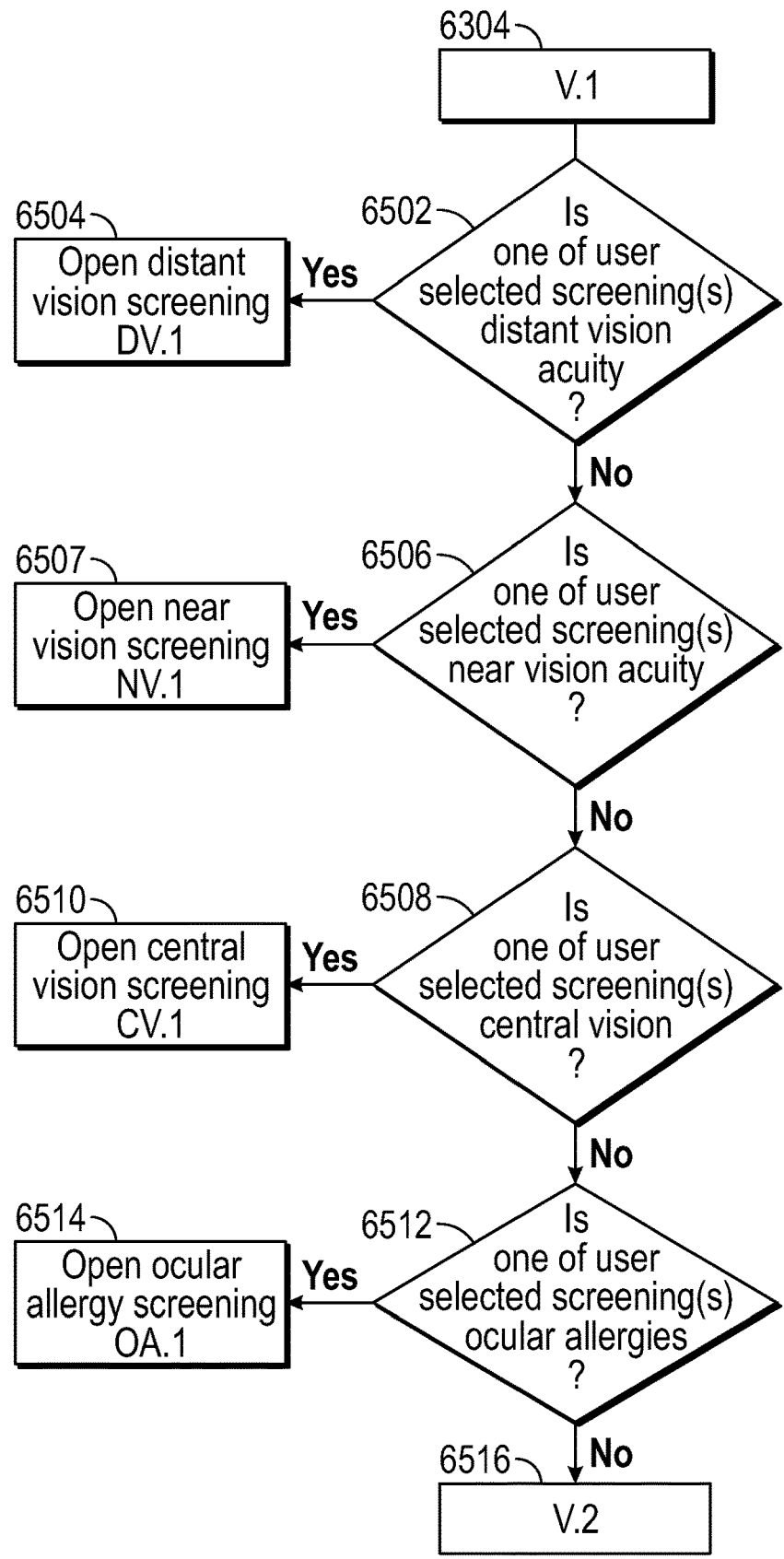
Figure 66:
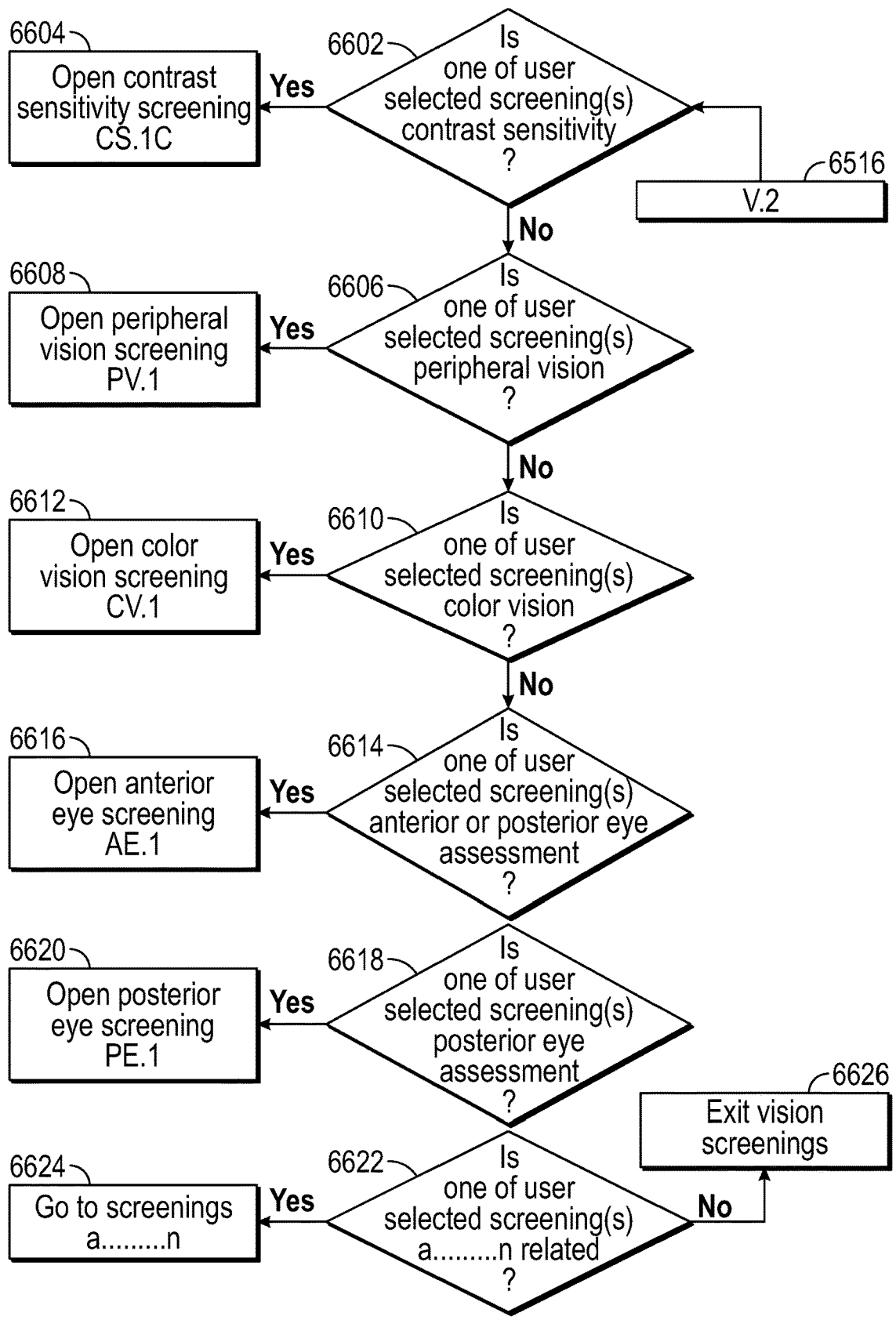

FIG. 65 and FIG. 66 illustrate the system flow if Vision Screening, 6302 is among screenings selected by the user. The user may select among Distant Vision Screening 6504, Near Vision Screening 6507, Central Vision Screening 6510, Ocular Allergy Screening 6514, Contrast Sensitivity 6604, Peripheral Vision Screening 6608, Color Vision Screening 6612, Anterior Eye Screening 6616, Posterior Eye Screening 6620, and Other Eye Screenings depicted by a through n (a . . . n) in 6624.

Figure 67:
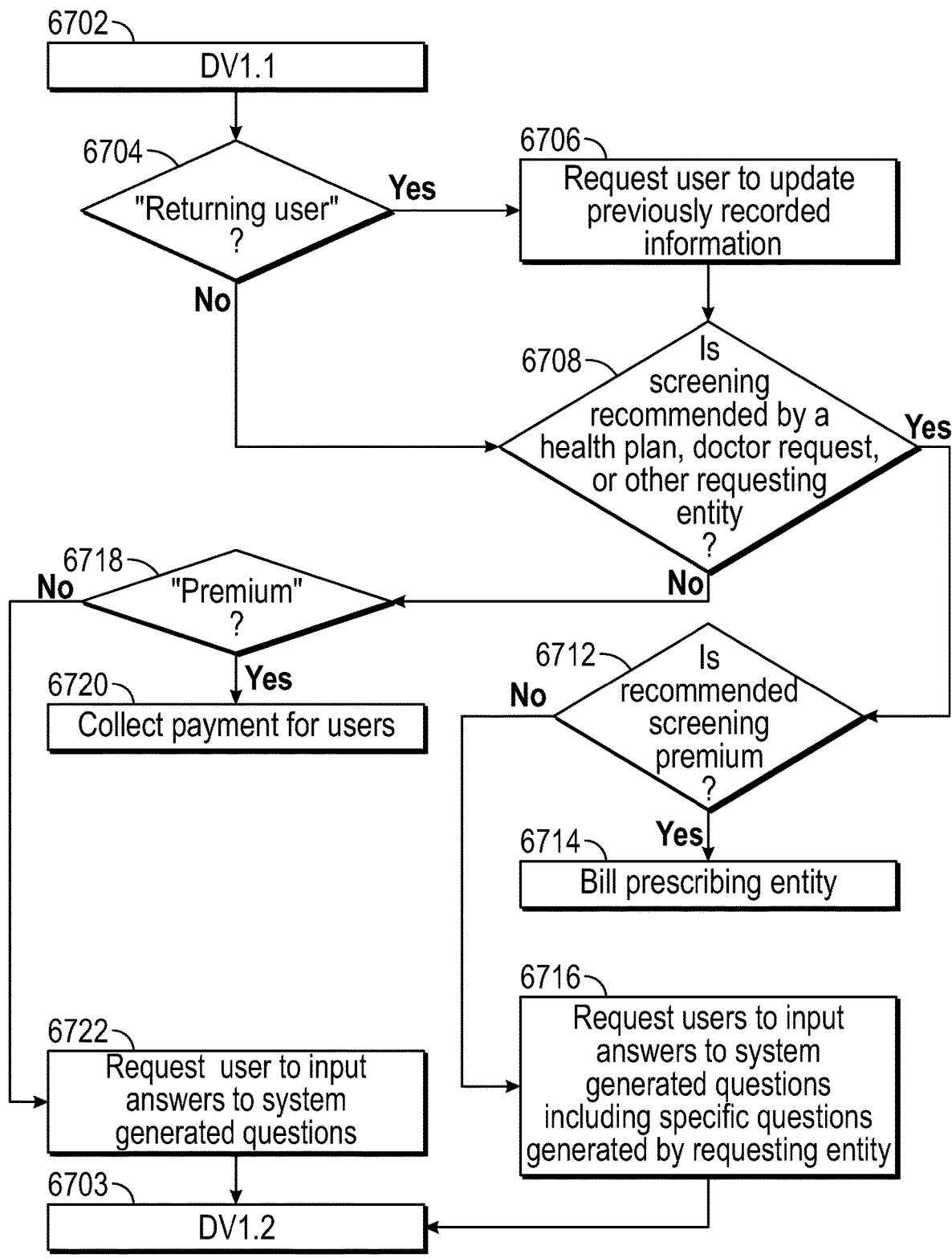

FIG. 67, like FIG. 62, provides a user the ability to identify themselves as a returning user, 6704, and if user is, offer the opportunity to update previously recorded information, 6706. The user is also able to provide input relative to screening(s) that may be recommended or requested by a health plan, doctor request, company, or other requesting entity, 6708. The present inventions may offer "free" screenings or "premium" screenings for which user will pay a fee. If the answer to 6708, as described above, is "yes" and the screening selected is a premium screening, then the prescribing entity may be billed for the screening(s), 6712 and 6714. The user may also be required by the paying entity to answer questions either generated by the present inventions or furnished by prescribing entity through the present inventions in order to receive premium screening(s). In the event that the screening(s) were not from a health plan, doctor, or other requesting entity and the screening(s) is a premium screening, user will be asked to pay for selected screening(s). The system may collect payment for screening(s) by a variety of means such as, but not limited to, use of a credit card, Paypal, smartphone payment system, FirstPoint Health Gift Card and other such payment options, 6720. Premium screening(s) paid by the user begin with requesting user to input answers to system generated questions, 6722.

Figure 68:
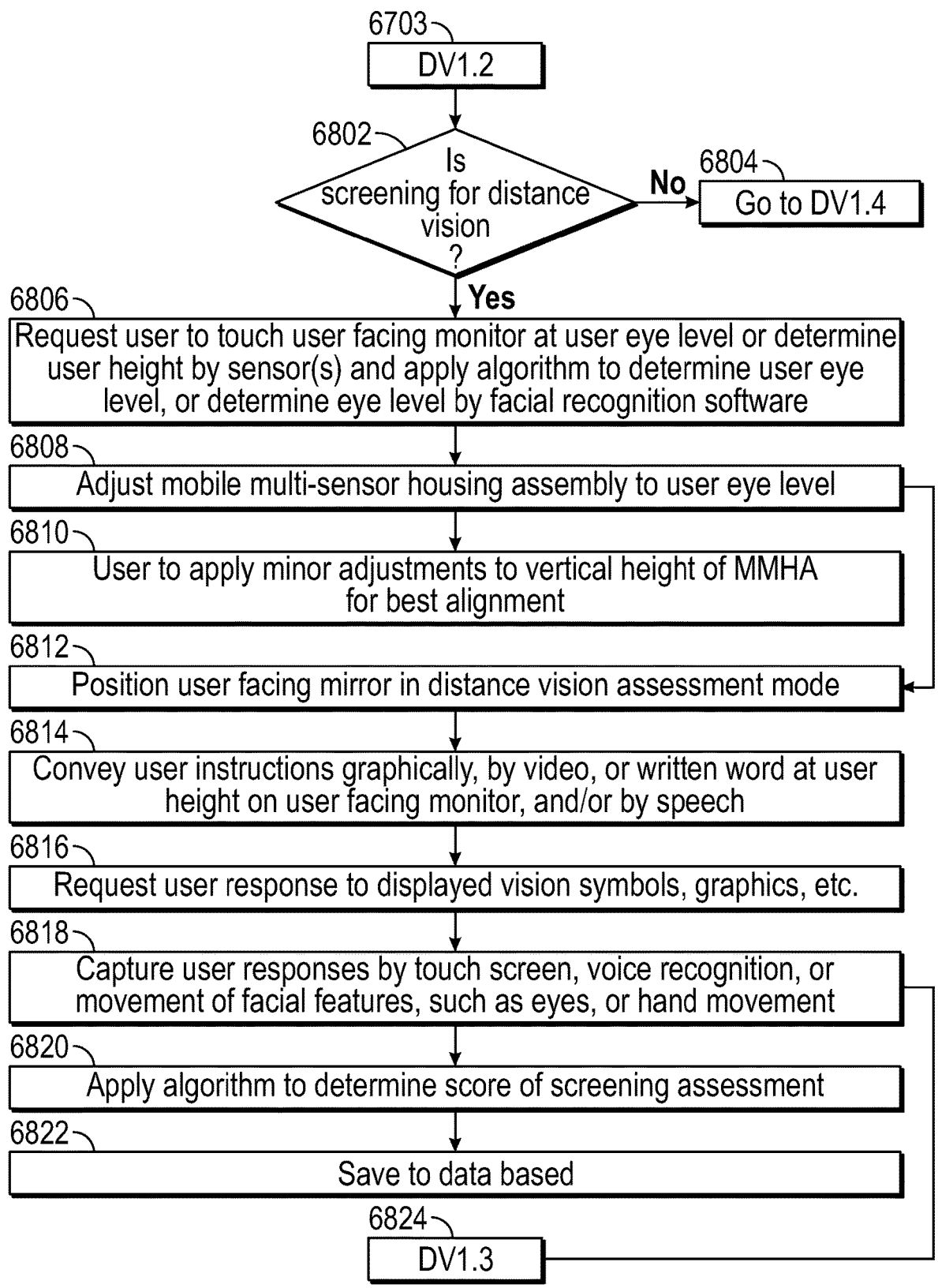

FIG. 68 depicts the screening for Distant Vision after the user has completed answering questions in either 6716 or 6722, above, for the Distant Vision screening. The system then requests user to touch the User Facing Touch Screen. Monitor, E-15, at user's eye level. Alternative methods for determining user's eye level include, but not limited to, camera(s), distance sensors, infra-red sensors, or facial recognition software, 6806. Upon receiving user eye level information, the system moves the Moveable Housing Assembly A-2 or the Moveable Housing Assembly II A-3 the appropriate distance to position either Moveable Housing Assembly at user's eye level. The user is provided the ability to make adjustments to the vertical height of either Moveable Housing Assembly, 6810, for improving the alignment to their line of sight. Prior to providing the user with a distant vision screening, the system positions the User Facing Mirror 14 or 34 in the Distant Vision Screening mode where a graphic target displayed on Downward Facing Monitor E-4 travels the optical path a, b, c, d, and e or optical path a, b, c, d, and e' and seen by the user as the graphic target reflects off User Facing Mirror 14 or 34. Another unique feature of present inventions is knowing a user's height allows the system to provide written instructions and navigation controls/buttons at the user's eye level. This feature is particularly valuable for children, wheel-chair users and those with limited dexterity. Instructions may also be provided by pre-recorded speech, 6814. The system requests user to identify a symbol or graphic, such as an alphabet letter, number, or the direction of the opening of the Letter "C" using a touch screen, voice recognition, facial or hand movement, or other means of communicating user response, 6816 and 6818. The system captures and applies algorithms to the user's response to determine a user's ability to see distant objects, 6820. System saves this data to memory for later recall when system presents screening results to the user, 6822.

Figure 69:
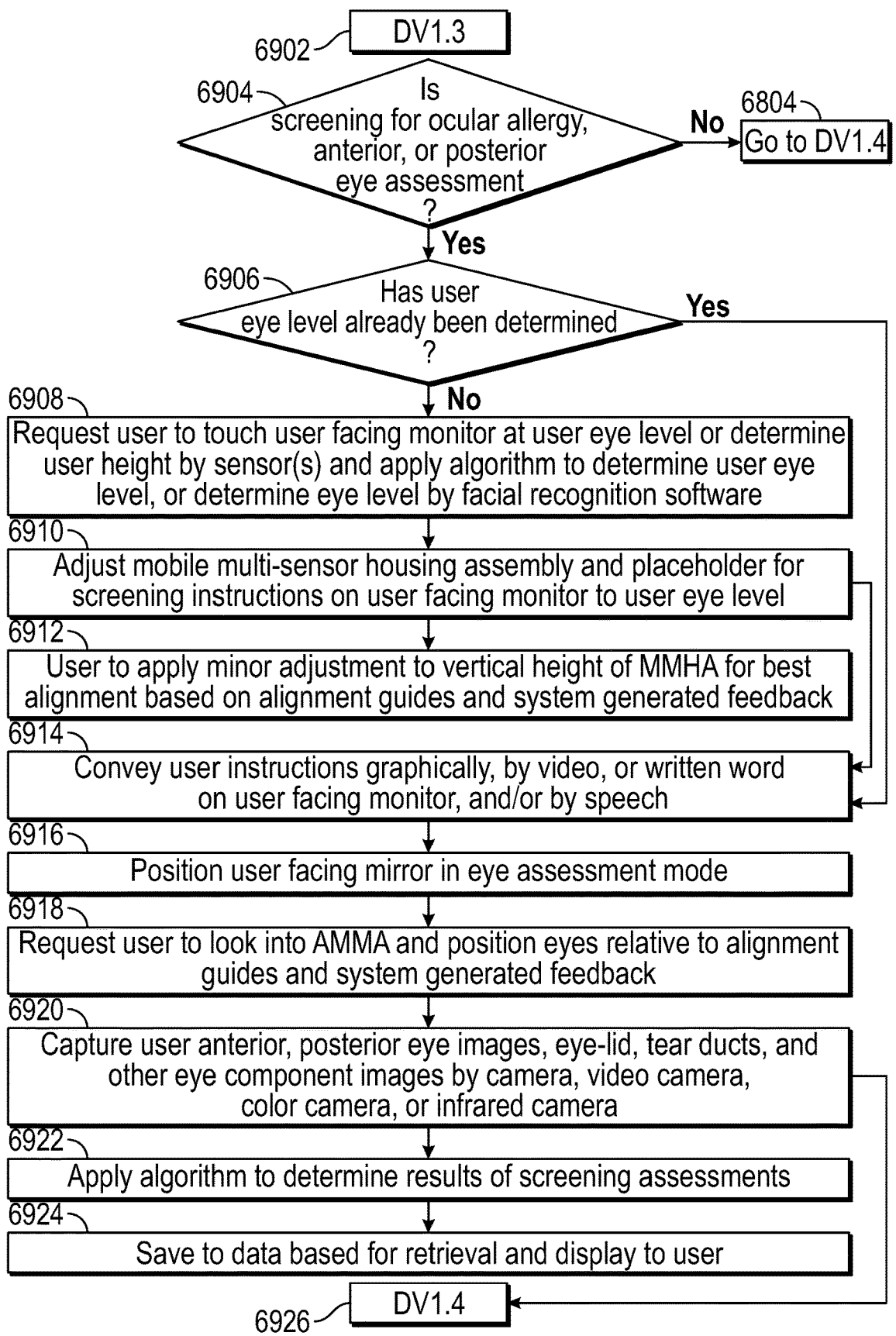

FIG. 69 depicts the software flow for screening for Ocular Allergy, and Anterior or Posterior Eye assessment, 6904. If the user's eye level has already been determined, 6908, 6910, and 6912, the system presents the user with instructions, 6914, for selected screening(s) graphically, by video, voice, or written word on User Facing Touch Screen Monitor, E-15. If user height has not been determined, the user's height is determined in the manner described above and in 6910, 6912, and 6914. Upon positioning Moveable Housing Assembly II, A-3, at user's eye level, the system moves User Facing Mirror 34 into the eye assessment mode utilizing Actuator E-5, thereby creating an optical path h between Camera(s), and Sensors E-6, Optical Lens E-7 and user's eyes, 6916. The user is requested to look into Moveable Housing Assembly II, A-3 and position their eye(s) relative to alignment guides to assure correct positioning along optical path h and Camera(s) and Sensors E-6, Optical Lens E-7 and user's eye(s). System generates and communicates feedback to user to help guide them into correct positioning, 6918. Upon correct user eye positioning, the system captures images and data relative to anterior and posterior portions of user's eye, eye-lids, tear ducts, and other eye components utilizing, but not limited to, camera(s), black and white, Infra-red, and color video camera(s), 6920. AI and algorithms are applied to process captured user data to determine user screening results, 6922, and saved to data base for retrieval and display to user, 6924.

Figure 70:
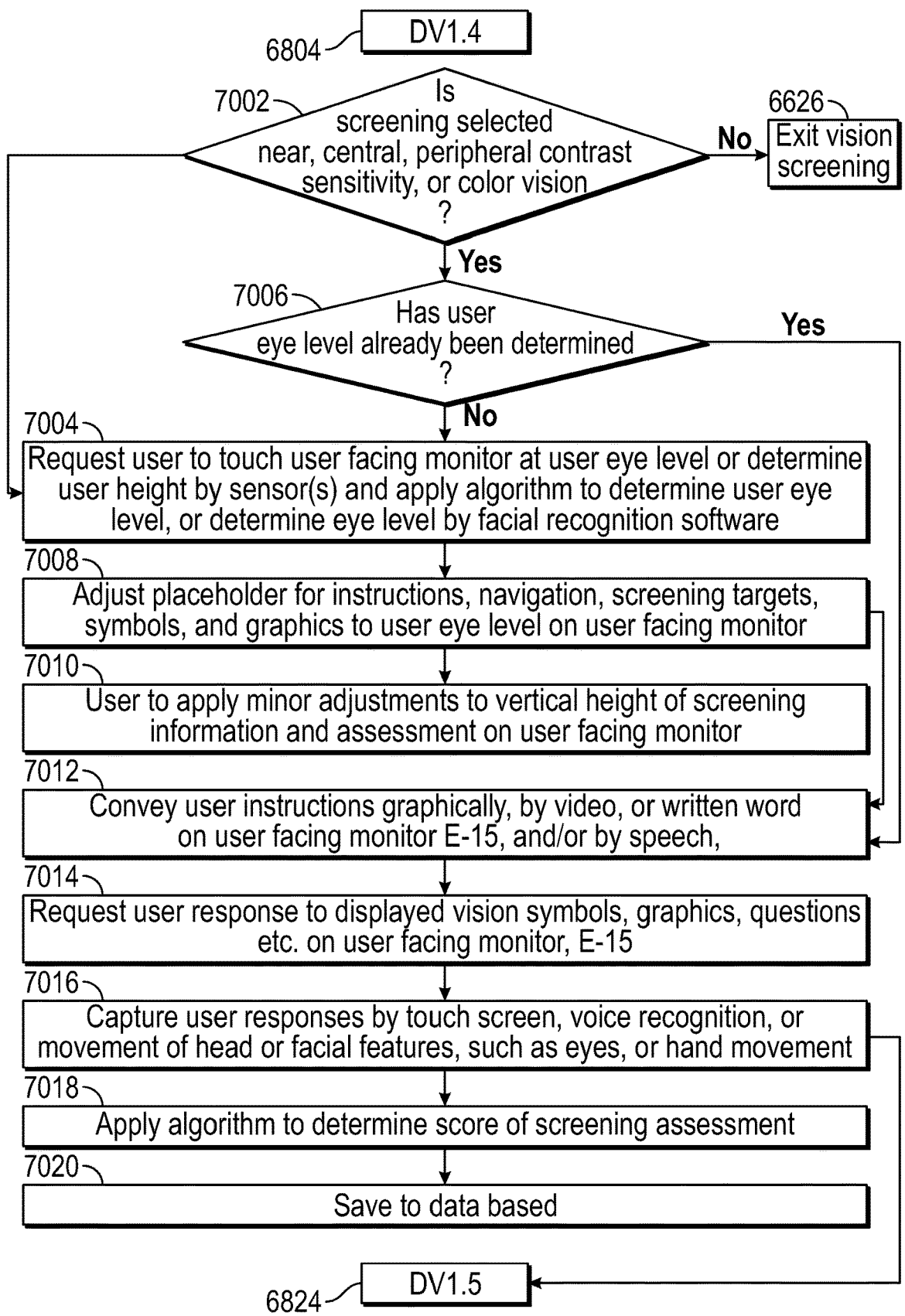

FIG. 70 depicts the software flow for a user engaging in Near, Central, Peripheral, and Color vision screening, as well as Contrast Sensitivity assessment, 7002. If the user's eye level has already been determined in steps 7004, 7006, 7008, and 7010, the system presents the user with instructions, 7012, for selected screening(s) graphically, by video, voice, or written word on User Facing Touch Screen Monitor, E-15, or another monitor that may be included in moveable housing assemblies Moveable Housing Assembly A-2 and Moveable Housing Assembly II A-3. If user height has not been determined, the user's height is determined in the manner described in 7004 through 7010. The system requests user response to symbols, graphics, and questions displayed on User Facing Touch Screen Monitor E-15 and/or on another monitor that may be included in Moveable Housing Assembly A-2 and Moveable Housing Assembly II A-3, presented at user's eye level in order to prevent distortion and variability in the optical path length from displayed content to user's eyes, 7014. User responses are captured by input via touch on User Facing Touch Screen Monitor, E-15, or by voice recognition, or user movement of head or facial features, such as eyes, or hand movement, 7016. AI and algorithms process user input data to determine score of screening assessment, 7018, and saved to data base for retrieval and display to user, 7020.

Figure 71:
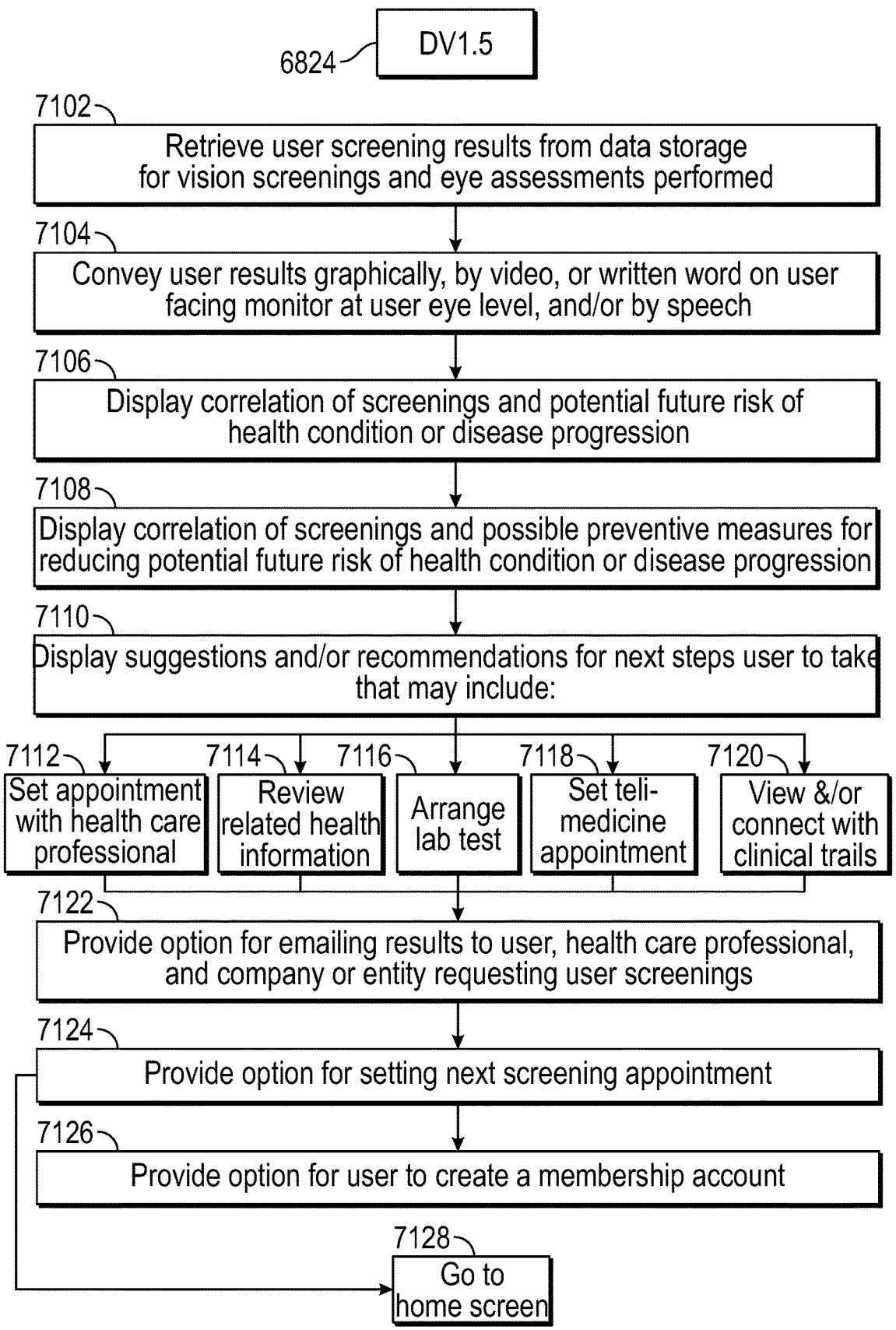
Figure 72:
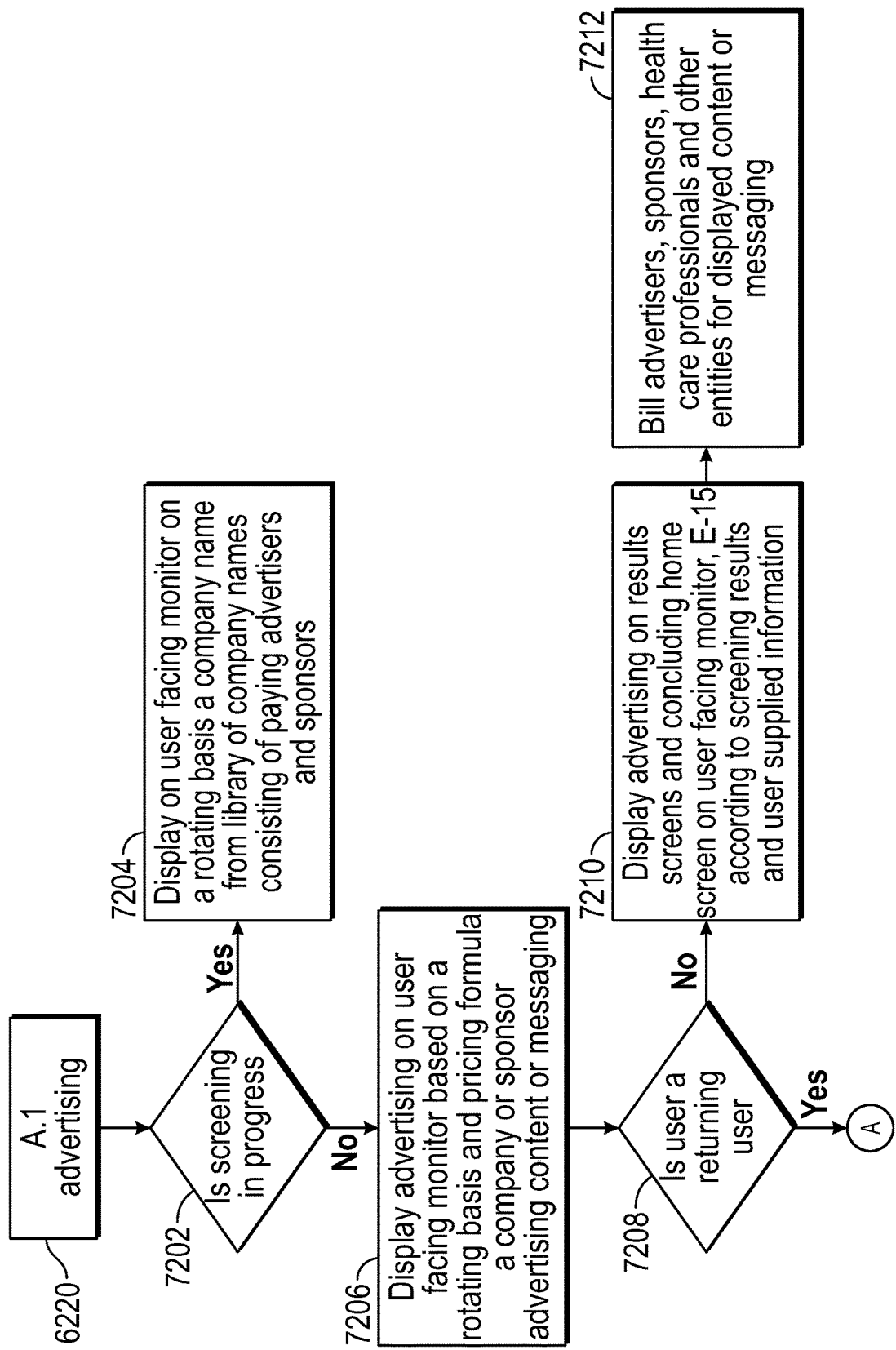
Figure 72:
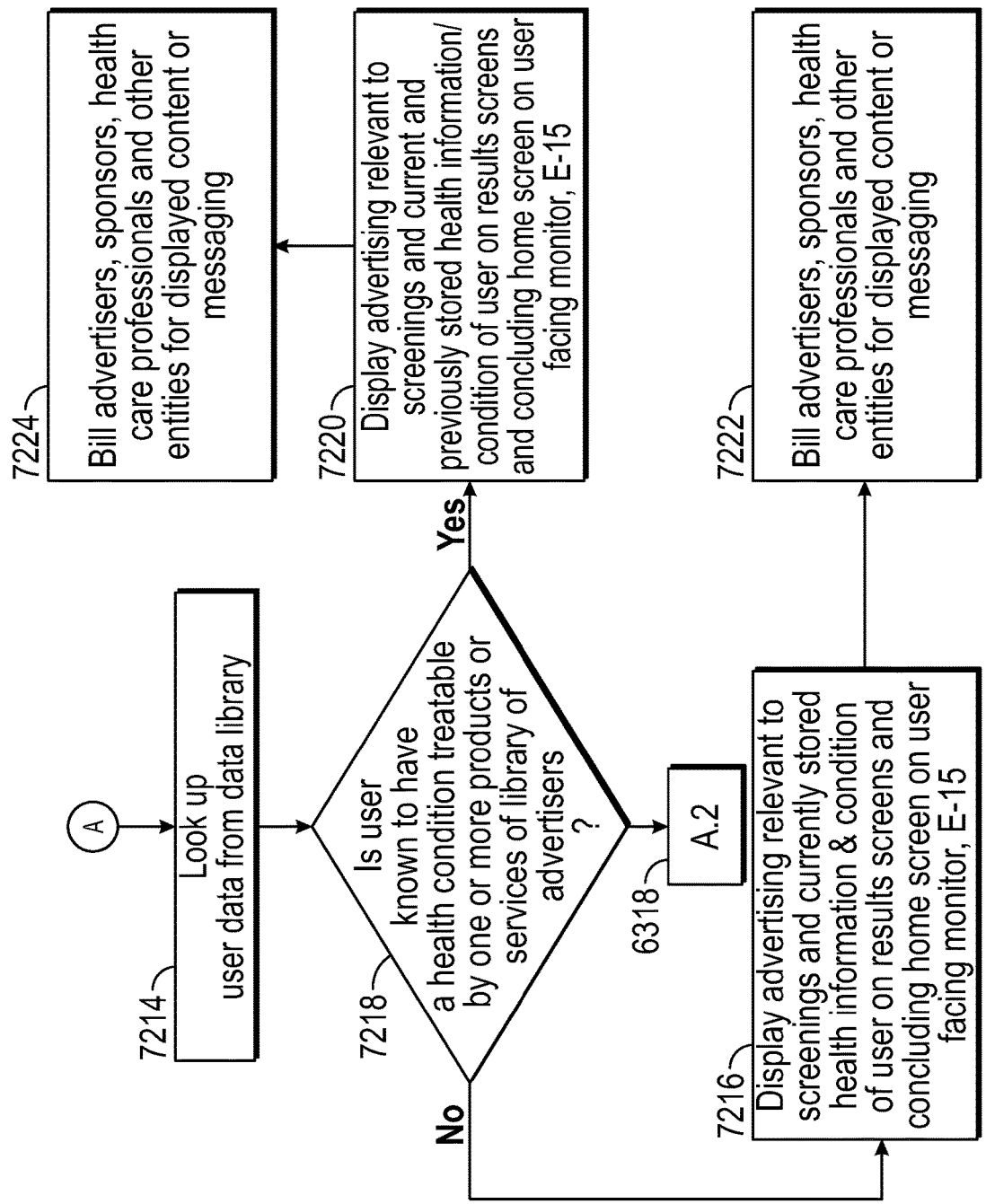

FIG. 71 depicts the system retrieving user screening results from data base (storage) for vision screenings and eye assessments performed, 7102. User results are displayed in written and/or graphic form, preferably at user's eye level, on User Facing Touch Screen Monitor, E-15. A unique feature of present inventions is the presentation of user's multiple screening results by threading together pre-recorded voice or video segments producing the effect that the person of the voice or in the video is actually speaking to the user and presenting their personalized screening results, 7104. Utilizing system AI and algorithms, the system calculates the potential risk of a health condition progressing, possible preventive measures for reducing these risks, and suggestions and recommendations for the user to act upon now that could favorably impact their health relative to screening results, 7108, 7109, and 7110. The system may display one or more of the recommended follow-up actions, including but not limited to, Set An Appointment With A Healthcare Professional, 7112, Review Related Health Information from library of Health Topics, 7114, Arrange A Lab Test, 7116, Set-Up A Tele-Medicine Appointment, 7118, and/or View & Connect With Relevant Clinical Trials, 7120. 7122 provides option for emailing results, system generated suggestions and recommended actions, and other options a user may select. This content may be sent to the user, and other parties, including but not limited to, a healthcare professional, company, or entity requesting user health screening. AI and algorithms calculate the time interval recommended between screenings for the user, based upon a number of factors, including but not limited to, user's age, nationality, gender, health status, severity of screened condition or risk, and likelihood of health condition(s) progressing. System provides user the option to be reminded of their recommend next visit via text message, email, voice mail, etc., 7124. If user is not a member, 7126 provides an opportunity for user to create a membership account, 7126.

The software determines if a screening is in progress, 7102. If a screening is in progress, an advertiser, sponsor, or host is displayed at the top or bottom of User Facing Touch Screen Monitor, E-15, to allow room for navigation, information, user engagement, user screening results, etc. to be displayed and easily viewed by user. Selection of displayed advertiser, sponsor, host, or other entity may be on a rotating basis, or as a result of auction pricing, 7204.

If a screening is not in progress, the system may allocate a portion or all of the display area of User Facing Touch Screen Monitor, E-15, to one or more advertisers, sponsors, hosts, or other entities based on pricing formulas and/or auction pricing, 7206. The system determines from user input or biometric assessment such as facial recognition, if user is a "returning user," 7208. If user is not a returning user, system displays advertiser and sponsor messaging when user receives their results on User Facing Touch Screen Monitor, E-15, specific to their current screening results or information they provided to the system. Advertiser content relative to user screenings or user provided information may also be displayed when system returns to the "Home Screen," 7210. Advertisers, sponsors, and other entities displaying content on system are billed according to pricing algorithms, 7212. If a user is a "returning user," the system inquires the data base to ascertain if user past screenings or supplied health information relates to an advertiser, sponsor, healthcare professional or other healthcare entity stored in system database. The system displays advertising and sponsor content relevant to screenings and stored health information/condition of user on Results Screens and concluding Home Screen on User Facing Monitor, E-15. Advertisers, sponsors, and other entities displaying content on system are billed according to pricing algorithms, 7224. If user is not "returning user" then displayed advertising is based on currently provided user health/demographic Information and screening results, displayed on User Facing Monitor, E-15, and advertisers/sponsors billed, 7222.

Figure 73:
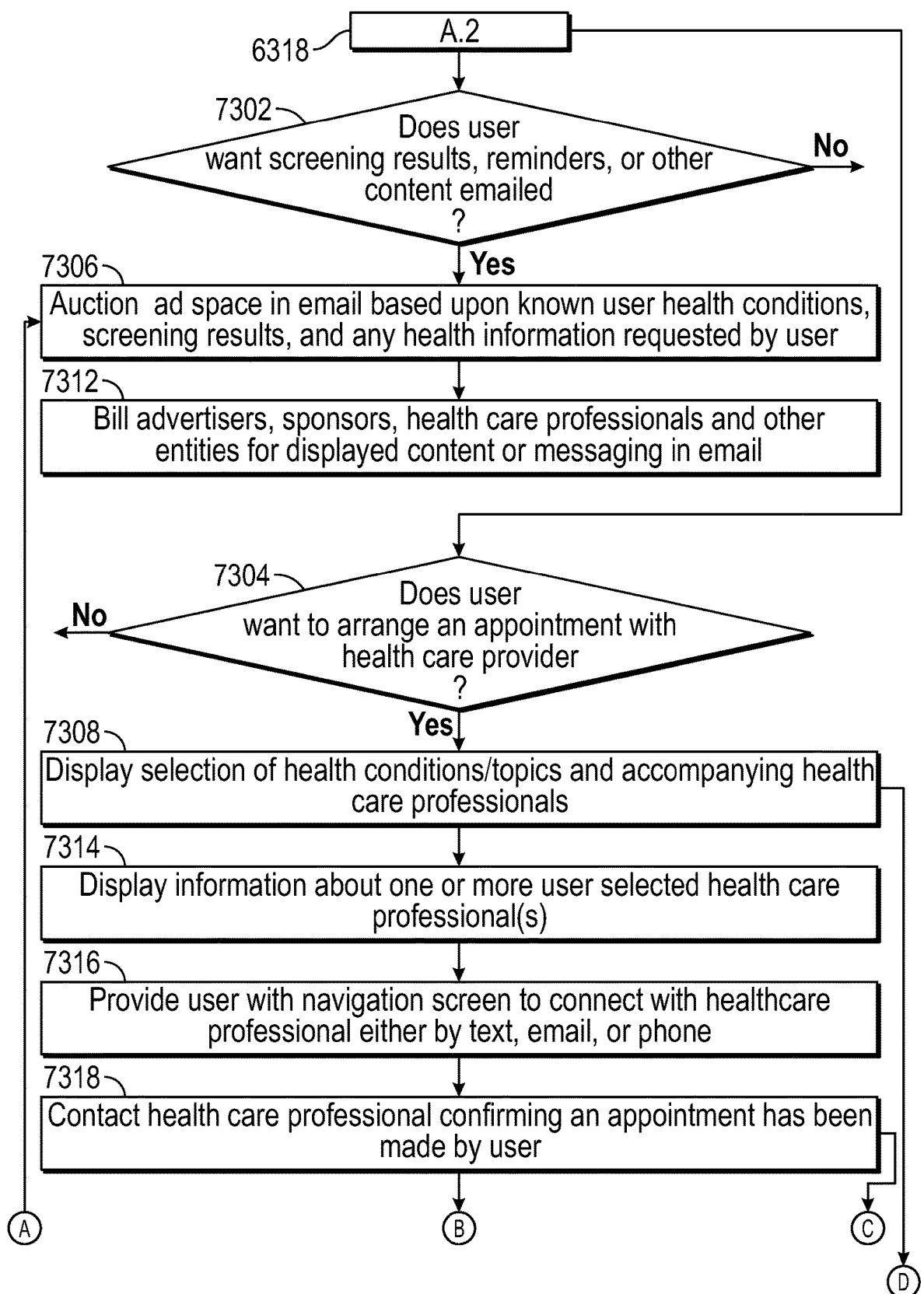
Figure 73:
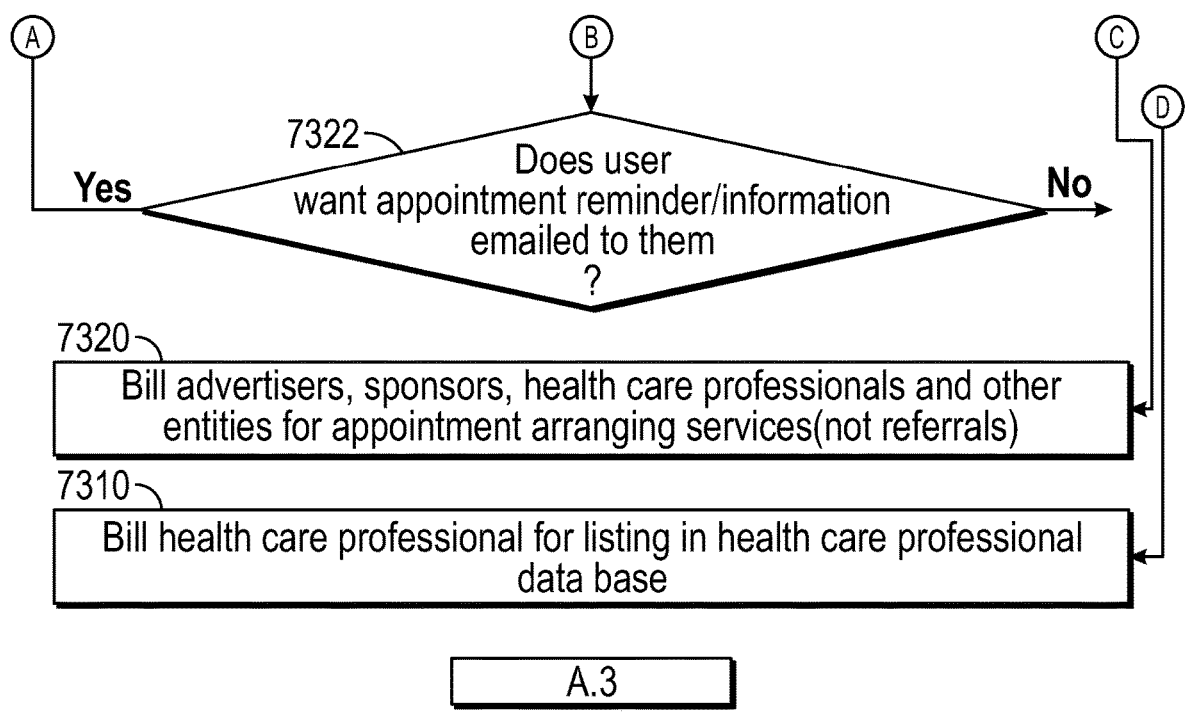

FIG. 73 depicts the opportunity for a user to select the system to email user their screening results, health or product information, coupons, and reminders such as next screening date or appointments made with listed healthcare professionals, 7302. The system will auction advertising space in the email based on products or services relevant to known user health conditions, screening results, health information, (e.g. auto and safe driving information, vision information, etc.), and other sponsors promoting a healthy lifestyle as requested by user, 7306. System automatically bills advertisers, sponsors, healthcare professionals or other entities for their content or messaging in email sent to user, 7312. The system also provides user with the opportunity to arrange an appointment with a healthcare professional, 7304. Upon user selection, 7308, the system displays a selection of health conditions and topics and when selected, healthcare professionals providing these services are displayed. Healthcare professionals are billed for listing in system data base, 7310. User may select one or more healthcare professionals to view more detailed information and given the opportunity to make an appointment with selected health provider, 7314 and 7316, respectively. The system automatically sends selected healthcare professional a confirmation that an appointment has been arranged through the present invention, 7318. Healthcare professionals are billed for appointment arranging, confirmation, and user reminder services, and not for a referral fee, 7320. If user wants appointment reminder or healthcare professional information emailed to them, 7322, system provides this information and refers to 7306 for auctionable advertising or sponsor content.

Figure 74:
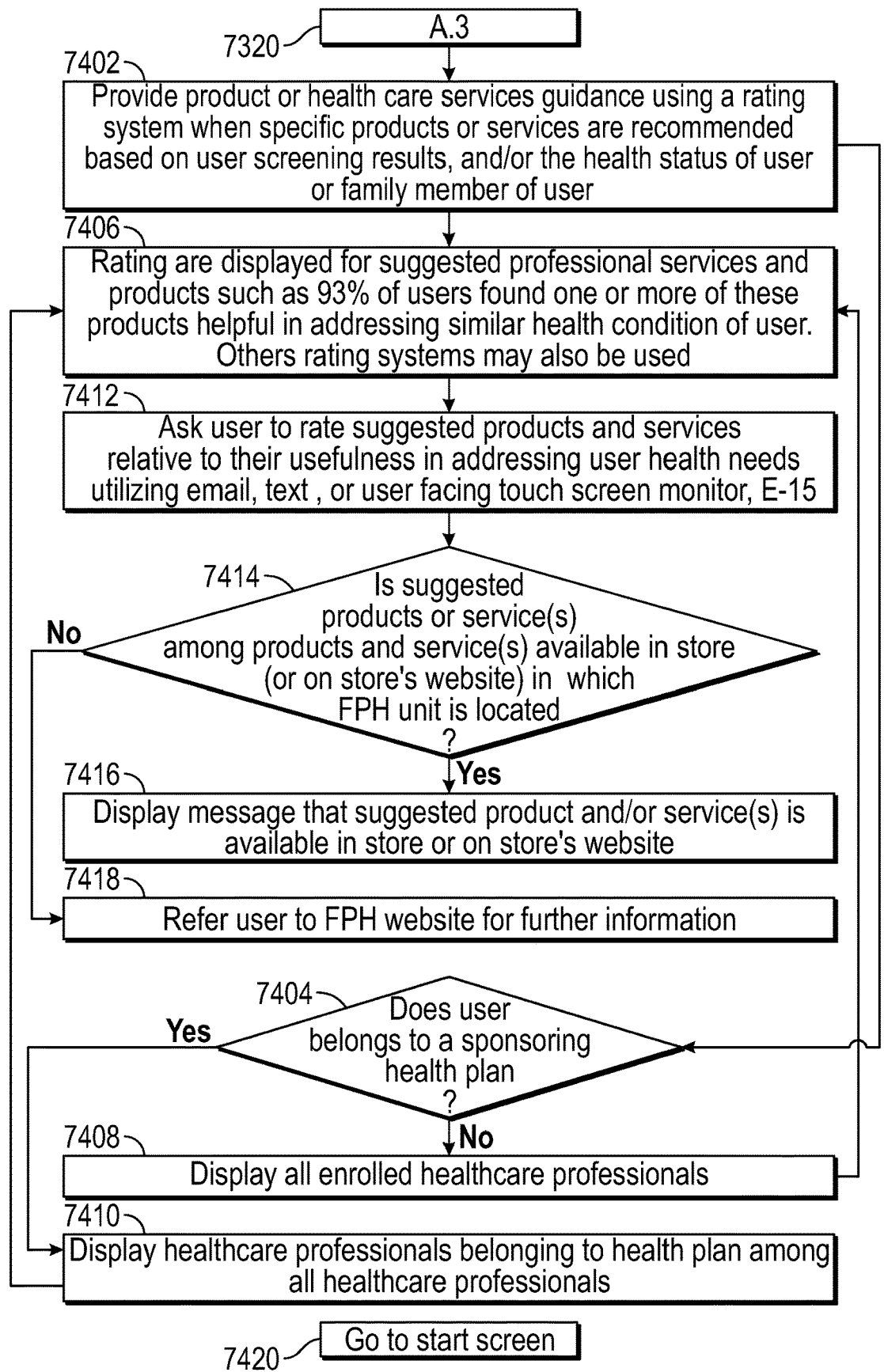

FIG. 74 illustrates system ability to provide user guidance and ratings of suggested products and healthcare services, 7402. In the event user belongs to a health plan, those healthcare professionals belonging to health plan are highlighted, 7404 and 7410, respectively. (Heathcare professionals belonging to a health plan may pay extra for this privilege). If user does not belong to a health plan, all healthcare professionals enrolled in system data base will be available for viewing. Professional services will be filtered by specialty and location, 7408 and 7410. Previous users throughout the network of present inventions will rate products and services relative to their effectiveness in addressing their health needs and conditions as discovered through user's self-directed screening. These are displayed to a current user, 7406. A current user is asked to complete a survey for any product or service suggested by the system and used by them. Surveys are transmitted to and from the user utilizing email, text, User Facing Touch Screen Monitor E-15, or through FirstPoint Health website, 7412. The system will notify a user that a suggested product or service is located in a store or on the store website, assuming present inventions is located in a retail store environment. In the event a product or service is not located in the store or on the store website, user will be directed to FirstPoint Health website for further information, 7418, respectively.

Figure 75:
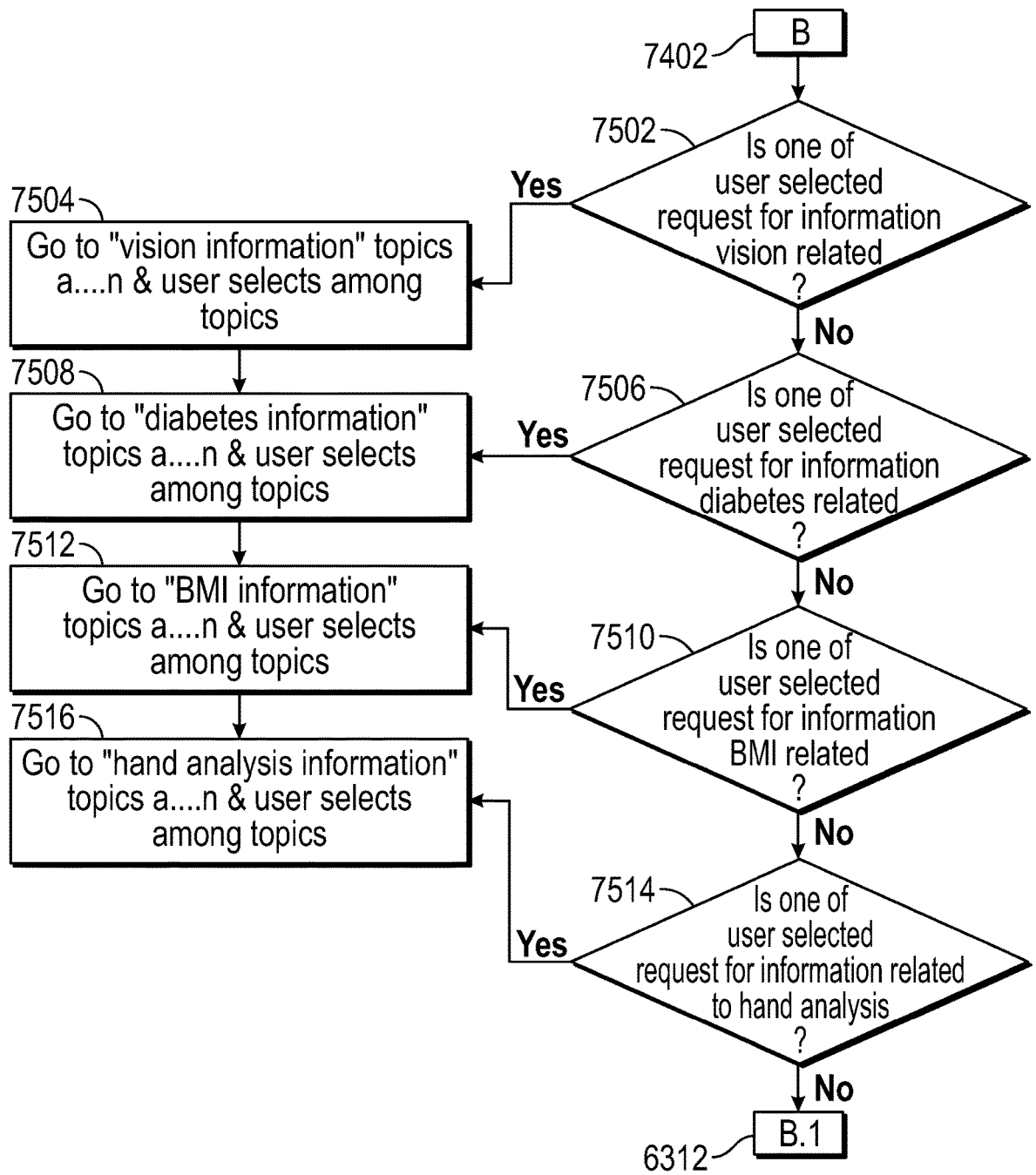
Figure 76:
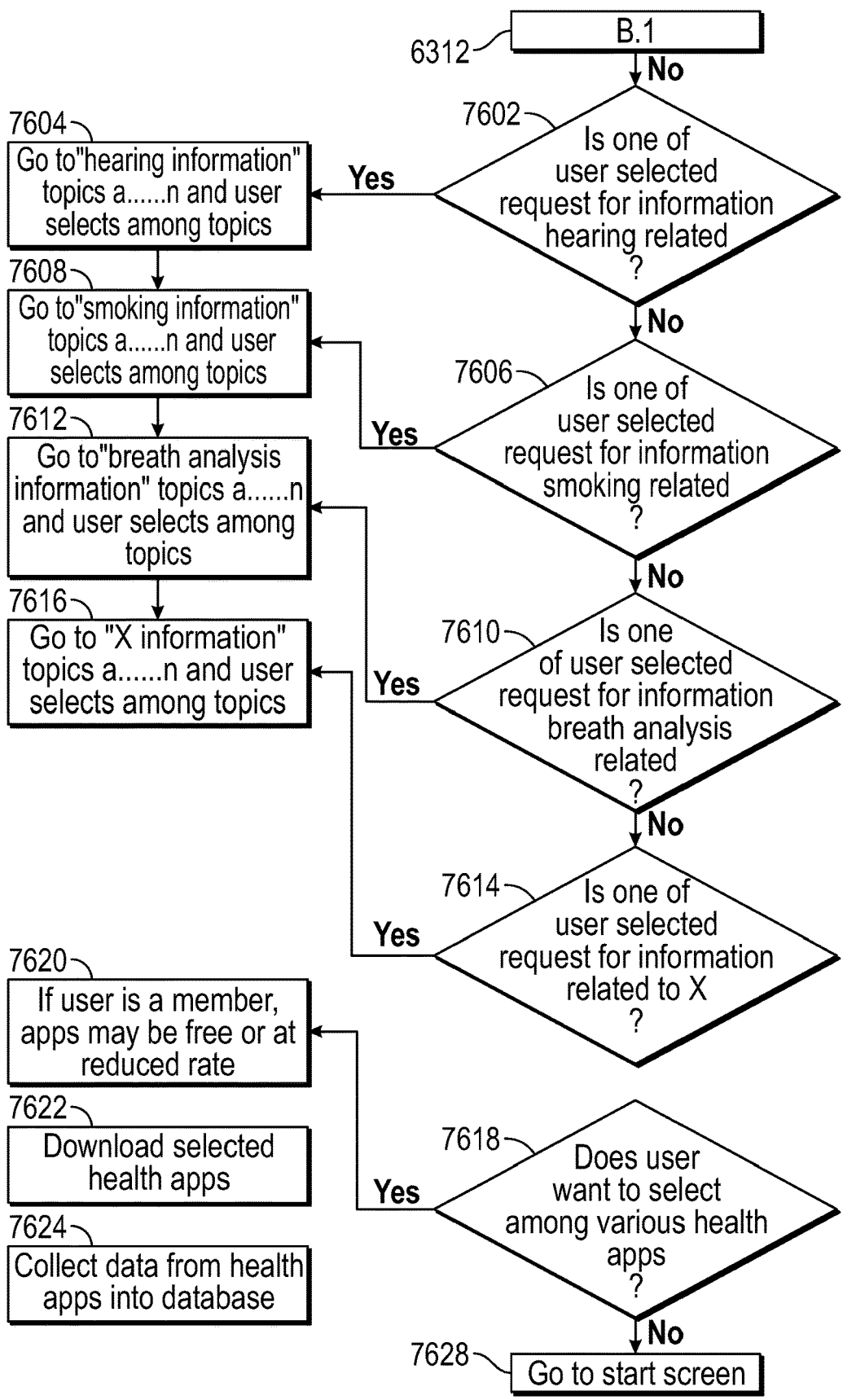

FIG. 75 and FIG. 76 illustrate system software providing user with Health Information. User may request information related to Vision, 7502, and systems displays Vision topics a . . . n, from which user makes a selection. Health information is presented on screen but preferably emailed to user. User is directed to FirstPoint Health website for further Information on selected topic(s). In a similar manner, user may request information that is related to Diabetes, 7506; BMI, 7510; Hand analysis, 7514; Hearing, 7602; Smoking, 7606; Breath Analysis, 7610; and additional topics a . . . n, 7614. The system will also provide users the opportunity to download Health Apps, 7618, either directly from system through technology such as 'Bump' or downloadable from FirstPoint Health's website. To encourage users becoming members, Health Apps may be available at a reduced price or free, 7620. The user may be asked to download selected Health Apps 7622. Through arrangements with Health App creators, user data may be shared with FirstPoint Health enabling better assessments and deeper understanding into user health, 7624.

Figure 77:
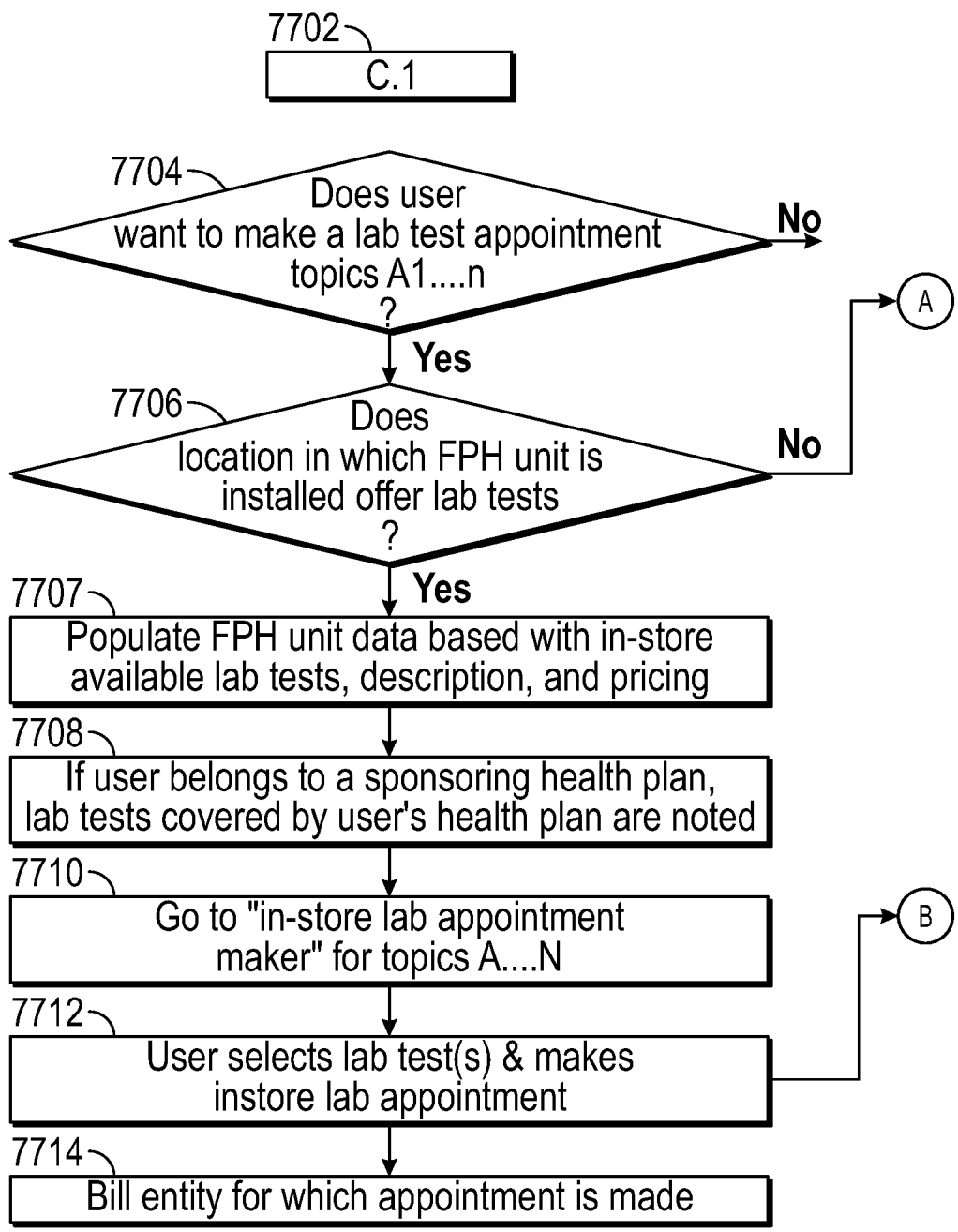
Figure 77:
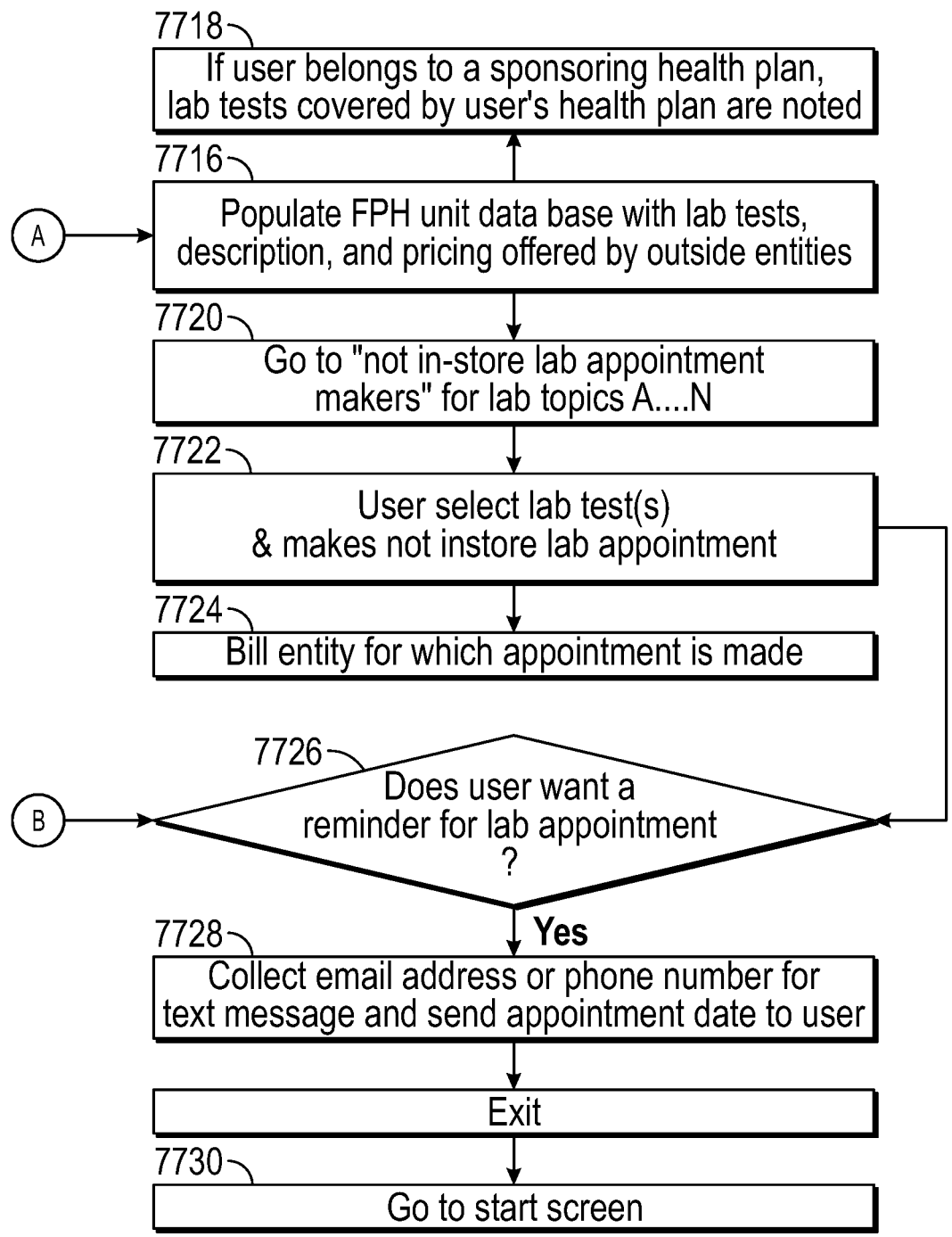

FIG. 77 shows software flow allowing a user to make an appointment for either an 'in-store' or "out-of-store" Lab Test, 7704. If the location in which the present inventions is located provides Lab Tests, the User Facing Touch Screen Monitor, E-15 is populated with menu of lab tests, description, and pricing, 7706 and 7707. If user belongs to a sponsoring health plan, lab tests covered by user's health plan are noted, 7708. The system displays an 'in-store' Lab Appointment Maker for the list of lab topics offered at this location, A . . . N, 7710, where user makes appointment for selected lab tests, 7712. The system bills the entity lab for appointment services completed, 7714. In a similar manner, a user may make an "out-of-store" Lab Appointment, 7716 through 7722. The system bills the outside lab entity for lab appointment services completed, 7724. User may select if they would like a reminder of lab appointment and provide contact information to enable a reminder prior to lab test appointment, 7726 and 7728.

Figure 78:
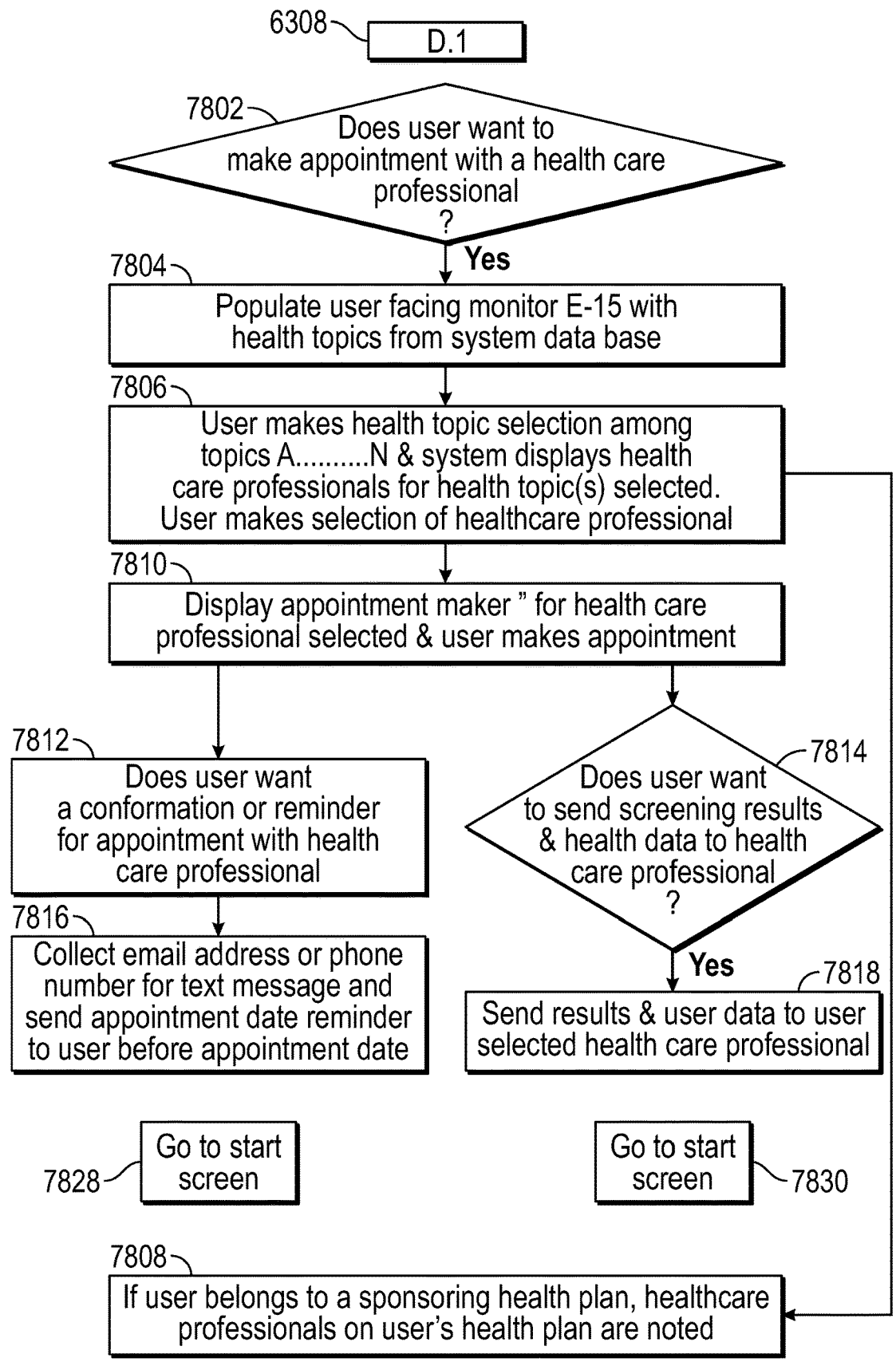

FIG. 78 shows software flow allowing a user to make an appointment with a healthcare professional, clinic, or hospital, 7802. System populates User Facing Monitor E-15 with Health Topics from system data base, 7804. User makes health topic selection among topics A . . . N and system displays healthcare professionals for health Topic(s) selected. User makes selection of healthcare professional, 7806. If user belongs to a sponsoring health plan, healthcare professionals in user's health plan are highlighted or noted, 7808. System displays Appointment Maker for healthcare professional selected and user makes appointment, 7810. If user would like a confirmation of the appointment or reminder of appointment date, system collects user contact information and sends to data base for appointment reminder and appointment confirmation with selected healthcare professional, 7812 and 7816. User may also send their screening results and/or their health data to selected healthcare professional prior to their appointment. If selected, system emails information to user selected healthcare professional, 7814 and 7818. There is also collection of email address or phone number for text message and send appointment date reminder to user before appointment date.

Figure 79:
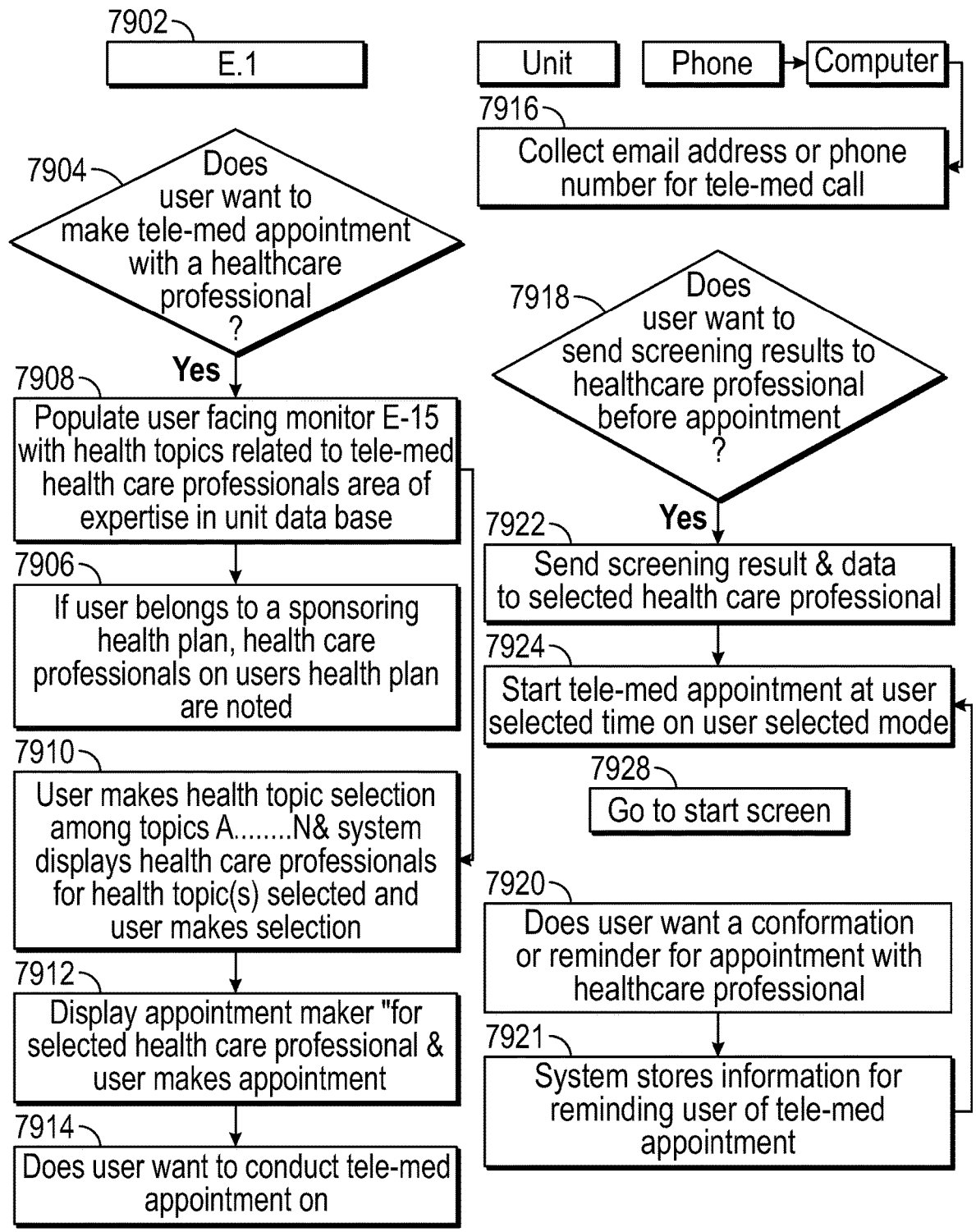

FIG. 79 shows software flow allowing a user to make a Tele-Medicine Appointment with a healthcare professional, 7904. The system populates the User Facing Touch Screen Monitor E-15 with health topics related to the areas of expertise of healthcare professionals stored in system data base, 7908. If user belongs to a health plan, displayed healthcare professionals belonging to user's plan are highlighted or noted, 7906. Upon user making a health topic selection, system displays healthcare professionals with expertise in selected health topic, and user selects healthcare professional, 7910. System displays Appointment Maker for a Tele-Medicine call with selected healthcare professional and user makes appointment, 7912. System also allows user to select the mode for conducting tele-med appointment and user selects among conducting on unit, phone, or computer and system collects necessary user contact information for mode user selects, 7914 and 7916. The user also has the option of sending their screening results and health data to healthcare professional prior to their Tele-Medicine Appointment, 7918 and 7922, and may receive a confirmation and/or reminder of appointment, 7920 and 7921. The process is completed when user and selected healthcare professional conduct tele-medicine call at the appointment time and on user selected mode, 7924.

Figure 80:
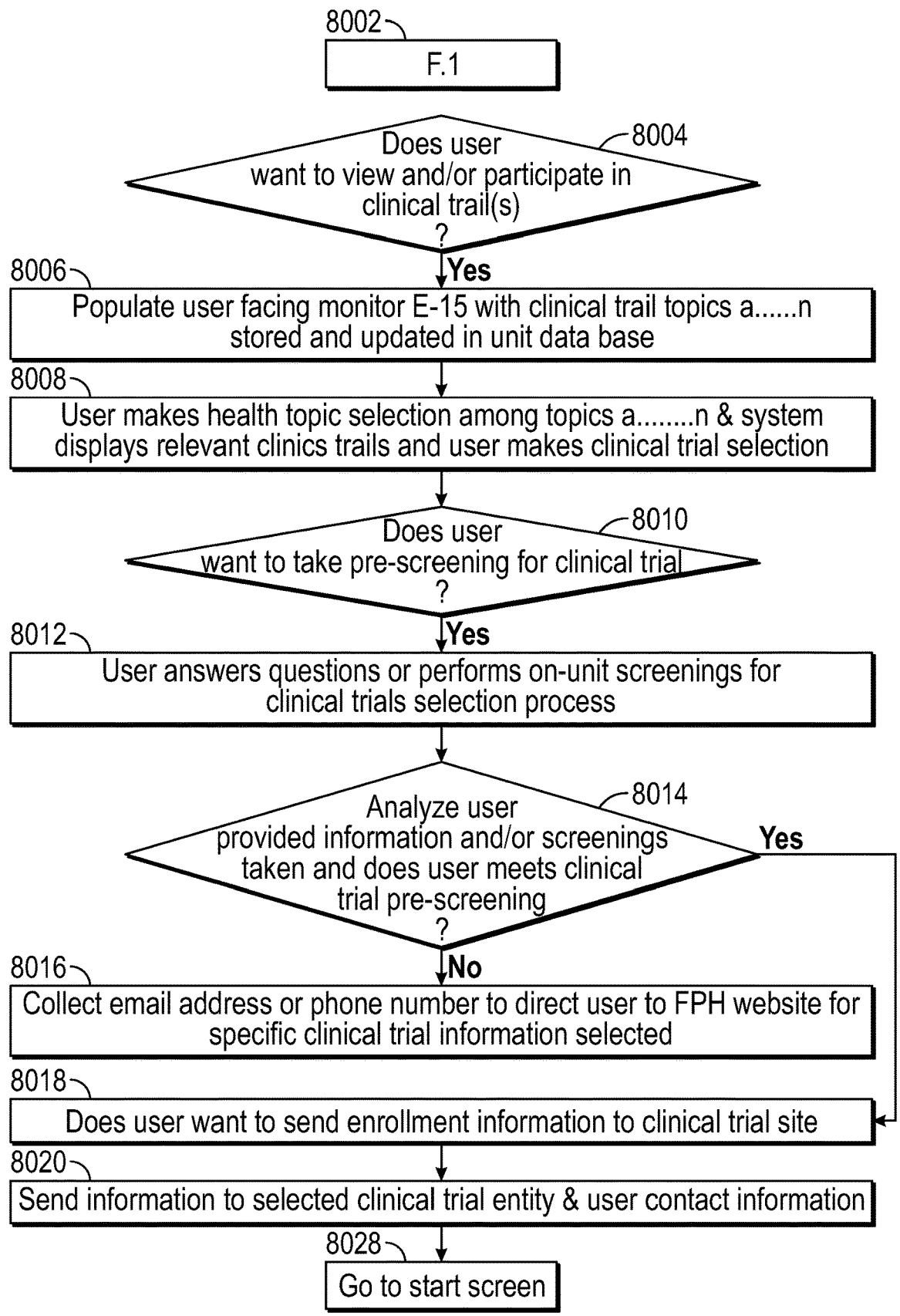

In FIG. 80, the system also allows a user to learn about, and if pass clinical trial selection process, participate in clinical trial(s), 8004. User Facing Touch Monitor, E-15 is populated with topics a . . . n which are stored and updated in system data based, 8006. User selects health topic and system displays relevant clinical trials open for enrollment. User makes clinical trial selection, 8008. System provides user with the opportunity to see if they qualify to participate in selected clinical trial, 8010, and if user desires to do so, the system displays questions provided by company conducting clinical trial, which also may include one or more self-directed screenings available of present invention, 8012. The system reviews user supplied information and screenings performed to determine if user meets clinical trial qualifications, 8014. If user does not pass, system directs them to FirstPoint Health website for further information, 8016. If user meets the pre-screening criteria for selected clinical trial, user has the option of submitting this information to company conducting clinical trial, 8018. If user would like to submit information, the system sends this information to clinical trial company along with user contact information and any user health data or screening assessment selected by the user, 8020.

Figure 81:
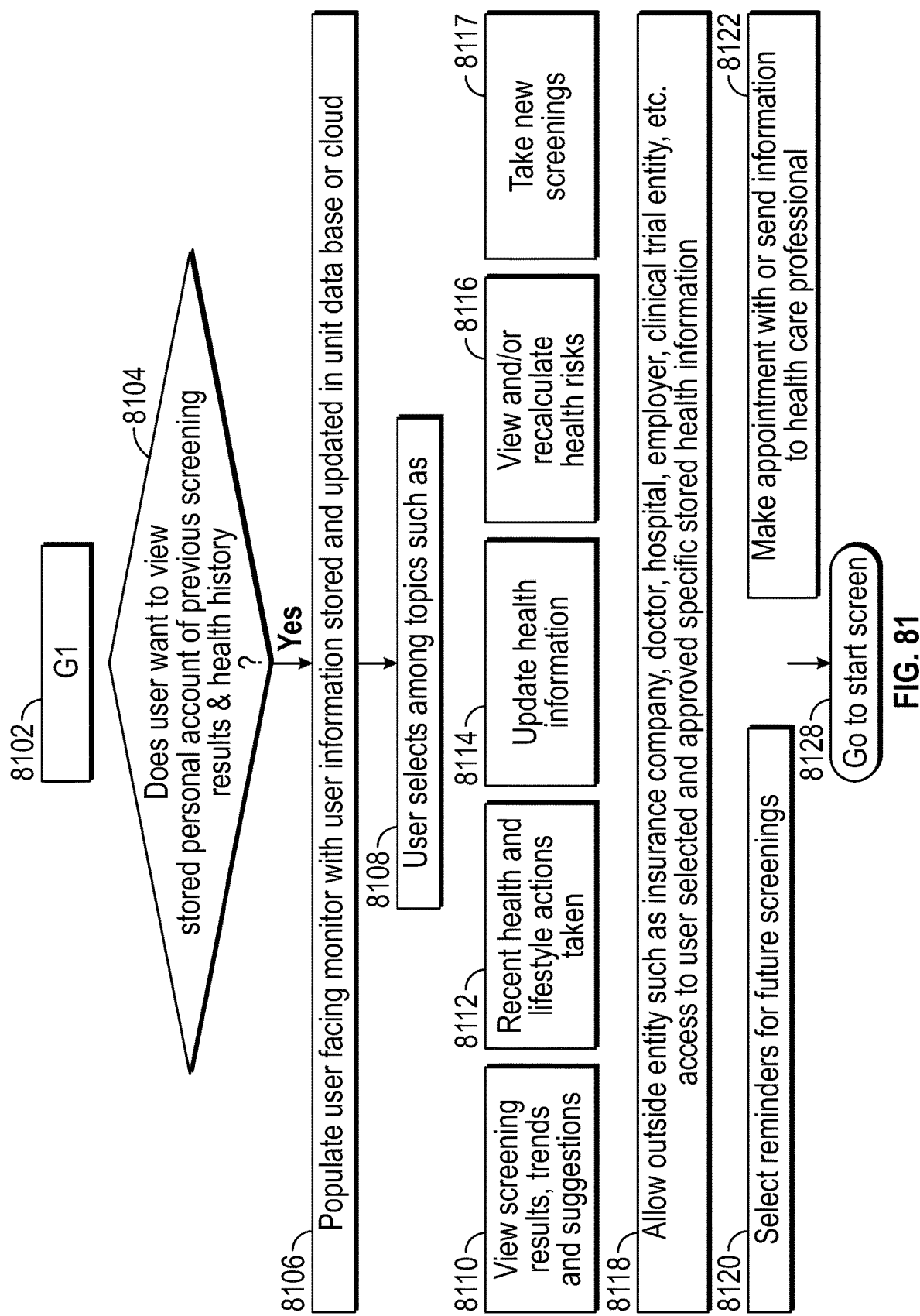

As shown in FIG. 81, if the user is a member within the FirstPoint Health Network, the system allows them to review their past screenings, personal health trends, system suggestions, changes in their health risks, and health preventive measures, 8104. Upon User selection, system populates User Facing Touch Screen Monitor E-15, with a navigation template allowing user to review and/or update their personal data and health information, 8106. User makes a selection, 8108, among presented topics including, but not limited to, (1) view personalized screening results, trends, and system generated suggestions 8110, (2) recent health and lifestyle actions taken 8112, (3) update health or family health information 8114, (4) view and recalculate health risks 8116, (5) allow an entity such as an insurance company, healthcare professional, employer, clinical trial company, etc. access to screening assessments and health data of user that are approved by use 8118, (6) set reminders for future screenings 8120, and (7) make appointment with or send information to a healthcare professional (including a telemedicine appointment), or select a screening 8117.

Figure 82:
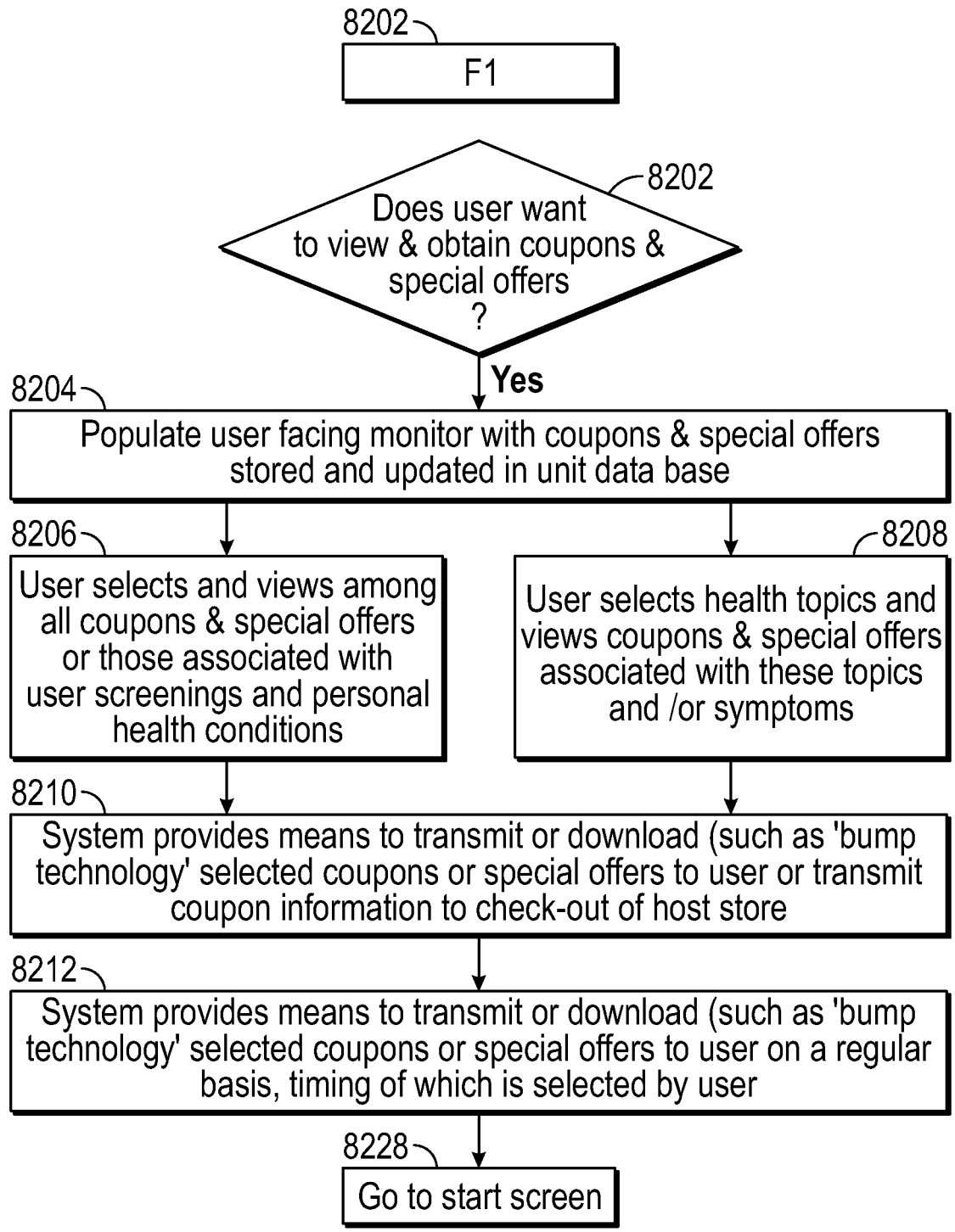

FIG. 82 shows the software flow allowing a user to view and obtain coupons and special offers, 8202. When selected, the system populates and displays on the User Facing Touch Screen Monitor, E-15 time-sensitive coupons and special offers stored and updated in system data base, 8204. User may select coupons and special offers from all available coupons and special offers or those specific to user's health screening results and personalized health conditions, 8206. User may also search data base of Coupons and special offers by health topics or health symptoms, 8208. System provides user to transmit selected coupons and special offers using email, smartphone or technology imbedded in unit, such as "Bump" technology, or transmitted to check-out register of host store in which unit is located, 8210. System also allows user to receive specific coupons or special offers on a regular basis, transmitted to a user in a similar manner described above, 8212.

Figure 83:
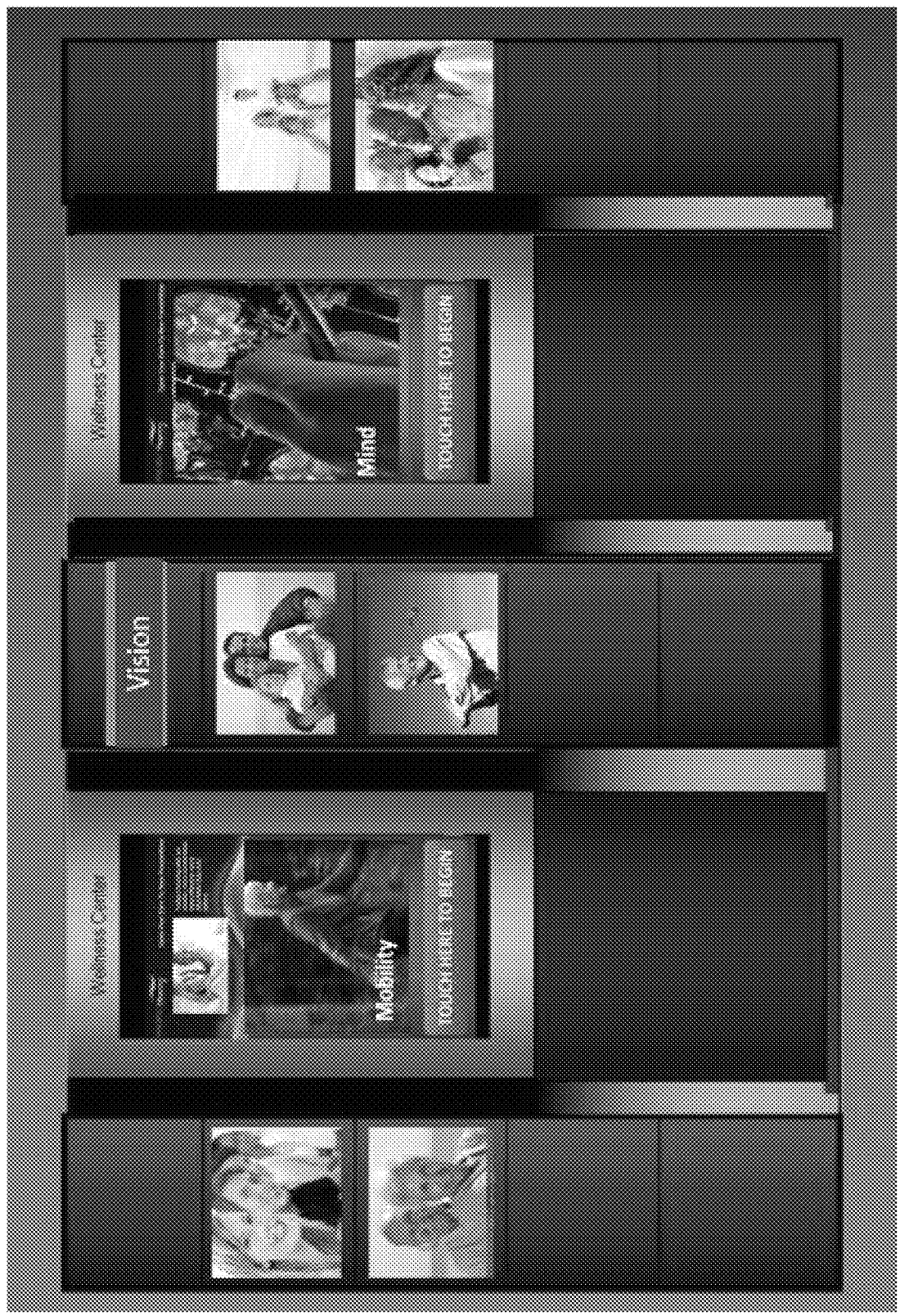
FIGS. 83-86 are examples of representative user interface and technical solution related illustrations associated with one or more implementations consistent with aspects related to the innovations herein.

FIG. 83 shows one of multiple configuration options of health walls. In particular, FIG. 83 shows two units next to each other. Other options include one unit standing by itself, or three or more units arranged as one next to another. A side-by-side arrangement of two or more units is possible. Other arrangements are also possible. The health walls can be used in pharmacies, malls, corporate health centers and other locations.

Figure 84A:
Figure 84B:
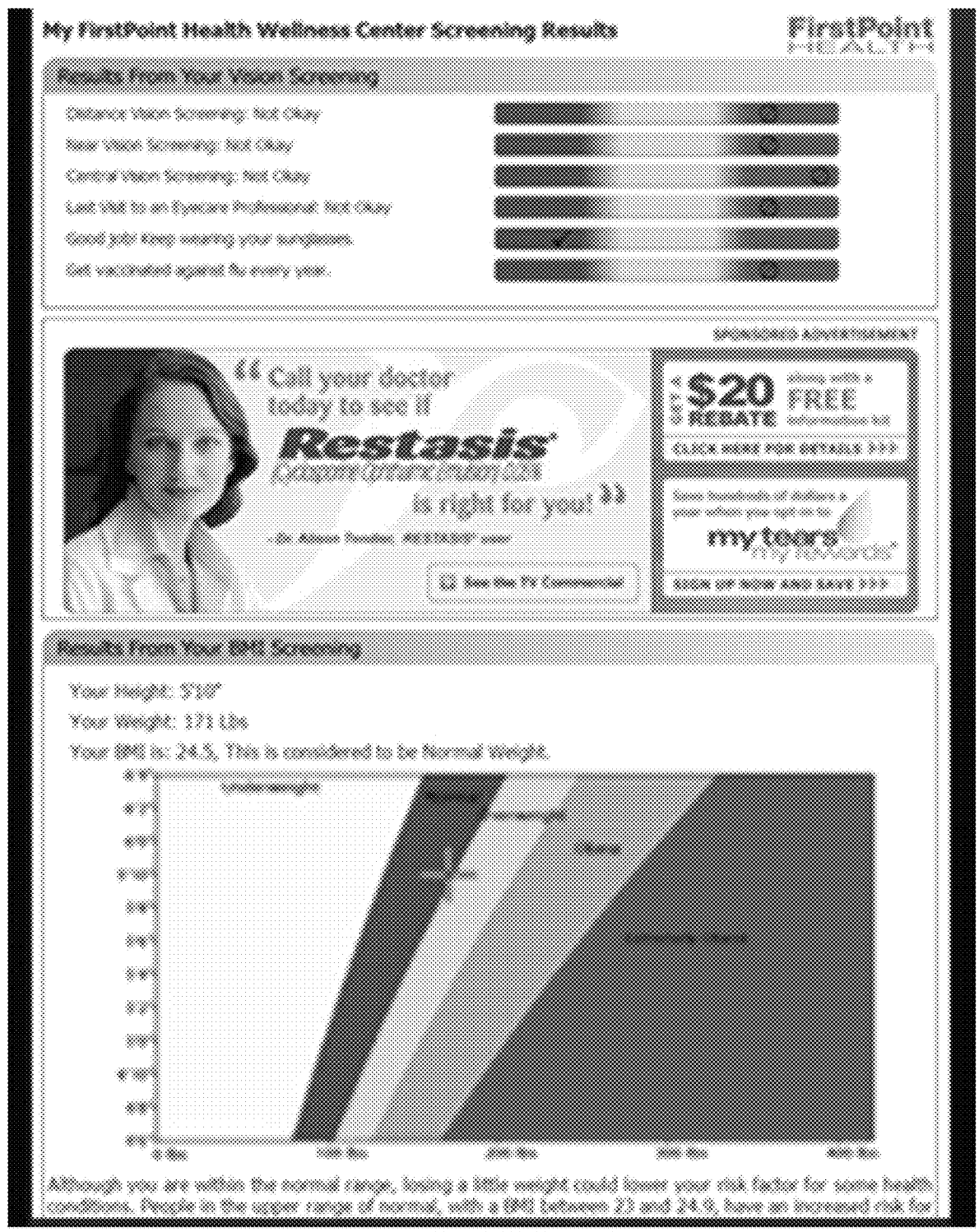
Figure 84C:

FIGS. 84A-84C show an integrated mobile app and website for the patient portal. The patient portal may be an app or a website and the patient portal includes historical data, health and lifestyle recommendations. The patient portal, as an app or a website, can also send reminders to perform regular check-ups, set up tele-medicine appointment, serve paid advertisements including video advertisements (see e.g. top of FIG. 84C illustrates an example of a video advertisement for contact lenses), and provide digital coupons for local partners (e.g. Walgreens, eye care providers, etc.) The patient portal may also prompt the user to proceed to a website. Additionally, as illustrated in FIGS. 84A-84B, the integrated portal can display such important health screening results/information such as results from vision screening(s)(top of FIG. 84B) and/or results from BMI screening(s) (bottom of FIG. 84B) in addition to one or more advertisements (middle of FIG. 84B). Important health information is not limited to just BMI and vision, but include other health analyses, screenings and results, as well, such as set forth elsewhere herein. These important health information may be provided in such a user-friendly way, e.g. via a user's mobile device as here, such that a user can quickly and efficiently perform one or more screenings and then, even later, still be able to conveniently view and asses the health analyses, screenings and results. Further, important health information being provided as a function of the health results (such as those shown in FIG. 84B) serve as more than advertisements, rather, they are individualized and targeted and provide key health analyses that provide for literally saving users' lives. For example, the health analyses, screenings and results will help identify chronic, serious, or life-threatening conditions or diseases early and alert a user to health warnings. In these situations, these health analyses, screenings, and results could prompt the user, such as via the pop-up informational video noted above, e.g., to notify a user to immediately see a doctor or other type of specialist for a more comprehensive or targeted health screening.

Figure 85:
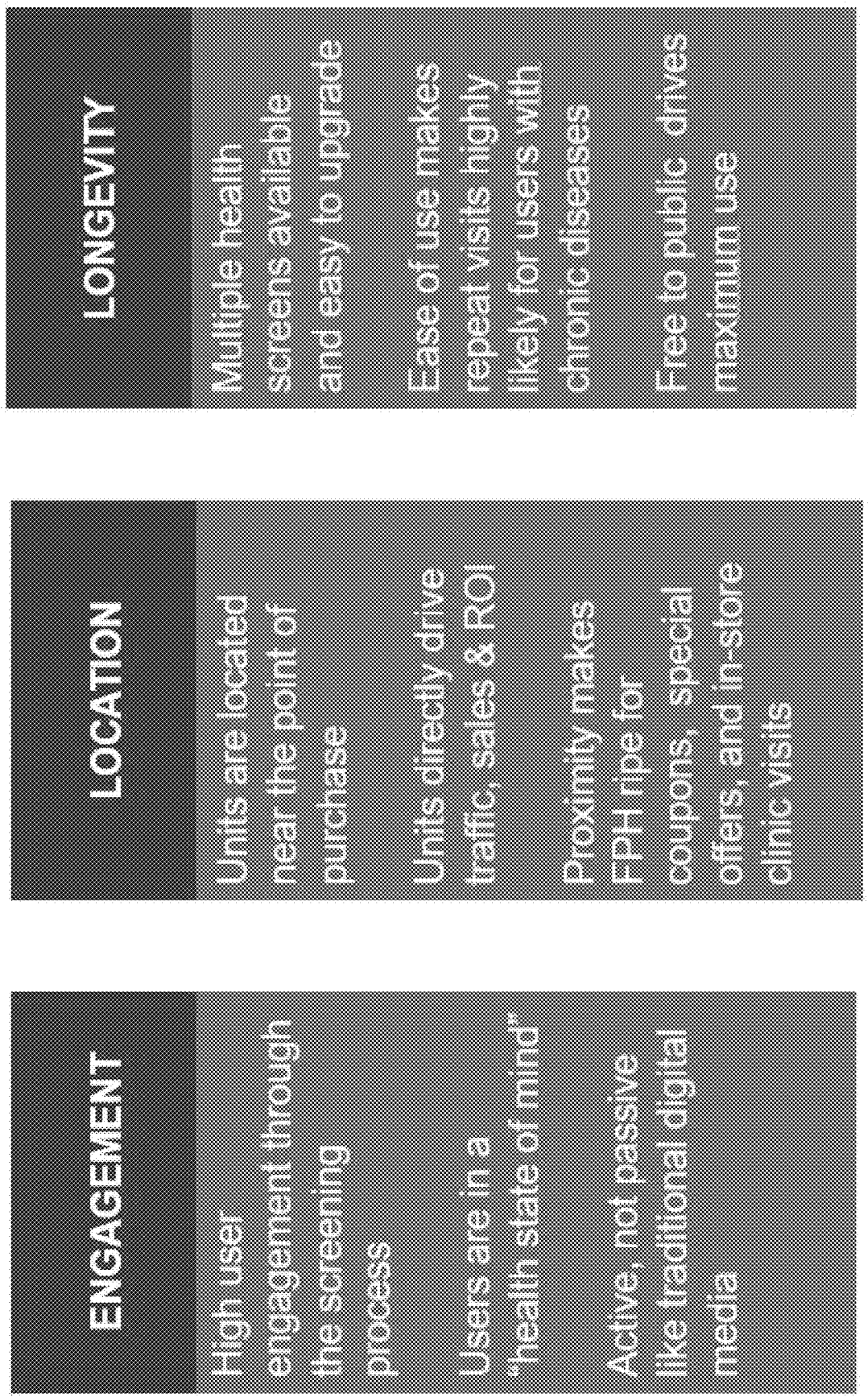

FIG. 85 shows three of many advantages the present inventions has. One such advantage is engagement. There is high user engagement through the screening process. Users are in a "health state of mind." And this engagement is active, rather than passive like traditional digital media. Another such advantage is location. The units are located near the point of purchase. The units directly drive traffic, sales and ROI. The proximity of the units makes the present inventions ripe for coupons, special offers, and in-store clinic visits. Another such advantage is longevity. Multiple health screens are available and are easy to upgrade. The ease of use makes repeat visits highly likely for users with chronic diseases. Also, being free to the public drives maximum use.

Figure 86:
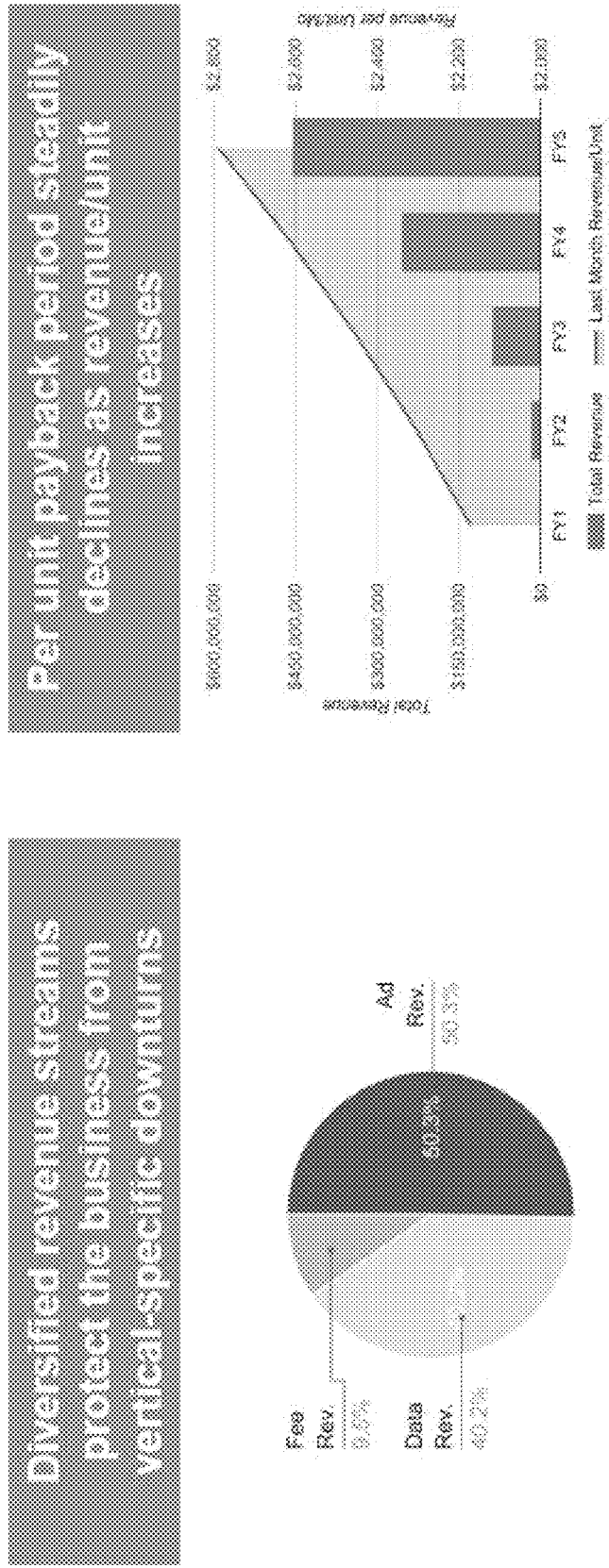
Figure 87:
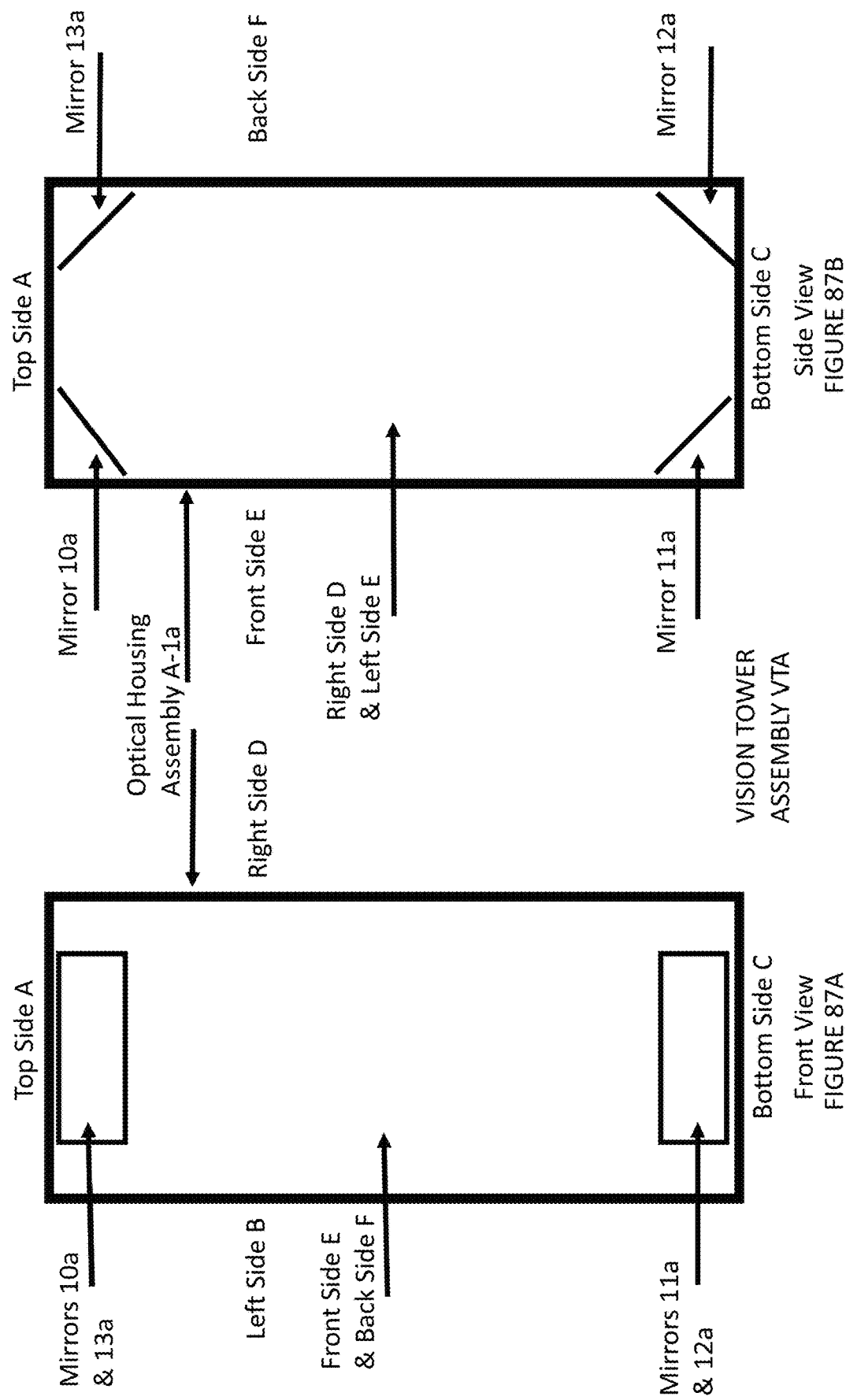
Figure 88:
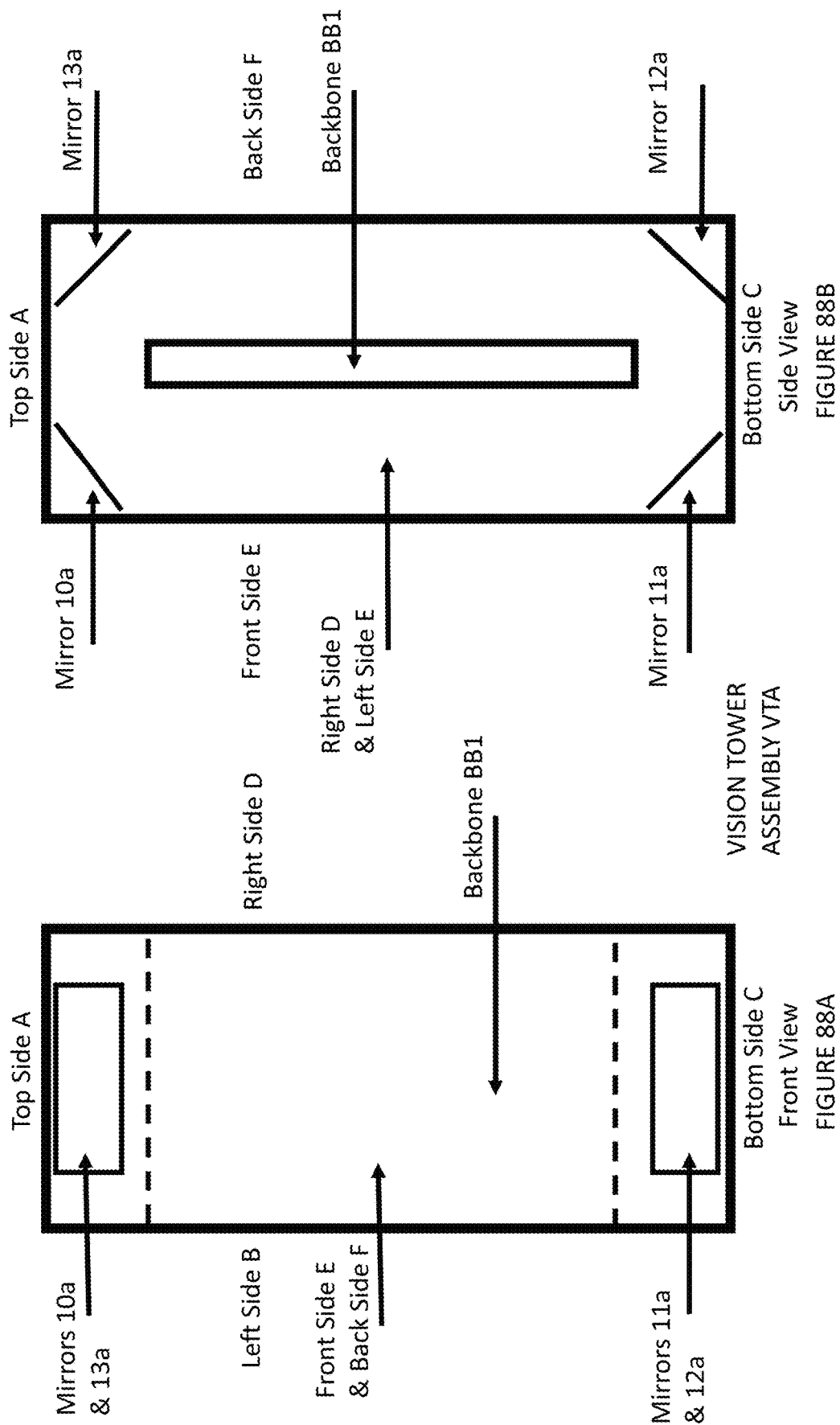

FIG. 86 shows two additional advantages of the present invention. One such advantage is the diversified revenue stream, which can protect the business from vertical-specific downturns. Fee revenue may account for 9.5% of total revenue, data revenue may account for 40.2% of total revenue while advertisement revenue may account for 50.3% of total revenue. Advertisement partners include large pharmaceutical companies, biotech companies, medical device companies, etc. Data sales are made to Data Management Platforms such as Oracle and Adobe. Data sales make HIPPA and privacy key. Another such advantage is the decline of per unit payback period as revenue/unit increases. Not only is revenue projected to increase in future years, the last month revenue/unit is also projected to increase in future years. For example, in FY 5, the total yearly revenue is projected to be about $450,000,000 while the revenue per unit per month in FY 5 is projected to be about $2,800. Strong revenue growth promotes falling payback period on each new unit manufactured and growth is predicated on just 2% interaction rate across locations.

FIGS. 87A-B show two views of an alternative embodiment according to aspects consistent with the innovations herein, noted subsequent to the description of FIG. 8, above. Such alternative embodiment(s), e.g., to the design depicted in FIGS. 3-8 may separate the subject/inventive device into two structures: here, for example 'Structure 1' may be comprised of components used to assess a user's distance vision including Optical Chamber Assembly A-a, mirrors 10a, 11a, 12a, 13a, and 14, Movable Housing Assembly MHA containing a User-Facing Mirror 14, and Downward Facing monitor E-4, Light Blocking Covers 40 and 41, such as, but not limited to bellows, tambour like covers, or shades, and a Lift Device E-8 consisting of either a linear actuator, motor, and controller, a lead screw, pneumatic actuators, or similar lift devices for providing vertical linear motion to the Movable Housing Assembly MHA. Structure 1 is referred to as Vision Tower Assembly, VTA. Further, 'Structure 2' may comprises the rest of the device, including but not limited to User-Facing Touch Screen Monitor E-15, Power Management E-1, Digital Signal Processor E-2, Communication System E-3 and other components described above. The two structures joined in manufacturing, shipped and operated as one unit, can be separated in the field for quick exchange replacement in the event of a component failure in either one of the structures.

In some implementations, the Vision Tower Assembly VTA is comprised of Optical Chamber Assembly A-1a consisting of six sides A, B, C, D, E and F, to which mirrors 10a, 11a, 12a, and 13a are attached as shown in FIGS. 87A-B.

As shown in FIGS. 88A-B, Component Backbone BB1, comprised of wood, metal, plastic, or other material, is inserted through the Right Side D and Left Side B of Vision Tower Assembly, VTA, terminating in a flush manner at the outer edges of Right Side D and Left Side B. Backbone BB1 provides the attachment surface to which a Lift Mechanism E-8 is joined, providing vertical motion to the Movable Housing Assembly MHA, containing User-Facing Mirror 14, and a Downward Facing Monitor E-4, as shown in FIGS. 88A-B. Alternative systems and methods for attaching Backbone BB! To right side D and left side B of the Vision Tower Assembly may include, though are not limited to, bolts, brackets, and welding, and/or other adhesive attachment devices, methods or solution.

Figure 89:
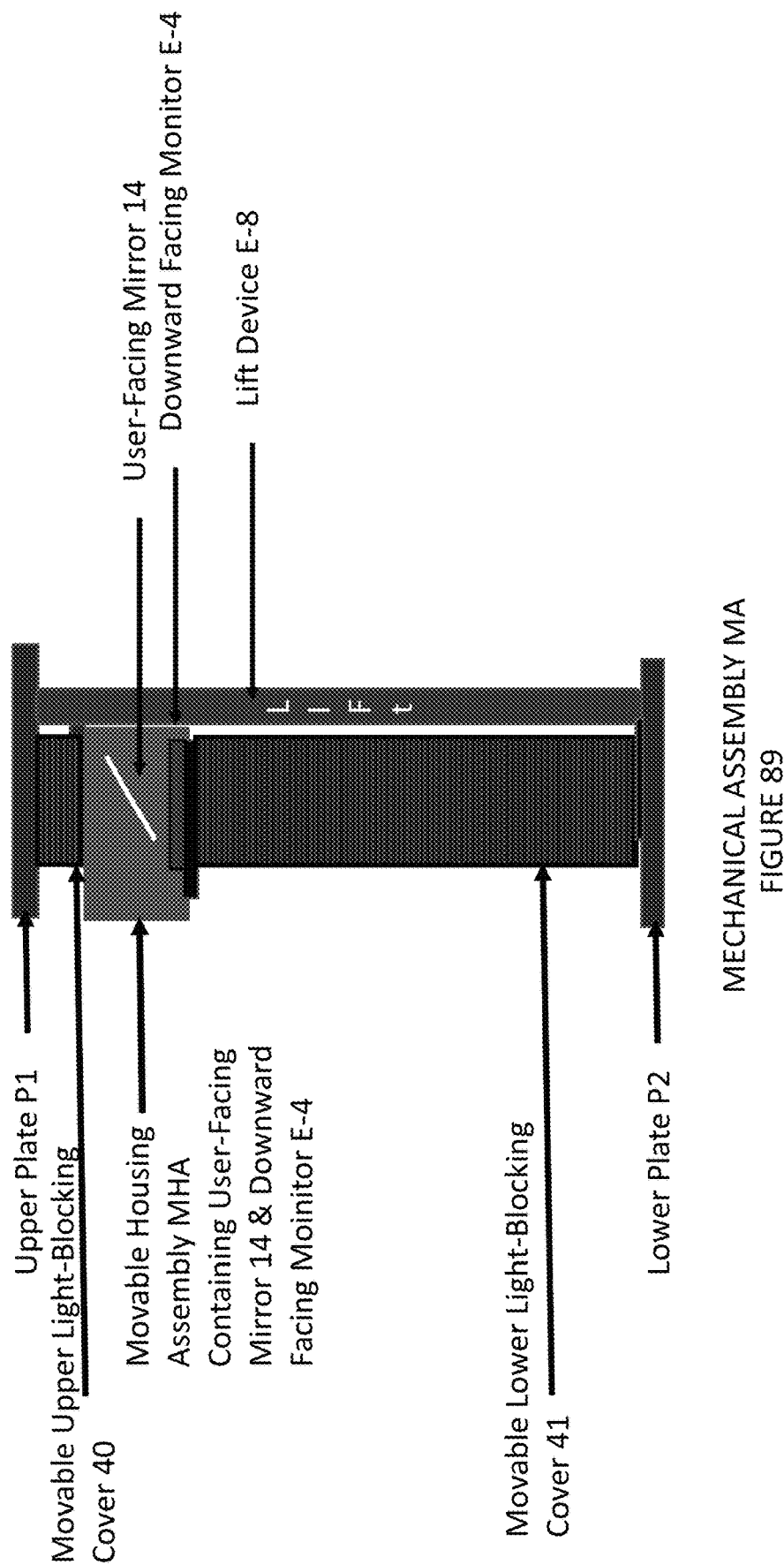

FIG. 89 depicts Mechanical Assembly MA comprised of an arrangement of components allowing the Movable Housing Assembly MHA to be adjusted to a user's height. Mechanical Assembly MA is comprised of components Upper Plate P1 and Lower Plate P2 to which the Upper Light-Blocking Cover 40 and Lower Light-Blocking Cover 41 are attached, respectively. Light-Blocking Covers are depicted as bellows in FIG. 89, one among many light-blocking options discussed above.

Further, in some aspects, between Upper and Lower Light-Blocking Covers 40 and 41, respectively, a Movable Housing Assembly MHA may be attached containing the User-Facing Mirror 14 and Downward Facing Monitor E-4. Lift Mechanism E-4 attaches to Movable Housing Assembly MHA and Backbone BB1 providing vertical motion to Movable Housing Assembly, MHA.

Figure 90:
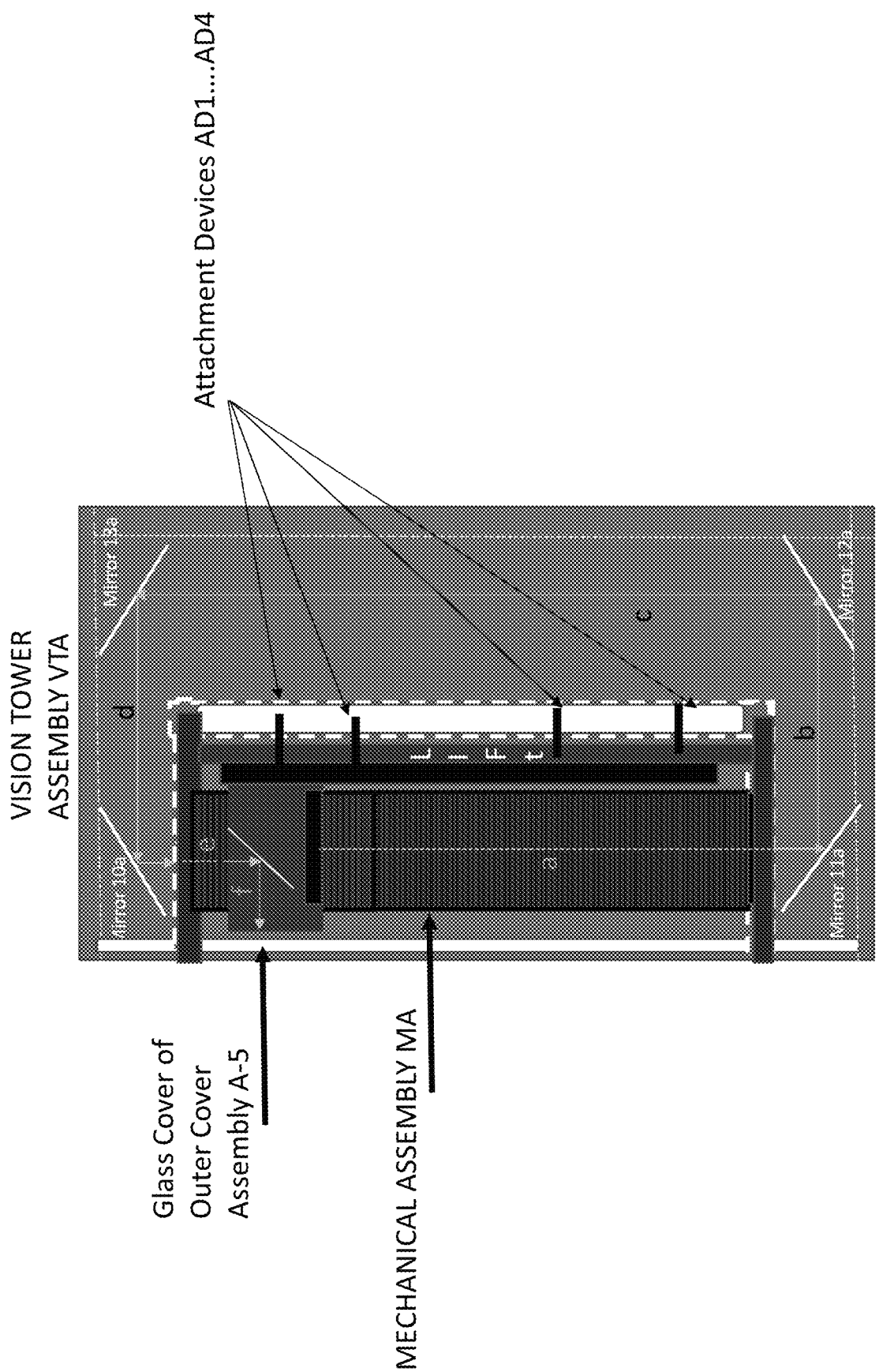

FIG. 90 shows the Mechanical Assembly MA placed within the Vision Tower Assembly VTA, and secured to BackBone BB1 with bolts, screws, or other Attachment Devices, AD1 . . . AD4. Also shown in a Glass Cover of Outer Cover Assembly A-5. FIG. 90 further shows the Optical Path a, b, c, d, e, and f enabling a user to see graphic symbols generated on Downward Facing Monitor, E-4 and reflecting upon mirrors 11a, 12a, 13a, 10a, and User-Facing Mirror 14.

Additional Example Implementation Details and Embodiments

Various of the processes, methods, and algorithms described in the preceding sections may be embodied in, and fully or partially automated by, code modules executed by one or more computer systems or computer processors comprising computer hardware. The code modules (or "engines") may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, for example, volatile or non-volatile storage.

In general, any use of the terms "engine" and "module", as used herein, refer to logic embodied in hardware and/or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language. It will be appreciated that software modules may be callable from other modules or from themselves, and/or may be invoked in response to detected events or interrupts. Software modules configured for execution on computing devices may be provided on a computer readable medium, such as memory, a compact disc, digital video disc, flash drive, or any other tangible medium. Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware. Generally, the modules described herein refer to logical modules that may be combined with other modules or divided into sub-modules despite their physical organization or storage. Electronic Data Sources can include databases, volatile/non-volatile memory, and any memory system or subsystem that maintains information.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others. While certain example embodiments have been described, these embodiments have been presented by way of example only, and are not intended to limit the scope of the disclosure. Thus, nothing in the foregoing description is intended to imply that any particular element, feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

Any process descriptions, elements, or blocks in the flow diagrams described herein and/or depicted in the attached figures should be understood as potentially representing modules, segments, or portions of code which include one or more executable instructions for implementing specific logical functions or steps in the process. Alternate implementations are included within the scope of the embodiments described herein in which elements or functions may be deleted, executed out of order from that shown or discussed, including substantially concurrently or in reverse order, depending on the functionality involved, as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated.

The invention claimed is:

1. A self-screening health and information device comprising:
a housing comprising internal mechanical components including one or more optical path mirrors along an optical path, at least one computational component, a moveable housing assembly (MHA), one or more electrical components, and a linear lift system comprising one or both of a manual lift system and/or an automated lift system;
   wherein the MHA includes a user-facing mirror and a first monitor that displays images along the optical path to the user-facing mirror; and
   wherein the MHA is moveably positioned along a vertical path and adjustable to a user's eye level;
   wherein the one or more optical path mirrors and the user-facing mirror define the optical path that contains the MHA, originates at the first monitor, and extends to the user-facing mirror, the optical path being configured with an overall optical path length that remains constant throughout movement of the MHA along the vertical path to adjust to the user's eye level via adjustment to a length of a first segment of the optical path while performing a corresponding length adjustment to a second segment of the optical path that compensates for the adjustment of the first segment;
one or more computer-readable media, computing and/or data storage devices in the housing and including artificial intelligence (AI) and/or algorithms that perform processing to execute a computer implemented process comprised of:
   providing a user with a plurality of health screening options via one or more graphical user interfaces (GUIs), the plurality of health screening options comprising vision screening options for one or more of: a near vision screening, a distance vision screening, a central vision screening, an ocular allergy screening, a contrast sensitivity screening, a peripheral vision screening, a color vision screening, an anterior eye screening, and/or a posterior eye screening; and
   providing, upon receiving a health screening option selected by the user, a health screening protocol corresponding to the health screening option selected;
one or more monitors or displays in the housing, including:
   the first monitor, the first monitor being configured to present visual indicia to the user for assessing vision and/or eye health of the user; and
   a second monitor having an interactive display, wherein the second monitor is configured to display one or more user interfaces including:
      a first user interface (first UI) that displays, to the user, the plurality of health screening options and one or more UI elements for navigation between the plurality of health screening options, the plurality of health screening options including (i) a first option to screen the user's vision and/or eye health, (ii) at least one second option for screening or assessing one or more additional conditions of the user selected from a group composed of BMI, diabetes, smoking screening, health issues based on analysis of hand and/or skin screenings, blood pressure, pulse, heart rate, EKG, breath analysis, and/or hearing; and (iii) a third option including a screen configured to provide audiovisual information associated with: the user's vision and/or eye health, the one or more additional conditions, recorded health information, and/or telemedicine information associated with a telemedicine appointment;

a communication component in the housing configured to one or both of:

provide the user ability to communicate by audio, video and/or text with a health care professional related to one or more of the health screening options, and/or a recommendation provided by the device and/or generated via screening results based on the health screening options; and/or communicate the screening results and/or one or more user system inputs to a user-selected health care professional; and at least one speaker and/or microphone that provides audio communication between the user and the device.

2. The device of claim 1, wherein the housing is 18 to 36 inches wide, 30 to 48 inches tall, and 8 to 18 inches deep, and weighs between 15 and 50 pounds.

3. The device of claim 1, wherein the automated lift system includes a linear actuator coupled to the MHA and positioned to move the MHA in a vertical direction.

4. The device of claim 1, further comprising a motor operable to move the user facing mirror and one or more mechanical, electrical, optical, and/or lens components connected to a motor, which provides rotation to the user-facing mirror for screening vision acuity and providing a back of the eye analysis, consecutively, or given sufficient rotational speed of the motor, simultaneously.

5. The device of claim 1, wherein one or more of the monitors and/or components of the device provide for user input and device navigation through detection of touch, voice commands, hand and other bodily movements and gestures for hands and/or hands-free device operation.

6. The device of claim 1, wherein a video and audio library of results for each health screening along with system algorithms, are threaded together, to generate and provide textual information for display to the user regarding results of the health screenings that the user conducts.

7. The device of claim 1, wherein typed on-screen responses accompany video or audio results and responses, and/or are used independently of video or audio.

8. The device of claim 1, wherein the constant optical path length is composed of fixed segments [b, c and d] and variable segments [a and e], which are configurable to provide for different vision acuity screenings by altering size of displayed icons on a monitor and concurrently allow the device to adjust to an eye level of the user.

9. The device of claim 1, wherein the first monitor is positioned beside the user-facing mirror, with the first monitor and the user facing mirror being enclosed in the MHA, wherein one or more first segments of the optical path situated on one side of the MHA and one or more second segments on another side of the MHA are configured to reciprocally change in length to maintain a constant total optical path length while the user-facing mirror is adjusted to the user's eye level.

10. The device of claim 1, further comprising:

an upper plate and a lower plate positioned, respectively, on top of and on bottom of a cut-out in the device into which a hand of the user is placed for hand screening;

one or more screening devices comprising one or more of: a black and white camera, a color camera, an ultra-violet light source, an ultra-violet camera, one or more lasers, an oxygen sensor, a temperature sensor, a pressure sensor, and/or an electrical sensor, which are configured to screen two or more of the following: galvanic skin response, hand swelling, nail conditions, veins, finger joints and tips, finger length, reflex responses, and/or screening of various skin conditions.

11. The device of claim 1, further comprising:

an upper plate and a lower plate positioned, respectively, on top of and on bottom of a cut-out in the device into which a hand of the user is placed for hand screening; and one or more sensors, associated with the upper plate and/or lower plate, for screening a surface of a user's hands and providing feedback information;

wherein the device is configured to, as a function of the feedback information received from the one or more sensors:

(i) assess the user's health via h hand screening; and (ii) detect a health condition or skin disorder including one or more of skin cancer, joint issues, liver problems, osteoarthritis, thyroid and hypothyroidism, anemia, lung disease, pulse, heart rate, and impaired oxygen level.

12. The device of claim 1, further comprising one or more components that take images of a posterior region of the eye of the user, the one or more components comprising one or more of:

a camera, an infra-red camera and/or sensor, a lens, and a mirror;

wherein at least one of the one or more components is contained in a movable device held to the user's eye and connected electronically to the device.

13. The device of claim 1 wherein the plurality of user interfaces further includes:

a second user interface (second UI) configured to provide one or more user-selectable health apps, for download, to a mobile device of the user via a wireless communication element.

14. The device of claim 1, wherein the one or more computer-readable media, computing and/or data storage devices includes the AI;

wherein the device is configured to obtain a screening or a posterior or back of the eye of the user; and wherein, based on the screening, the AI is configured to:

(i) provide an assessment or result of the user's ocular health and/or overall health, and (ii) interpret the assessment or results to determine presence of a deteriorating eye condition, a disease, or a health condition selected from a group composed of macular degeneration, diabetic retinopathy, cataracts, glaucoma, ocular sun (UV) damage, ocular allergies, ocular symptoms related to computer use, smart phones and/or other visually dependent electronic devices, hypertension, cholesterol levels, diabetes, and heart disease.

15. The device of claim 1, wherein in response to user input, or system measurement, of height and/or weight of the user, the system is configured to calculate the user's BMI and provide, via the first UI, an interactive onscreen app enabling interactive modeling of the user's BMI based on one or more inputs from the user.

16. The device of claim 1 wherein the device is configured to:

provide, via the first UI, a second option that provides a diabetic screening to the user; and in response to the user's selection of the diabetic screening:

provide an interactive self-screening related to diabetes, including presentation, via the display, of one or more questions for the user; and instruct the user to perform at least one self-screening by selecting one or more of the plurality of health screening options.

17. The device of claim 16 wherein the device is configured to:
   determine a risk of a presence of diabetes or a pre-diabetes condition based on information obtained from the self-screening; and
   upon determination of a potential diabetes or the pre-diabetes condition:
      inform the user of the risk and/or the presence of diabetes or the pre-diabetes condition; and
      provide the user with: (i) behavior modification actions and activities to delay or prevent an onset of diabetes, and/or (ii) information and screenings to manage diabetic symptoms or conditions associated with one or more of vision, hearing, oral health, skin, and foot health.

18. The device of claim 1 further comprising at least one spectrum analyzer configured to provide assessment of the user's breath.

19. The device of claim 1 wherein the device is configured to enable the user to download one or more health apps to their smart phone, wearable health devices, or computers, and
   wherein the data derived from the one or more health apps is automatically feed into a user health account of the user associated with the device.

20. The device of claim 1, wherein the device is configured to display advertising and branded information content as video, text or graphical information on the one or more monitors or displays, and/or as audio information via a speaker or audio output;
   wherein one or both of the advertising and/or product suggestions are selected as a result of the screening results; and
   wherein advertising content is configured to display with screening results, health or other information requested by user, and provided for display on the one or more monitors or displays and/or sent to a mobile or other computer device associated with the user.

21. The device of claim 1 wherein the device is configured to display, via the first UI, a third option comprising a graphical user interface by which a requesting entity generates one or more requests to the user to select specific screenings and/or answer specific questions, wherein the one or more requests are made prior to screening by the device or during the screening via audio, video or electronic communication.

* * * * *